(12) United States Patent
Braun et al.

(10) Patent No.: US 9,002,654 B2
(45) Date of Patent: Apr. 7, 2015

(54) MULTI-ANALYTE ANALYSIS OF SALIVA BIOMARKERS AS PREDICTORS OF PERIODONTAL AND PRE-IMPLANT DISEASE

(75) Inventors: Thomas Braun, Ann Arbor, MI (US); William V. Giannobile, Ann Arbor, MI (US); Amy E. Herr, Oakland, CA (US); Anup K. Singh, Danville, CA (US); Charlie Shelburne, Whitmore Lake, MI (US)

(73) Assignees: The Regents of the University of Michigan, Ann Arbor, MI (US); Sandia National Laboratories, Livermore, CA (US)

( * ) Notice: Subject to any disclaimer, the term of this patent is extended or adjusted under 35 U.S.C. 154(b) by 647 days.

(21) Appl. No.: 12/670,072

(22) PCT Filed: Jul. 30, 2008

(86) PCT No.: PCT/US2008/071596
§ 371 (c)(1),
(2), (4) Date: Apr. 21, 2010

(87) PCT Pub. No.: WO2009/018342
PCT Pub. Date: Feb. 5, 2009

(65) Prior Publication Data
US 2010/0196941 A1 Aug. 5, 2010

Related U.S. Application Data

(60) Provisional application No. 60/962,656, filed on Jul. 30, 2007.

(51) Int. Cl.
*G01N 33/48* (2006.01)
*G01N 31/00* (2006.01)
*G06G 7/48* (2006.01)
*G06G 7/58* (2006.01)
*G01N 33/68* (2006.01)

(52) U.S. Cl.
CPC ........ *G01N 33/6893* (2013.01); *G01N 2800/18* (2013.01)

(58) Field of Classification Search
CPC ........... G01N 2800/18; G01N 33/6893; A61K 2300/00
See application file for complete search history.

(56) References Cited

U.S. PATENT DOCUMENTS

| 5,736,341 | A | 4/1998 | Sorsa et al. |
| 6,143,506 | A * | 11/2000 | Golub et al. ................... 435/7.1 |
| 2001/0023324 | A1* | 9/2001 | Pronovost et al. ............ 600/582 |
| 2004/0181344 | A1* | 9/2004 | Stephanopoulos et al. ..... 702/20 |

OTHER PUBLICATIONS

Acharya et al., Immunomagnetic diffractometry for detection of diagnostic serum markers, J. Am. Chem. Soc., 129:15824-9 (2007).
(Continued)

*Primary Examiner* — Larry D Riggs, II
(74) *Attorney, Agent, or Firm* — Marshall, Gerstein & Borun LLP

(57) ABSTRACT

The present invention relates to methods of measuring biomarkers to determine the probability of a periodontal and/or peri-implant disease. More specifically, the invention provides a panel of biomarkers that, when used in combination, can allow determination of the probability of a periodontal and/or peri-implant disease state with extremely high accuracy.

24 Claims, 9 Drawing Sheets

(56) References Cited

OTHER PUBLICATIONS

Ausubel (ed.), UNIT 26.0 Gene Silencing, Current Protocols in Molecular Biology, Jul. 2008.
Bamber, The area above the ordinal dominance graph and the area below the receiver operating characteristic graph, Br. J. Math Stat. Psychol., 12:387-415 (1975).
Bobetsis et al., Bacterial infection promotes DNA hypermethylation, J. Dent. Res., 86:169-74 (2007).
Borrell et al., Analytical epidemiology of periodontitis, J. Clin. Periodontol., 32:132-58 (2005).
Breiman, Random forests, Machine Learning, 45:5-32 (2001).
Chen et al., A microfluidic system for saliva-based detection of infectious diseases, Ann N Y Acad. Sci., 1098:429-36 (2007).
Christodoulides et al., Lab-on-a-chip methods for point-of-care measurements of salivary biomarkers of periodontitis, Ann N Y Acad. Sci., 1098:411-28 (2007).
Coligan (ed.), UNIT 8.0 Isolation and Analysis of Proteins, Current Protocol in Protein Science, May 2008.
Delaney et al., Performance of an oral fluid rapid HIV-1/2 test: experience from four CDC studies, AIDS, 20:1655-60 (2006).
Dykxhoorn et al., Killing the messenger: short RNAs that silence gene expression, Nature Reviews Molecular Cell Biology, 4:457-67 (2003).
Golub et al., A matrix metalloproteinase inhibitor reduces bone-type collagen degradation fragments and specific collagenases in gingival crevicular fluid during adult periodontitis, *Inflamm. Res.*, 46:310-9 (1997).
Greenstein et al., A critical assessment of interleukin-1 (IL-1) genotyping when used in a genetic susceptibility test for severe chronic periodontitis, J. Periodontol., 73:231-47 (2002).
Haab et al., RCA-enhanced protein detection arrays, Methods Mol. Biol., 328:15-29 (2006).
Haffajee et al., Clinical risk indicators for periodontal attachment loss, J. Clin. Periodontol., 18:117-25 (1991).
Herr et al., Microfluidic immunoassays as rapid saliva-based clinical diagnostics, Proc. Natl. Acad. Sci. USA, 104:5268-73 (2007).
International Preliminary Report on Patentability from corresponding International Application No. PCT/US08/71596, dated Feb. 2, 2010.
International Search Report and Written Opinion from corresponding International Application No. PCT/US08/71596, dated Dec. 23, 2008.
Kinane et al., Changes in gingival crevicular fluid matrix metalloproteinase-8 levels during periodontal treatment and maintenance, *J. Periodontal Res.*, 38:400-4 (2003).
Kinney et al., Oral fluid-based biomarkers of alveolar bone loss in periodontitis, Ann. N Y Acad. Sci, 1098:230-51 (2007).
Kornman et al., Re: A critical assessment of interleukin-1 (IL-1) genotyping when used in a genetic susceptibility test for severe chronic periodontitis. Greenstein G, Hart TC (2002;73:231-247), J. Periodontol., 73:1553-6 (2002).
Lee et al., Microarray methods for protein biomarker detection, Analyst, 133:975-83 (2008).
Li et al., Salivary transcriptome diagnostics for oral cancer detection, Clin. Cancer Res., 10:8442-50 (2004).
Liszewski, Biomarker detection & measurement: Harnessing useful diangostic and therapeutic information, Gen. Eng. Biotech. News (Mar. 15, 2006).
Loesche et al., Trypsin-like activity in subgingival plaque. A diagnostic marker for spirochetes and periodontal disease?, J. Periodontol., 58:266-73 (1987).
Malamud, Salivary diagnostics: the future is now, J. Am. Dent. Assoc., 137:284, 286 (2006).
Mandel et al., The salivary secretions in health and disease, Oral Sci. Rev., 8:25-47 (1976).
Mauk et al., Lab-on-a-chip technologies for oral-based cancer screening and diagnostics: capabilities, issues, and prospects, Ann N Y Acad. Sci., 1098:467-75 (2007).
Mittal, Improving the efficiency of RNA interference in mammals, Nat. Rev. Gen., 5:355-65 (2004).
Mullally et al., Prevalence of periodontal pathogens in localized and generalized forms of early-onset periodontitis, J. Periodontal Res., 35:232-41 (2000).
Oringer et al., C-telopeptide pyridinoline cross-links (ICTP) and periodontal pathogens associated with endosseous oral implants, *Clin. Oral Implants Res.*, 9:365-73 (1998).
Palys et al., Relationship between C-telopeptide pyridinoline cross-links (ICTP) and putative periodontal pathogens in periodontitis, J. Clin. Periodontol., 25:865-71 (1998).
Pan et al., High throughput proteome screening for biomarker detection, Mol. Cell. Proteomics, 4:182-90 (2005).
Prescher et al., Rapid quantitative chairside test for active MMP-8 in gingival crevicular fluid: first clinical data, Ann N Y Acad Sci., 1098:493-5 (2007).
Sambrook et al. (eds.), Molecular Cloning: A Laboratory Manual (Third Edition), CSH Press (2001).
Schallmeiner et al., Sensitive protein detection via triple-binder proximity ligation assays, Nat. Methods, 4:135-7 (2007).
Shelburne et al., Quantitation of *Bacteroides forsythus* in subgingival plaque comparison of immunoassay and quantitative polymerase chain reaction, J. Microbiol. Methods, 39:97-107 (2000).
Shelburne et al., Serum antibodies to *Porphyromonas gingivalis* chaperone HtpG predict health in periodontitis susceptible patients, PLoS One, 3:e1984 (2008).
Socransky et al., Microbial complexes in subgingival plaque, J. Clin. Periodontol., 25:134-44 (1998).
Taba et al., Diagnostic biomarkers for oral and periodontal diseases, Dent. Clin. North Am., 49:551-71, vi (2005).
Tabak, Point-of-care diagnostics enter the mouth, Ann N Y Acad. Sci., 1098:7-14 (2007).
Tonetti et al., Advances in the progression of periodontitis and proposal of definitions of a periodontitis case and disease progression for use in risk factor research. Group C consensus report of the 5th European Workshop in Periodontology, J. Clin. Periodontol., 32 Suppl 6:210-3 (2005).
Wong et al., Salivary diagnostics powered by nanotechnologies, proteomics and genomics, J. Am. Dent. Assoc., 137:313-21 (2006).
Yager et al., Microfluidic diagnostic technologies for global public health, Nature, 442:412-8 (2006).
Yan et al., Targeted biomarker detection via whole protein ion trap tandem mass spectrometry: thymosin beta4 in a human lung cancer cell line, J. Mass. Spectrom., 40:444-51 (2005).
Zimmermann et al., Salivary mRNA targets for cancer diagnostics, Oral Onc., 44:425-9 (2008).
Takeuchi et al., *Treponema socranskii, Treponema denticola*, and *Porphyromonas gingivalis* are associated with severity of periodontal tissue destruction, J. Periodontal., 72:1354-63 (2001).
Hemmings et al., Detection of neutral protease (Periocheck) and BANA hydrolase (Perioscan) compared with traditional clinical methods of diagnosis and monitoring of chronic inflammatory periodontal disease, J. Clin. Periodontol., 24:110-4 (1997).

\* cited by examiner

US 9,002,654 B2

SEQUENCE LISTING

<160> NUMBER OF SEQ ID NOS: 16

<210> SEQ ID NO 1
<211> LENGTH: 18
<212> TYPE: DNA
<213> ORGANISM: Artificial Sequence
<220> FEATURE:
<223> OTHER INFORMATION: Synthetic Primer

<400> SEQUENCE: 1
ggcacgtagg cggacctt                                                    18

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
accagggcta aagcccaatc                                                  20

<210> SEQ ID NO 3
<211> LENGTH: 23
<212> TYPE: DNA
<213> ORGANISM: Artificial Sequence
<220> FEATURE:
<223> OTHER INFORMATION: Synthetic Primer

<400> SEQUENCE: 3
tttcggagcg taaactcctt ttc                                    23

<210> SEQ ID NO 4
<211> LENGTH: 21
<212> TYPE: DNA
<213> ORGANISM: Artificial Sequence
<220> FEATURE:
<223> OTHER INFORMATION: Synthetic Primer

<400> SEQUENCE: 4
tttctgcaag cagacactct t                                      21

<210> SEQ ID NO 5
<211> LENGTH: 25
<212> TYPE: DNA
<213> ORGANISM: Artificial Sequence
<220> FEATURE:
<223> OTHER INFORMATION: Synthetic Primer

<400> SEQUENCE: 5
accagcgttt gacatcttag gaatg                                  25

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
agccatgcac ctgtctttag                                        20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
agattgacgg ccctatgggt                                        20

<210> SEQ ID NO 8
<211> LENGTH: 21
<212> TYPE: DNA
<213> ORGANISM: Artificial Sequence
<220> FEATURE:
<223> OTHER INFORMATION: Synthetic Primer

<400> SEQUENCE: 8
ccggtcctta ttcgaagggt a                                      21

<210> SEQ ID NO 9
<211> LENGTH: 26
<212> TYPE: DNA
<213> ORGANISM: Artificial Sequence
<220> FEATURE:
<223> OTHER INFORMATION: Synthetic Primer

<400> SEQUENCE: 9
catagatatc acgaggaact ccgatt                                 26

<210> SEQ ID NO 10
<211> LENGTH: 25

```
<212> TYPE: DNA
<213> ORGANISM: Artificial Sequence
<220> FEATURE:
<223> OTHER INFORMATION: Synthetic Primer

<400> SEQUENCE: 10
aaactgttag caactaccga tgtgg                                          25

<210> SEQ ID NO 11
<211> LENGTH: 24
<212> TYPE: DNA
<213> ORGANISM: Artificial Sequence
<220> FEATURE:
<223> OTHER INFORMATION: Synthetic Primer

<400> SEQUENCE: 11
gggtgagtaa cgcgtatgta acct                                           24

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
acccatccgc aaccaataaa                                                20

<210> SEQ ID NO 13
<211> LENGTH: 19
<212> TYPE: DNA
<213> ORGANISM: Artificial Sequence
<220> FEATURE:
<223> OTHER INFORMATION: Synthetic Primer

<400> SEQUENCE: 13
cgttcctggg ccttgtaca                                                 19

<210> SEQ ID NO 14
<211> LENGTH: 21
<212> TYPE: DNA
<213> ORGANISM: Artificial Sequence
<220> FEATURE:
<223> OTHER INFORMATION: Synthetic Primer

<400> SEQUENCE: 14
tagcgacttc aggtaccctc g                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic Primer

<400> SEQUENCE: 15
ccatgaagtc ggaatcgcta g                                              21

<210> SEQ ID NO 16
<211> LENGTH: 16
<212> TYPE: DNA
<213> ORGANISM: Artificial Sequence
<220> FEATURE:
<223> OTHER INFORMATION: Synthetic Primer
```

```
<400> SEQUENCE: 16
gcttgacggg cggtgt                                              16
```

MULTI-ANALYTE ANALYSIS OF SALIVA BIOMARKERS AS PREDICTORS OF PERIODONTAL AND PRE-IMPLANT DISEASE

CROSS-REFERENCE TO RELATED APPLICATIONS

This application is the U.S. national phase of International Application No. PCT/US08/71596, filed Jul. 30, 2008, which claims priority of U.S. Provisional Application No. 60/962,656 filed Jul. 30, 2007 and is hereby incorporated by reference in its entirety.

STATEMENT OF GOVERNMENT INTEREST

This invention was made with Government support under grant number U01-DE014961 awarded by The National Institute of Dental and Craniofacial Research (NIDCR) and grant number DE-AC04-94AL85000, awarded by the Department of Energy (DOE). The Government has certain rights in the invention.

FIELD OF THE INVENTION

The present invention relates to methods of measuring biomarkers to determine the probability of a periodontal and/or peri-implant disease. More specifically, the invention provides a panel of biomarkers that, when used in combination, can allow determination of the probability of a periodontal and/or peri-implant disease state with extremely high accuracy.

BACKGROUND OF THE INVENTION

Periodontal diseases are the leading cause of tooth loss in adults. Periodontitis is initiated by tooth-associated subgingival biofilms trigger an altered host response leading to soft tissue inflammation and subsequent bone loss. Periodontal infections are implicated in a variety of other diseases (such as cardiovascular disease, stroke and aspiration pneumonia) whereby the microbial biofilm serves as a "slow delivery system" of oral pathogens adhering to teeth leading to a chronic microbial challenge and downstream effects of an altered host response to the patient. Diagnostic methods in clinical practice today lack the ability to both detect the onset of inflammation and to identify those patients susceptible to future disease progression. Oral-fluid-based point-of-care (POC) diagnostics are commonly used for various diagnostic tests in medicine and more recently are being adapted for the determination of oral diseases (Tabak, 2007, Ann N Y Acad Sci 1098: 7-14). Recent clinical applications use new "lab-on-a-chip, LOC" technologies as rapid POC diagnostics of systemic infectious diseases (Chen et al., 2007, Ann NY Acad Sci 1098: 429-436; Mauk et al., 2007, Ann N Y Acad Sci 1098: 467-475) and periodontal disease (Herr et al., 2007, Proc Natl Acad Sci USA 104: 5268-5273). The human salivary proteome project, supported by the U.S. National Institute of Craniofacial Research (NIDCR), has further generated emphasis on the use of proteomic markers for disease diagnosis (Wong, 2006, J Am Dent Assoc 137: 313-321).

In oral-based diagnostics, the use of oral fluids has successfully demonstrated its ease of use for POC application (Malamud, 2006, J Am Dent Assoc 137: 284-286) for the detection of oral cancer (Li et al., 2004, Clin Cancer Res 10: 8442-8450; Zimmermann et al., 2008, Oral Oncol. 44(5): 425-9) or HIV infection (Delaney et al., 2006, Aids 20: 1655-1660). Furthermore, the use of microfluidic devices as examples of LOC technology offers significant potential for rapid saliva diagnosis for widespread public health purposes (Herr et al., 2007, Proc Natl Acad Sci USA 104: 5268-5273; Yager et al., 2006, Nature 442: 412-418). However, for periodontal disease determination, most research to date has focused primarily on gingival crevicular fluid (GCF) biomarkers that provide local disease status, but represent a cumbersome, difficult to utilize approach for clinical application (Taba et al., 2005, Dent Clin North Am 49: 551-571, vi). Easy-to-access saliva contains both locally and systemically-derived mediators of periodontal disease and thus offers significant potential for the assessment of periodontal disease status and risk (Kinney et al., 2007, Ann N Y Acad Sci 1098: 230-251).

Periodontal and peri-implant disease activity presently are diagnosed by clinical parameters such as pocket depth, bleeding on probing, and radiographs. These parameters have limitations in that they lack ability to predict future attachment loss, and provide information only on the existence of past disease activity. The need for diagnostics in clinical dentistry that are predictive markers of active periodontitis is a focus of present research. Periodontal disease is a general term used to describe specific diseases that affect the gingiva, as well as the supporting connective tissues and alveolar bone that anchor the teeth in the jaws. The periodontal diseases are among the most common infectious diseases in humans. In the last fifteen years, with the decline of dental caries in children aged 6-18, and better prevention programs for the general population, periodontal disease leading to tooth loss has assumed even greater importance.

As more teeth are retained due to reduced cavities, more teeth are at risk to be affected by periodontal disease.

The use of clinical parameters for the diagnosis of periodontal disease has numerous limitations. For example, Haffajee and co-workers ("Clinical risk indicators for periodontal attachment loss," Journal of Clinical Periodontology, 1991; v. 18:117-125) have demonstrated that no clinical parameters have been shown to be predictive for periodontal disease activity. Thus, there have been intensive research efforts to develop diagnostic tests for periodontal disease evaluation. Over 60 different tests for oral fluid components have been studied with no single oral fluid biomarker demonstrating utility as a clinically available diagnostic (reviewed in Taba et al, "Diagnostic biomarkers for oral and periodontal diseases," Dental Clinics of North America, 2005; v. 49:551-571).

Despite the plethora of such components, there are at present no diagnostic tests available which have been demonstrated to be highly predictive for periodontal disease. As the breakdown of these components is the ultimate concern of the practitioner, their destruction should be evaluated.

Thus, the recognition and diagnosis of periodontal disease has become even more important, and there exists a need in the art for rapid, accurate and sensitive methods for diagnosing and assessing the degree of periodontal diseases.

SUMMARY OF THE INVENTION

The present invention demonstrates a role for biomarker levels as an indicator of oral disease. Work described herein demonstrates that elevated levels of multiple biomarkers can be used as a tool for accurately and rapidly determinining the probability of oral disease.

Thus, the present invention provides methods for determining the probability of an oral disease state comprising the step of determining the levels of two or more biomarkers in a sample from a first individual, said levels of said two or more biomarkers indicating the probability of said oral disease state.

The present invention also provides diagnostic methods wherein the levels of two or more biomarkers are indicative of oral disease if said levels of said two or more biomarkers from said first individual are elevated compared to levels of identical biomarkers from a second individual.

The present invention also provides methods for determining susceptibility to oral disease wherein the levels of two or more biomarkers are indicative of susceptibility to oral disease if said levels of said two or more biomarkers from a first individual are elevated compared to levels of identical biomarkers from a second individual.

The present invention further provides methods wherein the levels of two or more biomarkers are indicative of susceptibility to oral disease if said levels of said two or more biomarkers from a first individual are elevated compared to biomarker levels in a sample from the first individual measured at an earlier time point.

The present invention also provides methods wherein the levels of two or more biomarkers are indicative of progression of oral disease if said levels of said two or more biomarkers from a first individual are elevated compared to biomarker levels in a sample from the first individual measured at an earlier time point.

The present invention additionally provides methods for determining effectiveness of oral disease treatment wherein the levels of said two or more biomarkers are indicative of effective oral disease treatment if said levels of said two or more biomarkers from a first individual are decreased compared to levels of identical biomarkers from the same individual measured at an earlier time point.

In one aspect, the invention provides methods wherein the occurance of an oral disease is diagnosed at a probability equal to or greater than 70%.

In another aspect, methods are provided wherein the occurance of an oral disease is diagnosed at a probability equal to or greater than 80%.

In still another aspect, method are provided wherein the occurance of an oral disease is diagnosed at a probability equal to or greater than 90%.

In an aspect of the methods, the levels of two biomarkers are determined and used to calculate the probability of oral disease.

In other aspects of the methods, the levels of three, four, or five biomarkers are determined and used to calculate the probability of oral disease.

In still other aspects of the methods, the levels of six, seven, eight, nine, ten, eleven, twelve, thirteen, fourteen, fifteen, twenty or more biomarkers are determined and used to calculate the probability of oral disease.

In various aspects of methods of the invention, the two or more biomarkers are selected from the group consisting of *Aggregatibacter actinomycetemcomitans, Campylobacter rectus, Fusobacterium nucleatum, Prevotella intermedia, Porphyromonas gingivalis, Tannerella forsythia, Treponema denticola*, matrix metalloproteinase-8 (MMP-8), matrix metalloproteinase-9 (MMP-9), osteoprotegerin (OPG), type I collagen pyridinoline cross-linked telopeptide (ICTP), interleukin-1 beta (IL-1β), interleukin-6 (IL-6), interleukin-4 (IL-4), interleukin-10 (IL-10), interleukin-2 (IL-2), interleukin-13 (IL-13), calprotectin, tumor necrosis factor α (TNFα) and combinations thereof.

In various embodiments of the methods, the two or more biomarkers include the combinations of biomarkers: Calprotectin+MMP9, MMP8+Calprotectin, MMP8+ICTP, MMP9+TNFa, MMP9+ICTP, MMP8+TNFa, MMP8+OPG, MMP9+OPG, MMP8+IL1beta, MMP8+MMP9, MMP8+IL10, MMP9+IL1beta, MMP9+IL6, MMP8+IL4, MMP9+IL4, MMP8+IL6, MMP8+IL2, MMP9+IL10, MMP9+IL2, MMP9+IL13, MMP8+IL13, Calprotectin+IL6, Calprotectin+OPG, Calprotectin+ICTP, Calprotectin+IL4, Calprotectin+IL10, IL6+ICTP, Calprotectin+IL1beta, Calprotectin+IL2, Calprotectin+TNFa, Calprotectin+IL13, IL6+TNFa, OPG+IL6, IL6+IL4, IL6+IL13, ICTP+IL4, ICTP+IL1beta, ICTP+IL10, IL6+IL1beta, IL6+IL2, IL4+TNFa, OPG+ICTP, IL6+IL10, ICTP+TNFa, ICTP+IL2, OPG+IL4, IL13+IL4, ICTP+IL13, IL10+IL4, IL1beta+IL4, IL2+IL4, OPG+IL1beta, OPG+IL10, IL1beta+TNFa, IL10+IL13, IL1beta+IL10, IL10+TNFa, IL10+IL2, IL1beta+IL2, OPG+IL2, OPG+TNFa, IL1beta+IL13, IL2+TNFa, OPG+IL13, IL2+IL13, IL13+TNFa, Calprotectin+MMP9+OPG, Calprotectin+MMP9+ICTP, Calprotectin+MMP9+TNFa, MMP8+Calprotectin+OPG, Calprotectin+MMP9+IL1beta, Calprotectin+MMP9+IL10, Calprotectin+MMP9+IL6, MMP8+ICTP+TNFa, MMP8+Calprotectin+MMP9, MMP8+Calprotectin+ICTP, Calprotectin+MMP9+IL4, MMP8+Calprotectin+IL10, Calprotectin+MMP9+IL2, Calprotectin+MMP9+IL13, MMP8+Calprotectin+TNFa, MMP8+MMP9+TNFa, MMP8+Calprotectin+IL6, MMP8+OPG+ICTP, MMP9+ICTP+TNFa, MMP8+ICTP+IL10, MMP8+Calprotectin+IL1beta, MMP8+IL6+ICTP, MMP8+ICTP+IL1beta, MMP8+Calprotectin+IL4, MMP8+Calprotectin+IL2, MMP8+MMP9+ICTP, MMP8+ICTP+IL4, MMP9+OPG+TNFa, MMP9+IL4+TNFa, MMP8+ICTP+IL2, MMP9+IL6+TNFa, MMP8+ICTP+IL13, MMP8+Calprotectin+IL13, MMP8+IL2+TNFa, MMP8+MMP9+IL1beta, MMP9+IL6+ICTP, MMP9+IL10+TNFa, MMP8+OPG+TNFa, MMP8+IL10+TNFa, MMP9+OPG+ICTP, MMP9+IL2+TNFa, MMP9+ICTP+IL1beta, MMP8+OPG+IL10, MMP8+IL4+TNFa, MMP9+ICTP+IL10, MMP9+IL13+TNFa, MMP8+MMP9+OPG, MMP8+IL1beta+IL10, MMP9+ICTP+IL4, MMP9+ICTP+IL2, MMP8+IL6+TNFa, MMP9+IL1beta+TNFa, MMP8+OPG+IL6, MMP9+ICTP+IL13, MMP8+IL1beta+IL4, MMP8+OPG+IL4, MMP8+IL1beta+TNFa, MMP8+OPG+IL1beta, MMP8+IL13+TNFa, MMP8+OPG+IL13, MMP8+MMP9+IL6, MMP9+OPG+IL1beta, MMP8+MMP9+IL13, MMP8+OPG+IL2, MMP8+IL1beta+IL2, MMP9+IL6+IL1beta, MMP9+OPG+IL2, MMP9+OPG+IL6, MMP9+OPG+IL4, MMP8+IL1beta+IL13, MMP9+OPG+IL10, MMP8+IL10+IL13, MMP9+IL1beta+IL10, MMP9+IL1beta+IL4, MMP8+IL6+IL1beta, MMP8+MMP9+IL10, MMP9+IL1beta+IL13, MMP9+OPG+IL13, MMP9+IL6+IL4, MMP8+IL10+IL2, MMP8+IL10+IL4, MMP8+IL6+IL10, MMP8+MMP9+IL4, MMP9+IL6+IL2, MMP9+IL6+IL13, MMP8+MMP9+IL2, MMP8+IL6+IL4, MMP9+IL1beta+IL2, MMP9+IL2+IL4, MMP8+IL13+IL4, MMP9+IL13+IL4, MMP9+IL6+IL10, MMP8+IL2+IL4, MMP8+IL2+IL13, MMP9+IL10+IL13, MMP9+IL10+IL4, MMP8+IL6+IL2, MMP9+IL10+IL2, MMP8+IL6+IL13, Calprotectin+IL6+TNFa, MMP9+IL2+IL13, Calprotectin+OPG+ICTP, Calprotectin+IL6+ICTP, Calprotectin+OPG+IL6, Calprotectin+IL6+IL13, IL6+ICTP+IL13, Calprotectin+ICTP+IL4, Calprotectin+OPG+IL4, Calprotectin+OPG+IL1beta, Calprotectin+ICTP+IL10, Calprotectin+IL6+IL1beta, Calprotectin+IL6+IL2, Calprotectin+IL6+IL10, IL6+ICTP+TNFa, Calprotectin+IL6+IL4, OPG+IL6+ICTP, Calprotectin+ICTP+TNFa, IL6+IL4+TNFa, Calprotectin+OPG+IL10, Calprotectin+ICTP+IL1beta, Calprotectin+OPG+IL2, Calprotectin+IL4+TNFa, Calprotectin+OPG+IL2, Calprotectin+IL13+IL4, Calprotectin+ICTP+IL13, Calprotectin+OPG+TNFa, Calprotectin+IL10+IL2, Calprotectin+OPG+IL13, Calprotectin+IL10+

IL4, Calprotectin+IL1beta+IL4, Calprotectin+IL1beta+ IL10, Calprotectin+IL10+IL13, Calprotectin+IL1beta+ TNFa, Calprotectin+IL2+IL4, IL6+ICTP+IL4, Calprotectin+IL10+TNFa, IL6+IL13+IL4, ICTP+IL4+ TNFa, Calprotectin+IL1beta+IL13, IL6+ICTP+IL1beta, Calprotectin+IL1beta+IL2, IL6+ICTP+IL10, Calprotectin+ IL2+TNFa, IL6+ICTP+IL2, Calprotectin+IL2+IL13, ICTP+ IL13+IL4, IL6+IL10+TNFa, OPG+IL6+IL13, Calprotectin+ IL13+TNFa, IL6+IL1beta+TNFa, IL6+IL2+IL13, OPG+ IL4+TNFa, OPG+IL6+IL4, OPG+IL6+TNFa, OPG+IL6+ IL1beta, IL6+IL1beta+IL13, IL10+IL13+IL4, IL2+IL4+ TNFa, ICTP+IL2+TNFa, IL10+IL4+TNFa, ICTP+IL2+IL4, OPG+ICTP+IL4, ICTP+IL10+IL13, IL6+IL10+IL4, IL6+ IL2+TNFa, ICTP+IL1beta+IL4, OPG+IL6+IL2, IL6+ IL1beta+IL4, IL6+IL2+IL4, OPG+IL6+IL10, ICTP+ IL1beta+TNFa, ICTP+IL10+IL4, ICTP+IL10+TNFa, OPG+ ICTP+IL1beta, IL6+IL13+TNFa, IL6+IL10+IL13, ICTP+ IL1beta+IL10, IL1beta+IL2+TNFa, OPG+ICTP+IL10, IL1beta+IL4+TNFa, ICTP+IL10+IL2, ICTP+IL1beta+IL2, ICTP+IL1beta+IL13, IL13+IL4+TNFa, IL6+IL10+IL2, OPG+ICTP+IL2, OPG+ICTP+TNFa, IL1beta+IL13+IL4, OPG+ICTP+IL13, IL6+IL1beta+IL2, OPG+IL13+IL4, IL6+ IL1beta+IL10, IL10+IL2+IL13, ICTP+IL13+TNFa, OPG+ IL10+IL4, ICTP+IL2+IL13, OPG+IL1beta+IL4, OPG+IL2+ IL4, IL2+IL13+IL4, OPG+IL10+TNFa, OPG+IL1beta+ IL13, OPG+IL10+IL13, OPG+IL1beta+IL2, OPG+IL1beta+ TNFa, OPG+IL10+IL2, IL10+IL2+IL4, IL1beta+IL10+IL4, IL1beta+IL10+IL13, IL1beta+IL10+TNFa, OPG+IL2+ TNFa, IL1beta+IL2+IL4, OPG+IL1beta+IL10, IL10+IL2+ TNFa, IL1beta+IL10+IL2, IL10+IL13+TNFa, IL1beta+ IL13+TNFa, OPG+IL13+TNFa, IL1beta+IL2+IL13, OPG+ IL2+IL13, IL2+IL13+TNFa, T.denticola+P.intermedia, T.denticola+C.rectus, T.forsythia+T.denticola, P.gingivalis+ P.intermedia, T.forsythia+P.intermedia, P.gingivalis+T.denticola, T.denticola+F.nucleatum, P.gingivalis+T.forsythia, T.forsythia+F.nucleatum, T.forsythia+C.rectus, P.gingivalis+ F.nucleatum, P.gingivalis+C.rectus, P.intermedia+F.nucleatum, P.intermedia+C.rectus, F.nucleatum+C.rectus, T.forsythia+T.denticola+P.intermedia, P.gingivalis+T.denticola+ P.intermedia, T.denticola+P.intermedia+C.rectus, T.denticola+P.intermedia+F.nucleatum, T.forsythia+T.denticola+C.rectus, P.gingivalis+T.forsythia+P.intermedia, P.gingivalis+T.denticola+C.rectus, T.forsythia+P.intermedia+ F.nucleatum, P.gingivalis+P.intermedia+F.nucleatum, T.denticola+F.nucleatum+C.rectus, T.forsythia+T.denticola+ F.nucleatum, T.forsythia+P.intermedia+C.rectus, P.gingivalis+T.forsythia+C.rectus, P.gingivalis+P.intermedia+C.rectus, P.gingivalis+T.forsythia+T.denticola, P.gingivalis+ T.forsythia+F.nucleatum, P.gingivalis+T.denticola+ F.nucleatum, T.forsythia+F.nucleatum+C.rectus, P.gingivalis+F.nucleatum+C.rectus, P.intermedia+F.nucleatum+C.rectus, T.denticola+ICTP, MMP8+T.denticola, MMP9+T.denticola, MMP8+P.gingivalis, MMP9+P.gingivalis, MMP8+T.forsythia, MMP9+T.forsythia, Calprotectin+ T.denticola, T.denticola+IL6, OPG+T.denticola, Calprotectin+T.forsythia, T.denticola+IL13, T.denticola+IL10, T.forsythia+ICTP, T.forsythia+IL13, Calprotectin+P.gingivalis, T.denticola+IL2, P.gingivalis+IL6, P.gingivalis+ICTP, T.denticola+IL4, T.denticola+TNFa, T.forsythia+IL6, T.denticola+IL1beta, OPG+T.forsythia, T.forsythia+TNFa, T.forsythia+IL1beta, T.forsythia+IL4, P.gingivalis+IL10, OPG+ P.gingivalis, MMP8+P.intermedia, T.forsythia+IL10, P.gingivalis+IL2, T.forsythia+IL2, P.gingivalis+IL1beta, P.gingivalis+IL4, P.gingivalis+IL13, MMP9+P.intermedia, P.gingivalis+TNFa, Calprotectin+P.intermedia, ICTP+P.intermedia, MMP9+C.rectus, TNFa+P.intermedia, MMP8+ C.rectus, IL4+P.intermedia, IL13+P.intermedia, IL1beta+ P.intermedia, IL6+P.intermedia, OPG+P.intermedia, IL2+ P.intermedia, IL10+P.intermedia, MMP9+F.nucleatum, MMP8+F.nucleatum, Calprotectin+C.rectus, IL6+C.rectus, Calprotectin+F.nucleatum, ICTP+C.rectus, IL4+C.rectus, IL10+C.rectus, IL1beta+C.rectus, IL6+F.nucleatum, ICTP+ F.nucleatum, OPG+C.rectus, IL2+C.rectus, IL13+C.rectus, IL4+F.nucleatum, TNFa+C.rectus, IL10+F.nucleatum, OPG+F.nucleatum, IL1beta+F.nucleatum, TNFa+F.nucleatum, IL2+F.nucleatum, IL13+F.nucleatum, T.denticola+ ICTP+C.rectus, T.denticola+ICTP+P.intermedia, MMP8+ T.denticola+P.intermedia, T.forsythia+T.denticola+ICTP, MMP9+T.denticola+P.intermedia, MMP8+T.denticola+ C.rectus, MMP9+T.denticola+C.rectus, MMP8+P.gingivalis+P.intermedia, Calprotectin+T.denticola+P.intermedia, P.gingivalis+T.denticola+ICTP, Calprotectin+T.denticola+ C.rectus, T.denticola+IL13+P.intermedia, MMP8+T.forsythia+T.denticola, MMP8+T.forsythia+P.intermedia, MMP9+T.forsythia+T.denticola, T.denticola+ICTP+F.nucleatum, MMP8+P.gingivalis+T.denticola, MMP9+P.gingivalis+T.denticola, Calprotectin+P.gingivalis+P.intermedia, MMP9+P.gingivalis+P.intermedia, OPG+T.denticola+P.intermedia, T.denticola+TNFa+P.intermedia, T.denticola+ IL4+P.intermedia, Calprotectin+T.forsythia+P.intermedia, MMP9+T.forsythia+P.intermedia, T.denticola+IL6+P.intermedia, T.denticola+IL6+C.rectus, T.denticola+IL1beta+ P.intermedia, MMP8+T.denticola+F.nucleatum, MMP9+ T.denticola+F.nucleatum, T.denticola+IL2+P.intermedia, T.denticola+IL10+C.rectus, T.denticola+IL10+P.intermedia, T.forsythia+IL13+P.intermedia, OPG+T.denticola+ C.rectus, OPG+T.forsythia+T.denticola, T.forsythia+T.denticola+IL13, Calprotectin+T.forsythia+T.denticola, P.gingivalis+ICTP+P.intermedia, T.denticola+IL2+C.rectus, MMP8+P.gingivalis+T.forsythia, MMP9+P.gingivalis+ T.forsythia, T.forsythia+ICTP+P.intermedia, T.denticola+ IL13+C.rectus, MMP9+T.forsythia+C.rectus, T.forsythia+ TNFa+P.intermedia, T.denticola+IL4+C.rectus, T.denticola+TNFa+C.rectus, T.forsythia+T.denticola+TNFa, T.denticola+IL1beta+C.rectus, T.forsythia+T.denticola+ IL1beta, OPG+P.gingivalis+T.denticola, MMP8+T.forsythia+C.rectus, T.forsythia+T.denticola+IL6, P.gingivalis+ IL13+P.intermedia, T.forsythia+T.denticola+IL4, T.forsythia+IL10+P.intermedia, MMP9+T.forsythia+F.nucleatum, Calprotectin+T.forsythia+C.rectus, P.gingivalis+ IL6+P.intermedia, MMP8+T.forsythia+F.nucleatum, T.forsythia+IL1beta+P.intermedia, T.forsythia+T.denticola+ IL10, T.forsythia+T.denticola+IL2, OPG+T.forsythia+ P.intermedia, MMP9+P.gingivalis+C.rectus, T.forsythia+ IL4+P.intermedia, MMP9+P.gingivalis+F.nucleatum, OPG+ P.gingivalis+P.intermedia, T.forsythia+IL6+P.intermedia, Calprotectin+T.denticola+F.nucleatum, P.gingivalis+T.denticola+IL13, P.gingivalis+IL1beta+P.intermedia, P.gingivalis+TNFa+P.intermedia, Calprotectin+P.gingivalis+T.denticola, MMP8+P.gingivalis+F.nucleatum, P.gingivalis+IL2+ P.intermedia, MMP8+P.gingivalis+C.rectus, Calprotectin+ T.forsythia+F.nucleatum, P.gingivalis+IL4+P.intermedia, T.forsythia+IL2+P.intermedia, P.gingivalis+T.forsythia+ IL6, P.gingivalis+T.denticola+IL6, P.gingivalis+IL10+P.intermedia, P.gingivalis+T.denticola+IL10, P.gingivalis+ T.denticola+IL2, Calprotectin+P.gingivalis+T.forsythia, OPG+T.denticola+F.nucleatum, P.gingivalis+T.forsythia+ ICTP, T.forsythia+ICTP+F.nucleatum, P.gingivalis+T.denticola+IL4, T.denticola+IL6+F.nucleatum, T.forsythia+ICTP+ C.rectus, T.denticola+IL2+F.nucleatum, Calprotectin+ P.gingivalis+C.rectus, P.gingivalis+T.denticola+TNFa, OPG+P.gingivalis+T.forsythia, P.gingivalis+T.forsythia+ IL13, T.denticola+IL13+F.nucleatum, T.denticola+IL10+ F.nucleatum, Calprotectin+P.gingivalis+F.nucleatum, P.gingivalis+T.forsythia+IL10, P.gingivalis+T.denticola+IL1beta, T.forsythia+IL6+C.rectus, T.forsythia+IL13+F.nucleatum, T.forsythia+IL13+C.rectus, T.forsythia+IL6+F.nucleatum, T.denticola+IL4+F.nucleatum, OPG+T.forsythia+F.nucleatum, T.forsythia+TNFa+F.nucleatum, P.gingivalis+IL6+F.nucleatum, T.denticola+IL1beta+F.nucleatum, OPG+T.forsythia+C.rectus, T.denticola+TNFa+F.nucleatum, T.forsythia+IL1beta+F.nucleatum, P.gingivalis+T.forsythia+IL2, T.forsythia+IL1beta+C.rectus, P.gingivalis+ICTP+F.nucleatum, T.forsythia+IL4+F.nucleatum, T.forsythia+TNFa+C.rectus, P.gingivalis+T.forsythia+IL4, P.gingivalis+IL6+C.rectus, T.forsythia+IL4+C.rectus, T.forsythia+IL2+F.nucleatum, P.gingivalis+T.forsythia+TNFa, T.forsythia+IL10+F.nucleatum, T.forsythia+IL10+C.rectus, P.gingivalis+ICTP+C.rectus, T.forsythia+IL2+C.rectus, P.gingivalis+T.forsythia+IL1beta, P.gingivalis+IL10+F.nucleatum, OPG+P.gingivalis+F.nucleatum, P.gingivalis+IL4+F.nucleatum, P.gingivalis+IL2+F.nucleatum, P.gingivalis+IL1beta+F.nucleatum, P.gingivalis+TNFa+F.nucleatum, P.gingivalis+IL13+F.nucleatum, OPG+P.gingivalis+C.rectus, MMP8+P.intermedia+F.nucleatum, P.gingivalis+IL10+C.rectus, P.gingivalis+IL2+C.rectus, MMP8+P.intermedia+C.rectus, P.gingivalis+IL4+C.rectus, P.gingivalis+TNFa+C.rectus, P.gingivalis+IL1beta+C.rectus, P.gingivalis+IL13+C.rectus, Calprotectin+P.intermedia+F.nucleatum, MMP9+P.intermedia+F.nucleatum, MMP9+P.intermedia+C.rectus, Calprotectin+P.intermedia+C.rectus, ICTP+P.intermedia+F.nucleatum, TNFa+P.intermedia+F.nucleatum, IL4+P.intermedia+F.nucleatum, ICTP+P.intermedia+C.rectus, IL10+P.intermedia+F.nucleatum, IL1beta+P.intermedia+F.nucleatum, IL6+P.intermedia+F.nucleatum, OPG+P.intermedia+F.nucleatum, IL2+P.intermedia+F.nucleatum, IL13+P.intermedia+F.nucleatum, MMP9+F.nucleatum+C.rectus, TNFa+P.intermedia+C.rectus, MMP8+F.nucleatum+C.rectus, IL4+P.intermedia+C.rectus, Calprotectin+F.nucleatum+C.rectus, IL6+P.intermedia+C.rectus, IL10+P.intermedia+C.rectus, IL1beta+P.intermedia+C.rectus, IL13+P.intermedia+C.rectus, IL2+P.intermedia+C.rectus, OPG+P.intermedia+C.rectus, ICTP+F.nucleatum+C.rectus, IL6+F.nucleatum+C.rectus, IL4+F.nucleatum+C.rectus, IL10+F.nucleatum+C.rectus, IL13+F.nucleatum+C.rectus, IL1beta+F.nucleatum+C.rectus, TNFa+F.nucleatum+C.rectus, OPG+F.nucleatum+C.rectus, IL2+F.nucleatum+C.rectus, MMP8+T.denticola+ICTP, MMP9+T.denticola+ICTP, T.denticola+IL6+ICTP, Calprotectin+T.denticola+ICTP, T.denticola+ICTP+IL10, MMP8+OPG+T.denticola, MMP8+T.denticola+IL1beta, OPG+T.denticola+ICTP, Calprotectin+MMP9+P.gingivalis, MMP9+OPG+T.denticola, Calprotectin+MMP9+T.denticola, MMP9+T.denticola+IL1beta, T.denticola+ICTP+IL13, T.denticola+ICTP+IL2, MMP8+Calprotectin+T.denticola, T.denticola+ICTP+TNFa, MMP8+T.denticola+IL2, MMP9+T.denticola+TNFa, MMP8+Calprotectin+P.gingivalis, MMP8+T.denticola+IL10, MMP8+T.denticola+TNFa, MMP8+T.denticola+IL13, Calprotectin+MMP9+T.forsythia, MMP9+T.denticola+IL13, T.denticola+ICTP+IL4, MMP8+P.gingivalis+ICTP, MMP9+T.denticola+IL6, MMP9+T.denticola+IL2, T.denticola+ICTP+IL1beta, MMP8+MMP9+T.denticola, MMP9+T.denticola+IL10, MMP8+T.denticola+IL6, MMP8+T.denticola+IL4, MMP9+T.denticola+IL4, MMP8+T.forsythia+ICTP, MMP9+P.gingivalis+ICTP, MMP8+T.forsythia+IL1beta, MMP9+T.forsythia+ICTP, MMP8+Calprotectin+T.forsythia, MMP8+OPG+T.forsythia, MMP9+OPG+T.forsythia, MMP9+T.forsythia+IL1beta, MMP9+T.forsythia+TNFa, MMP9+T.forsythia+IL13, MMP8+T.forsythia+IL13, MMP8+T.forsythia+TNFa, MMP9+OPG+P.gingivalis, MMP9+P.gingivalis+IL1beta, MMP9+P.gingivalis+IL6, MMP8+OPG+P.gingivalis, MMP8+P.gingivalis+IL6, MMP8+P.gingivalis+IL10, MMP8+P.gingivalis+IL1beta, MMP8+T.forsythia+IL4, MMP9+T.forsythia+IL4, Calprotectin+OPG+T.denticola, MMP9+P.gingivalis+TNFa, MMP8+P.gingivalis+TNFa, MMP8+MMP9+P.gingivalis, MMP9+P.gingivalis+IL13, MMP9+P.gingivalis+IL10, MMP8+P.gingivalis+IL4, MMP9+P.gingivalis+IL4, MMP9+T.forsythia+IL2, MMP9+T.forsythia+IL10, MMP8+P.gingivalis+IL13, MMP8+MMP9+T.forsythia, Calprotectin+T.denticola+IL6, MMP9+T.forsythia+IL6, MMP8+T.forsythia+IL6, Calprotectin+OPG+T.forsythia, Calprotectin+T.forsythia+ICTP, Calprotectin+T.forsythia+IL13, MMP8+T.forsythia+IL2, MMP8+T.forsythia+IL10, T.denticola+IL6+IL13, MMP8+P.gingivalis+IL2, Calprotectin+T.denticola+IL13, OPG+T.denticola+IL6, Calprotectin+T.forsythia+IL6, T.forsythia+IL6+IL13, Calprotectin+T.denticola+IL10, Calprotectin+P.gingivalis+IL6, Calprotectin+T.denticola+IL2, MMP9+P.gingivalis+IL2, T.forsythia+ICTP+IL13, T.denticola+IL10+IL13, Calprotectin+P.gingivalis+ICTP, P.gingivalis+IL6+ICTP, OPG+T.denticola+IL13, Calprotectin+T.denticola+IL4, OPG+T.denticola+IL10, Calprotectin+T.denticola+TNFa, T.denticola+IL6+IL2, T.forsythia+IL6+ICTP, Calprotectin+OPG+P.gingivalis, T.denticola+IL6+TNFa, Calprotectin+T.denticola+IL1beta, OPG+T.denticola+TNFa, Calprotectin+T.forsythia+TNFa, T.denticola+IL6+IL1beta, T.denticola+IL6+IL4, Calprotectin+T.forsythia+IL1beta, OPG+T.denticola+IL2, OPG+T.denticola+IL1beta, T.forsythia+ICTP+TNFa, T.denticola+IL2+IL13, T.denticola+IL6+IL10, T.denticola+IL1beta+IL13, Calprotectin+P.gingivalis+IL10, OPG+T.forsythia+ICTP, Calprotectin+T.forsythia+IL4, OPG+T.denticola+IL4, T.forsythia+IL10+IL13, T.denticola+IL13+IL4, Calprotectin+T.forsythia+IL10, Calprotectin+P.gingivalis+IL2, P.gingivalis+IL6+IL13, T.denticola+IL10+IL2, OPG+T.forsythia+IL13, T.forsythia+ICTP+IL1beta, T.denticola+IL2+TNFa, Calprotectin+T.forsythia+IL2, Calprotectin+P.gingivalis+IL13, T.denticola+IL10+TNFa, T.denticola+IL13+TNFa, Calprotectin+P.gingivalis+IL1beta, Calprotectin+P.gingivalis+IL4, T.forsythia+IL13+TNFa, T.forsythia+ICTP+IL4, P.gingivalis+ICTP+IL10, T.forsythia+IL13+IL4, T.forsythia+IL2+IL13, OPG+P.gingivalis+IL6, T.forsythia+ICTP+IL10, T.denticola+IL1beta+IL10, T.denticola+IL10+IL4, Calprotectin+P.gingivalis+TNFa, T.forsythia+IL6+TNFa, T.forsythia+ICTP+IL2, T.forsythia+IL1beta+IL13, T.denticola+IL2+IL4, T.denticola+IL1beta+IL2, OPG+T.forsythia+IL6, P.gingivalis+ICTP+IL1beta, P.gingivalis+IL6+TNFa, T.forsythia+IL6+IL1beta, P.gingivalis+IL6+IL2, P.gingivalis+ICTP+IL4, P.gingivalis+ICTP+IL2, MMP8+Calprotectin+P.intermedia, T.forsythia+IL6+IL10, OPG+P.gingivalis+ICTP, P.gingivalis+IL6+IL10, T.forsythia+IL6+IL4, P.gingivalis+IL6+IL1beta, T.denticola+IL4+TNFa, OPG+T.forsythia+TNFa, Calprotectin+MMP9+P.intermedia, P.gingivalis+IL6+IL4, MMP8+ICTP+P.intermedia, P.gingivalis+ICTP+IL13, P.gingivalis+ICTP+TNFa, T.forsythia+IL6+IL2, T.denticola+IL1beta+IL4, MMP8+TNFa+P.intermedia, OPG+T.forsythia+IL1beta, OPG+T.forsythia+IL4, T.denticola+IL1beta+TNFa, OPG+T.forsythia+IL10, OPG+T.forsythia+IL2, MMP9+TNFa+P.intermedia, T.forsythia+IL2+TNFa, T.forsythia+IL4+TNFa, T.forsythia+IL1beta+TNFa, P.gingivalis+IL10+IL13, MMP8+IL1beta+P.intermedia, OPG+P.gingivalis+IL10, T.forsythia+IL10+TNFa, MMP8+IL6+P.intermedia, OPG+P.gingivalis+IL1beta, MMP8+OPG+P.intermedia, OPG+P.gingivalis+IL4, P.gingivalis+IL10+IL2, T.forsythia+IL1beta+IL4, OPG+P.gingivalis+IL2, T.forsythia+IL2+IL4, T.forsythia+IL1beta+IL10, MMP9+

ICTP+*P.intermedia*, *P.gingivalis*+IL1beta+IL10, *P.gingivalis*+IL2+IL13, *T.forsythia*+IL1beta+IL2, OPG+*P.gingivalis*+TNFa, MMP8+MMP9+*P.intermedia*, *P.gingivalis*+IL1beta+IL2, *P.gingivalis*+IL10+IL4, *T.forsythia*+IL10+IL4, OPG+*P.gingivalis*+IL13, MMP8+IL13+*P.intermedia*, *P.gingivalis*+IL10+TNFa, *P.gingivalis*+IL13+TNFa, *P.gingivalis*+IL13+IL4, MMP8+IL4+*P.intermedia*, MMP8+IL10+*P.intermedia*, *P.gingivalis*+IL2+IL4, *P.gingivalis*+IL2+TNFa, *T.forsythia*+IL10+IL2, MMP8+IL2+*P.intermedia*, MMP9+IL1beta+*P.intermedia*, *P.gingivalis*+IL1beta+IL4, Calprotectin+TNFa+*P.intermedia*, MMP9+IL2+*P.intermedia*, *P.gingivalis*+IL1beta+IL13, MMP9+IL6+*P.intermedia*, Calprotectin+MMP9+*C.rectus*, *P.gingivalis*+IL1beta+TNFa, MMP9+OPG+*P.intermedia*, *P.gingivalis*+IL4+TNFa, Calprotectin+ICTP+*P.intermedia*, Calprotectin+OPG+*P.intermedia*, MMP9+IL13+*P.intermedia*, Calprotectin+IL13+*P.intermedia*, MMP9+IL10+*P.intermedia*, Calprotectin+IL2+*P.intermedia*, MMP8+Calprotectin+*C.rectus*, Calprotectin+IL6+*P.intermedia*, Calprotectin+IL1beta+*P.intermedia*, MMP9+IL4+*P.intermedia*, Calprotectin+IL10+*P.intermedia*, Calprotectin+IL4+*P.intermedia*, MMP8+ICTP+*C.rectus*, MMP9+ICTP+*C.rectus*, ICTP+TNFa+*P.intermedia*, MMP9+TNFa+*C.rectus*, Calprotectin+MMP9+*F.nucleatum*, MMP9+IL6+*C.rectus*, IL4+TNFa+*P.intermedia*, IL6+ICTP+*P.intermedia*, MMP8+MMP9+*C.rectus*, ICTP+IL4+*P.intermedia*, ICTP+IL1beta+*P.intermedia*, MMP8+TNFa+*C.rectus*, MMP9+OPG+*C.rectus*, MMP9+IL1beta+*C.rectus*, IL1beta+TNFa+*P.intermedia*, MMP9+IL10+*C.rectus*, ICTP+IL13+*P.intermedia*, IL6+TNFa+*P.intermedia*, MMP8+IL10+*C.rectus*, IL2+TNFa+*P.intermedia*, MMP9+IL2+*C.rectus*, ICTP+IL2+*P.intermedia*, MMP9+IL13+*C.rectus*, MMP9+IL4+*C.rectus*, ICTP+IL10+*P.intermedia*, IL10+TNFa+*P.intermedia*, Calprotectin+OPG+*C.rectus*, MMP8+ICTP+*F.nucleatum*, OPG+ICTP+*P.intermedia*, MMP8+IL6+*C.rectus*, MMP8+IL1beta+*C.rectus*, MMP8+Calprotectin+*F.nucleatum*, MMP8+IL13+*C.rectus*, MMP8+IL4+*C.rectus*, OPG+TNFa+*P.intermedia*, MMP8+OPG+*C.rectus*, IL13+TNFa+*P.intermedia*, MMP8+IL2+*C.rectus*, Calprotectin+IL6+*C.rectus*, IL13+IL4+*P.intermedia*, MMP9+TNFa+*F.nucleatum*, IL1beta+IL13+*P.intermedia*, IL6+IL13+*P.intermedia*, MMP8+TNFa+*F.nucleatum*, MMP9+ICTP+*F.nucleatum*, Calprotectin+IL10+*C.rectus*, IL6+IL4+*P.intermedia*, IL6+IL1beta+*P.intermedia*, IL10+IL13+*P.intermedia*, OPG+IL4+*P.intermedia*, IL10+IL4+*P.intermedia*, IL1beta+IL4+*P.intermedia*, Calprotectin+ICTP+*C.rectus*, IL2+IL13+*P.intermedia*, OPG+IL1beta+*P.intermedia*, MMP8+IL10+*F.nucleatum*, OPG+IL13+*P.intermedia*, MMP9+IL10+*F.nucleatum*, IL1beta+IL10+*P.intermedia*, IL2+IL4+*P.intermedia*, MMP8+OPG+*F.nucleatum*, MMP8+IL1beta+*F.nucleatum*, IL1beta+IL2+*P.intermedia*, MMP8+IL4+*F.nucleatum*, MMP9+IL1beta+*F.nucleatum*, OPG+IL2+*P.intermedia*, IL6+IL2+*P.intermedia*, MMP9+IL4+*F.nucleatum*, OPG+IL10+*P.intermedia*, Calprotectin+IL1beta+*C.rectus*, MMP8+IL2+*F.nucleatum*, Calprotectin+IL4+*C.rectus*, MMP8+IL6+*F.nucleatum*, MMP9+OPG+*F.nucleatum*, OPG+IL6+*P.intermedia*, IL10+IL2+*P.intermedia*, IL6+IL10+*P.intermedia*, MMP8+MMP9+*F.nucleatum*, MMP8+IL13+*F.nucleatum*, MMP9+IL6+*F.nucleatum*, MMP9+IL13+*F.nucleatum*, MMP9+IL2+*F.nucleatum*, IL6+ICTP+*C.rectus*, Calprotectin+OPG+*F.nucleatum*, Calprotectin+IL13+*C.rectus*, Calprotectin+TNFa+*C.rectus*, Calprotectin+IL2+*C.rectus*, Calprotectin+IL6+*F.nucleatum*, Calprotectin+ICTP+*F.nucleatum*, IL6+IL4+*C.rectus*, Calprotectin+TNFa+*F.nucleatum*, ICTP+IL1beta+*C.rectus*, Calprotectin+IL10+*F.nucleatum*, IL6+ICTP+*F.nucleatum*, ICTP+IL4+*C.rectus*, Calprotectin+IL4+*F.nucleatum*, IL6+IL13+*C.rectus*, IL6+TNFa+*C.rectus*, IL6+IL1beta+*C.rectus*, IL4+TNFa+*C.rectus*, Calprotectin+IL2+*F.nucleatum*, OPG+IL6+*C.rectus*, IL4+TNFa+*F.nucleatum*, ICTP+IL10+*C.rectus*, IL6+IL2+*C.rectus*, IL6+IL10+*C.rectus*, ICTP+IL13+*C.rectus*, Calprotectin+IL13+*F.nucleatum*, ICTP+TNFa+*C.rectus*, ICTP+IL2+*C.rectus*, OPG+ICTP+*C.rectus*, IL6+TNFa+*F.nucleatum*, Calprotectin+IL1beta+*F.nucleatum*, ICTP+IL4+*F.nucleatum*, IL10+IL4+*C.rectus*, ICTP+IL10+*F.nucleatum*, OPG+IL6+*F.nucleatum*, OPG+IL4+*C.rectus*, IL13+IL4+*C.rectus*, IL6+IL10+*F.nucleatum*, IL2+IL4+*C.rectus*, IL1beta+IL4+*C.rectus*, OPG+IL10+*C.rectus*, IL1beta+IL10+*C.rectus*, IL10+TNFa+*C.rectus*, ICTP+IL1beta+*F.nucleatum*, ICTP+TNFa+*F.nucleatum*, OPG+IL1beta+*C.rectus*, IL1beta+TNFa+*C.rectus*, IL10+IL2+*C.rectus*, IL10+IL13+*C.rectus*, IL6+IL13+*F.nucleatum*, IL6+IL4+*F.nucleatum*, OPG+ICTP+*F.nucleatum*, IL1beta+IL2+*C.rectus*, IL6+IL1beta+*F.nucleatum*, IL1beta+IL13+*C.rectus*, IL10+TNFa+*C.rectus*, OPG+TNFa+*C.rectus*, ICTP+IL13+*F.nucleatum*, IL13+IL4+*F.nucleatum*, OPG+IL4+*F.nucleatum*, IL2+TNFa+*C.rectus*, IL13+TNFa+*C.rectus*, ICTP+IL2+*F.nucleatum*, OPG+IL10+*F.nucleatum*, IL10+IL4+*F.nucleatum*, IL2+IL13+*C.rectus*, OPG+IL13+*C.rectus*, OPG+IL2+*C.rectus*, IL6+IL2+*F.nucleatum*, IL10+IL13+*F.nucleatum*, IL2+IL4+*F.nucleatum*, IL1beta+IL4+*F.nucleatum*, IL1beta+IL10+*F.nucleatum*, IL1beta+TNFa+*F.nucleatum*, OPG+TNFa+*F.nucleatum*, IL10+IL2+*F.nucleatum*, OPG+IL1beta+*F.nucleatum*, OPG+IL13+*F.nucleatum*, OPG+IL2+*F.nucleatum*, IL1beta+IL13+*F.nucleatum*, IL1beta+IL2+*F.nucleatum*, IL2+TNFa+*F.nucleatum*, IL13+TNFa+*F.nucleatum*, IL2+IL13+*F.nucleatum*, MMP8+*T.denticola*+ICTP+*C.rectus*, MMP8+*T.denticola*+ICTP+*P.intermedia*, MMP9+*T.denticola*+ICTP+*C.rectus*, Calprotectin+*T.denticola*+ICTP+*C.rectus*, *T.denticola*+IL6+ICTP+*C.rectus*, MMP8+*T.forsythia*+*T.denticola*+ICTP, MMP9+*T.denticola*+ICTP+*P.intermedia*, MMP8+*P.gingivalis*+*T.denticola*+ICTP, MMP8+*T.denticola*+IL1beta+*P.intermedia*, MMP9+*T.forsythia*+*T.denticola*+ICTP, MMP8+Calprotectin+*P.gingivalis*+*P.intermedia*, Calprotectin+MMP9+*T.denticola*+*C.rectus*, *T.denticola*+ICTP+IL10+*C.rectus*, *T.forsythia*+*T.denticola*+ICTP+IL13, MMP8+*T.denticola*+TNFa+*P.intermedia*, MMP8+Calprotectin+*T.denticola*+*P.intermedia*, MMP9+*P.gingivalis*+*T.denticola*+ICTP, Calprotectin+MMP9+*P.gingivalis*+*P.intermedia*, Calprotectin+*T.denticola*+ICTP+*P.intermedia*, *T.denticola*+ICTP+TNFa+*P.intermedia*, MMP8+*T.denticola*+ICTP+*F.nucleatum*, MMP8+OPG+*T.denticola*+*P.intermedia*, MMP8+*T.denticola*+IL13+*P.intermedia*, *T.denticola*+ICTP+IL13+*P.intermedia*, *T.forsythia*+*T.denticola*+IL6+ICTP, *T.denticola*+ICTP+IL2+*C.rectus*, MMP8+*T.denticola*+IL4+*P.intermedia*, *T.denticola*+IL6+ICTP+*P.intermedia*, MMP9+*T.denticola*+TNFa+*P.intermedia*, *T.denticola*+ICTP+IL1beta+*C.rectus*, Calprotectin+MMP9+*T.denticola*+*P.intermedia*, *T.denticola*+ICTP+IL1beta+*P.intermedia*, OPG+*T.denticola*+ICTP+*C.rectus*, *T.denticola*+ICTP+IL4+*C.rectus*, MMP8+*P.gingivalis*+ICTP+*P.intermedia*, MMP8+*T.forsythia*+IL1beta+*P.intermedia*, *T.denticola*+ICTP+IL4+*P.intermedia*, *T.denticola*+ICTP+IL13+*C.rectus*, MMP9+*T.denticola*+IL1beta+*P.intermedia*, OPG+*T.denticola*+ICTP+*P.intermedia*, OPG+*T.forsythia*+*T.denticola*+ICTP, MMP8+Calprotectin+*T.denticola*+*C.rectus*, MMP8+OPG+*T.denticola*+*C.rectus*, MMP9+*T.denticola*+IL13+*P.intermedia*, *T.denticola*+ICTP+IL10+*P.intermedia*, *T.denticola*+ICTP+TNFa+*C.rectus*, MMP8+Calprotectin+*T.forsythia*+*P.intermedia*, MMP8+*T.denticola*+IL6+*P.intermedia*, MMP9+*T.denticola*+IL1beta+*C.rectus*, *P.gingivalis*+*T.denticola*+IL6+ICTP, MMP8+*T.denticola*+IL1beta+*C.rectus*, *T.denticola*+ICTP+ IL2+*P.intermedia*, MMP8+*P.gingivalis*+IL1beta+*P.intermedia*, MMP8+*T.forsythia*+*T.denticola*+IL1beta, *T.forsythia*+ *T.denticola*+ICTP+TNFa, MMP8+*T.forsythia*+TNFa+ *P.intermedia*, MMP9+OPG+*T.denticola*+*C.rectus*, *T.forsythia*+*T.denticola*+ICTP+IL1beta, Calprotectin+*T.forsythia*+*T.denticola*+ICTP, MMP8+MMP9+*T.denticola*+*P.intermedia*, MMP8+*T.denticola*+IL2+*P.intermedia*, MMP9+ *T.denticola*+ICTP+*F.nucleatum*, Calprotectin+MMP9+ *T.forsythia*+*P.intermedia*, MMP9+OPG+*T.denticola*+ *P.intermedia*, MMP9+*T.denticola*+IL4+*P.intermedia*, *T.forsythia*+*T.denticola*+ICTP+IL10, MMP8+*T.forsythia*+ ICTP+*P.intermedia*, *T.forsythia*+*T.denticola*+ICTP+IL4, MMP8+*P.gingivalis*+TNFa+*P.intermedia*, Calprotectin+ MMP9+*P.gingivalis*+*T.denticola*, Calprotectin+OPG+ *T.denticola*+*C.rectus*, *T.forsythia*+*T.denticola*+ICTP+IL2, MMP8+*T.denticola*+IL10+*P.intermedia*, MMP9+*T.forsythia*+*T.denticola*+IL1beta, MMP8+*T.forsythia*+IL13+*P.intermedia*, Calprotectin+MMP9+*T.forsythia*+*T.denticola*, Calprotectin+*T.denticola*+IL6+*C.rectus*, MMP9+*T.denticola*+TNFa+*C.rectus*, MMP8+Calprotectin+*T.forsythia*+ *T.denticola*, Calprotectin+*T.denticola*+IL13+*P.intermedia*, MMP8+MMP9+*T.denticola*+*C.rectus*, MMP8+OPG+*T.forsythia*+*T.denticola*, Calprotectin+*T.denticola*+TNFa+*P.intermedia*, MMP8+*P.gingivalis*+*T.denticola*+IL1beta, MMP8+*T.forsythia*+*T.denticola*+IL13, MMP9+*T.forsythia*+ *T.denticola*+IL13, MMP9+*T.forsythia*+TNFa+*P.intermedia*, MMP9+*T.denticola*+IL6+*C.rectus*, OPG+*P.gingivalis*+ *T.denticola*+ICTP, Calprotectin+OPG+*T.denticola*+*P.intermedia*, *P.gingivalis*+*T.denticola*+ICTP+IL10, MMP8+*P.gingivalis*+IL13+*P.intermedia*, MMP8+*P.gingivalis*+IL4+ *P.intermedia*, MMP8+*T.denticola*+IL4+*C.rectus*, MMP8+ *T.denticola*+TNFa+*C.rectus*, MMP9+OPG+*T.forsythia*+ *T.denticola*, MMP9+*T.denticola*+IL6+*P.intermedia*, MMP9+*T.denticola*+IL2+*P.intermedia*, MMP8+Calprotectin+*P.gingivalis*+*T.denticola*, MMP9+*P.gingivalis*+ICTP+ *P.intermedia*, MMP9+*T.forsythia*+*T.denticola*+TNFa, MMP8+*T.forsythia*+IL4+*P.intermedia*, MMP9+*P.gingivalis*+*T.denticola*+IL13, MMP9+*T.denticola*+IL4+*C.rectus*, *T.denticola*+IL6+ICTP+*F.nucleatum*, MMP8+*T.forsythia*+ *T.denticola*+TNFa, MMP8+*T.denticola*+IL10+*C.rectus*, Calprotectin+*P.gingivalis*+*T.denticola*+ICTP, Calprotectin+ *T.denticola*+ICTP+*F.nucleatum*, Calprotectin+*T.denticola*+ IL4+*P.intermedia*, *P.gingivalis*+*T.denticola*+ICTP+IL13, MMP8+*P.gingivalis*+*T.denticola*+IL13, Calprotectin+*P.gingivalis*+ICTP+*P.intermedia*, MMP9+*T.denticola*+IL10+ *C.rectus*, MMP9+*P.gingivalis*+IL1beta+*P.intermedia*, MMP8+OPG+*P.gingivalis*+*T.denticola*, MMP8+*T.denticola*+IL6+*C.rectus*, MMP9+OPG+*P.gingivalis*+*T.denticola*, MMP9+*P.gingivalis*+*T.denticola*+IL1beta, MMP9+*T.forsythia*+IL13+*P.intermedia*, MMP8+*T.denticola*+IL13+ *C.rectus*, Calprotectin+*T.denticola*+IL10+*C.rectus*, MMP8+ OPG+*T.forsythia*+*P.intermedia*, MMP8+*T.forsythia*+ *T.denticola*+IL4, MMP9+*T.forsythia*+*T.denticola*+IL4, MMP9+*T.denticola*+IL2+*C.rectus*, MMP9+*T.denticola*+ IL13+*C.rectus*, OPG+*T.denticola*+IL13+*P.intermedia*, MMP8+OPG+*P.gingivalis*+*P.intermedia*, MMP9+*T.forsythia*+IL1beta+*P.intermedia*, MMP9+*T.denticola*+IL10+ *P.intermedia*, MMP8+*T.denticola*+IL2+*C.rectus*, Calprotectin+*T.forsythia*+*T.denticola*+IL13, *P.gingivalis*+*T.denticola*+ ICTP+TNFa, MMP8+*P.gingivalis*+*T.denticola*+IL4, MMP8+*P.gingivalis*+IL2+*P.intermedia*, Calprotectin+ *T.denticola*+IL6+*P.intermedia*, Calprotectin+*T.denticola*+ IL1beta+*P.intermedia*, MMP9+*P.gingivalis*+*T.denticola*+ IL4, *P.gingivalis*+*T.denticola*+ICTP+IL2, *P.gingivalis*+ *T.denticola*+ICTP+IL4, *T.denticola*+IL2+IL13+ *P.intermedia*, OPG+*T.denticola*+ICTP+*F.nucleatum*, *T.denticola*+ICTP+IL10+*F.nucleatum*, *T.denticola*+ IL1beta+IL13+*P.intermedia*, MMP8+*T.forsythia*+IL10+ *P.intermedia*, *T.denticola*+ICTP+IL2+*F.nucleatum*, MMP8+ *T.forsythia*+IL6+*P.intermedia*, MMP9+*P.gingivalis*+ *T.denticola*+TNFa, MMP9+*P.gingivalis*+IL13+ *P.intermedia*, MMP9+*T.forsythia*+ICTP+*P.intermedia*, MMP8+MMP9+*P.gingivalis*+*T.denticola*, MMP8+*P.gingivalis*+IL6+*P.intermedia*, Calprotectin+*T.forsythia*+ICTP+ *P.intermedia*, Calprotectin+*T.forsythia*+IL13+*P.intermedia*, MMP9+*P.gingivalis*+IL4+*P.intermedia*, MMP9+*P.gingivalis*+TNFa+*P.intermedia*, *T.denticola*+IL10+IL13+*P.intermedia*, MMP8+*P.gingivalis*+*T.forsythia*+ICTP, MMP8+*P.gingivalis*+*T.denticola*+TNFa, Calprotectin+MMP9+ *T.forsythia*+*C.rectus*, Calprotectin+*T.denticola*+IL10+ *P.intermedia*, MMP8+*P.gingivalis*+*T.denticola*+IL2, MMP8+MMP9+*T.forsythia*+*T.denticola*, Calprotectin+ MMP9+*P.gingivalis*+*T.forsythia*, MMP9+*P.gingivalis*+ *T.forsythia*+ICTP, *P.gingivalis*+*T.denticola*+ICTP+IL1beta, *T.denticola*+IL6+IL13+*P.intermedia*, *T.denticola*+ICTP+ IL13+*F.nucleatum*, MMP8+Calprotectin+*T.denticola*+*F.nucleatum*, MMP8+*P.gingivalis*+IL10+*P.intermedia*, MMP8+ Calprotectin+*P.gingivalis*+*T.forsythia*, MMP8+OPG+ *T.denticola*+*F.nucleatum*, MMP8+*T.forsythia*+*T.denticola*+ IL2, Calprotectin+*T.denticola*+IL2+*P.intermedia*, Calprotectin+*T.denticola*+IL13+*C.rectus*, MMP9+*T.forsythia*+IL4+*P.intermedia*, *T.denticola*+IL13+IL4+*P.intermedia*, MMP8+*T.forsythia*+IL2+*P.intermedia*, Calprotectin+ MMP9+*T.denticola*+*F.nucleatum*, *T.denticola*+ICTP+ TNFa+*F.nucleatum*, *T.denticola*+IL13+TNFa+*P.intermedia*, Calprotectin+MMP9+*P.gingivalis*+*C.rectus*, MMP9+*T.forsythia*+*T.denticola*+IL10, MMP9+*T.forsythia*+IL2+*P.intermedia*, MMP8+MMP9+*P.gingivalis*+*P.intermedia*, Calprotectin+*T.denticola*+IL2+*C.rectus*, Calprotectin+*T.denticola*+ TNFa+*C.rectus*, OPG+*T.denticola*+IL4+*P.intermedia*, *T.denticola*+ICTP+IL4+*F.nucleatum*, *T.denticola*+ICTP+ IL1beta+*F.nucleatum*, MMP8+*P.gingivalis*+*T.denticola*+ IL10, Calprotectin+OPG+*P.gingivalis*+*P.intermedia*, Calprotectin+*P.gingivalis*+TNFa+*P.intermedia*, MMP9+ *T.forsythia*+*T.denticola*+IL6, MMP9+*T.forsythia*+IL10+ *P.intermedia*, Calprotectin+*T.denticola*+IL4+*C.rectus*, OPG+*T.denticola*+TNFa+*P.intermedia*, MMP8+*T.forsythia*+*T.denticola*+IL6, MMP8+*T.forsythia*+*T.denticola*+ IL10, MMP8+*T.forsythia*+ICTP+*C.rectus*, MMP8+*T.denticola*+IL1beta+*F.nucleatum*, Calprotectin+*P.gingivalis*+IL4+ *P.intermedia*, MMP9+*P.gingivalis*+*T.denticola*+IL6, Calprotectin+*P.gingivalis*+IL13+*P.intermedia*, MMP9+ OPG+*P.gingivalis*+*P.intermedia*, MMP9+*P.gingivalis*+IL2+ *P.intermedia*, *T.denticola*+IL6+TNFa+*P.intermedia*, *T.denticola*+IL2+TNFa+*P.intermedia*, MMP9+OPG+*T.denticola*+ *F.nucleatum*, OPG+*T.denticola*+IL6+*P.intermedia*, OPG+ *T.denticola*+IL1beta+*P.intermedia*, Calprotectin+OPG+ *T.forsythia*+*P.intermedia*, Calprotectin+*T.denticola*+ IL1beta+*C.rectus*, MMP9+OPG+*T.forsythia*+*P.intermedia*, MMP9+*P.gingivalis*+*T.forsythia*+IL13, *T.denticola*+IL10+ TNFa+*P.intermedia*, Calprotectin+OPG+*T.forsythia*+*C.rectus*, Calprotectin+*P.gingivalis*+IL10+*P.intermedia*, Calprotectin+*T.forsythia*+TNFa+*P.intermedia*, *T.denticola*+IL6+ IL4+*P.intermedia*, *T.denticola*+IL2+IL4+*P.intermedia*, MMP9+*P.gingivalis*+*T.denticola*+IL2, MMP9+*T.denticola*+ IL1beta+*F.nucleatum*, *T.forsythia*+*T.denticola*+IL6+IL13, Calprotectin+*P.gingivalis*+IL1beta+*P.intermedia*, MMP9+ *P.gingivalis*+*T.forsythia*+TNFa, *T.denticola*+IL6+IL13+ *C.rectus*, MMP8+*P.gingivalis*+*T.forsythia*+IL1beta, MMP8+*P.gingivalis*+*T.forsythia*+TNFa, *T.denticola*+IL6+ IL2+*P.intermedia*, *T.denticola*+IL10+IL4+*P.intermedia*, MMP8+MMP9+*T.forsythia*+*P.intermedia*, MMP9+*P.gingivalis*+*T.forsythia*+IL1beta, MMP9+*T.forsythia*+*T.denticola*+

IL2, MMP8+*P.gingivalis*+*T.forsythia*+IL4, MMP8+*P.gingivalis*+*T.denticola*+IL6, MMP8+*T.forsythia*+IL1beta+*C.rectus*, Calprotectin+*P.gingivalis*+IL2+*P.intermedia*, Calprotectin+*T.forsythia*+IL1beta+*P.intermedia*, MMP9+*P.gingivalis*+*T.forsythia*+IL4, MMP9+*P.gingivalis*+IL6+*P.intermedia*, MMP8+*P.gingivalis*+*T.forsythia*+IL13, Calprotectin+OPG+*T.forsythia*+*T.denticola*, MMP8+*T.forsythia*+IL1beta+*F.nucleatum*, MMP9+OPG+*P.gingivalis*+*T.forsythia*, MMP9+*P.gingivalis*+*T.denticola*+IL10, MMP9+*T.forsythia*+ICTP+*C.rectus*, MMP8+*P.gingivalis*+ICTP+*F.nucleatum*, Calprotectin+*P.gingivalis*+IL6+*P.intermedia*, Calprotectin+*T.forsythia*+IL4+*P.intermedia*, Calprotectin+MMP9+*T.forsythia*+*F.nucleatum*, Calprotectin+*T.forsythia*+IL10+*P.intermedia*, MMP9+*T.forsythia*+IL6+*P.intermedia*, OPG+*T.denticola*+IL6+*C.rectus*, *T.forsythia*+*T.denticola*+IL10+IL13, *T.forsythia*+ICTP+IL13+*P.intermedia*, *T.denticola*+IL6+IL1beta+*P.intermedia*, *T.denticola*+IL6+TNFa+*C.rectus*, *T.denticola*+IL1beta+TNFa+*P.intermedia*, *T.denticola*+IL4+TNFa+*P.intermedia*, Calprotectin+MMP9+*P.gingivalis*+*F.nucleatum*, MMP8+OPG+*P.gingivalis*+*T.forsythia*, MMP8+*T.denticola*+IL2+*F.nucleatum*, OPG+*T.denticola*+IL10+*P.intermedia*, *T.denticola*+IL1beta+IL2+*P.intermedia*, MMP9+*P.gingivalis*+IL10+*P.intermedia*, MMP9+*T.denticola*+IL10+*F.nucleatum*, OPG+*T.denticola*+IL2+*P.intermedia*, *T.denticola*+IL6+IL4+*C.rectus*, *T.denticola*+IL1beta+IL4+*P.intermedia*, MMP8+Calprotectin+*P.gingivalis*+*C.rectus*, MMP8+Calprotectin+*T.forsythia*+*F.nucleatum*, MMP8+*T.forsythia*+ICTP+*F.nucleatum*, MMP8+*T.denticola*+IL10+*F.nucleatum*, Calprotectin+*T.forsythia*+IL2+*P.intermedia*, MMP9+*T.forsythia*+IL1beta+*C.rectus*, OPG+*T.denticola*+IL10+*C.rectus*, MMP8+Calprotectin+*T.forsythia*+*C.rectus*, Calprotectin+*T.forsythia*+IL6+*P.intermedia*, Calprotectin+*T.forsythia*+IL6+*C.rectus*, *T.forsythia*+IL13+TNFa+*P.intermedia*, *T.denticola*+IL1beta+IL10+*P.intermedia*, *T.denticola*+IL6+IL2+*C.rectus*, MMP8+MMP9+*P.gingivalis*+*T.forsythia*, *T.denticola*+IL6+IL1beta+*C.rectus*, MMP9+*T.forsythia*+IL1beta+*F.nucleatum*, OPG+*T.forsythia*+*T.denticola*+IL13, *T.forsythia*+ICTP+IL1beta+*P.intermedia*, MMP9+*T.denticola*+IL2+*F.nucleatum*, *P.gingivalis*+IL6+ICTP+*P.intermedia*, *T.forsythia*+ICTP+TNFa+*P.intermedia*, *T.denticola*+IL6+IL10+*P.intermedia*, *T.denticola*+IL6+IL10+*C.rectus*, MMP9+*T.denticola*+TNFa+*F.nucleatum*, *T.forsythia*+ICTP+IL4+*P.intermedia*, MMP8+*T.denticola*+IL13+*F.nucleatum*, MMP8+*T.denticola*+TNFa+*F.nucleatum*, MMP8+MMP9+*T.denticola*+*F.nucleatum*, Calprotectin+*T.forsythia*+ICTP+*C.rectus*, MMP9+*T.denticola*+IL6+*F.nucleatum*, MMP9+*T.denticola*+IL13+*F.nucleatum*, MMP9+*T.denticola*+IL4+*F.nucleatum*, MMP8+*P.gingivalis*+ICTP+*C.rectus*, OPG+*T.denticola*+IL13+*C.rectus*, *T.denticola*+IL10+IL2+*P.intermedia*, *T.denticola*+IL10+IL13+*C.rectus*, MMP8+*T.denticola*+IL6+*F.nucleatum*, Calprotectin+OPG+*T.denticola*+*F.nucleatum*, OPG+*T.forsythia*+*T.denticola*+TNFa, *T.forsythia*+*T.denticola*+IL2+IL13, *T.forsythia*+IL6+IL13+*P.intermedia*, MMP9+*P.gingivalis*+ICTP+*C.rectus*, *T.forsythia*+IL10+IL13+*P.intermedia*, *T.denticola*+IL10+IL2+*C.rectus*, MMP8+*T.denticola*+IL4+*F.nucleatum*, Calprotectin+OPG+*T.forsythia*+*F.nucleatum*, MMP9+*P.gingivalis*+*T.forsythia*+IL2, MMP8+*T.forsythia*+TNFa+*C.rectus*, MMP8+Calprotectin+*P.gingivalis*+*F.nucleatum*, MMP9+*T.forsythia*+ICTP+*F.nucleatum*, MMP9+*T.forsythia*+IL2+*C.rectus*, OPG+*T.forsythia*+*T.denticola*+IL4, *T.forsythia*+ICTP+IL10+*P.intermedia*, Calprotectin+*P.gingivalis*+*T.forsythia*+IL13, OPG+*T.forsythia*+*T.denticola*+IL6, MMP9+*P.gingivalis*+*T.forsythia*+IL10, MMP8+OPG+*T.forsythia*+*C.rectus*, Calprotectin+*T.forsythia*+*T.denticola*+IL6, MMP9+*P.gingivalis*+ICTP+*F.nucleatum*, MMP9+*T.forsythia*+TNFa+*F.nucleatum*, *T.forsythia*+ICTP+IL2+*P.intermedia*, *T.denticola*+IL1beta+IL10+*C.rectus*, *T.denticola*+IL10+IL4+*C.rectus*, MMP8+*P.gingivalis*+*T.forsythia*+IL10, Calprotectin+*P.gingivalis*+IL6+*C.rectus*, Calprotectin+*T.forsythia*+*T.denticola*+IL10, MMP9+OPG+*T.forsythia*+*C.rectus*, OPG+*T.forsythia*+*T.denticola*+IL1beta, *T.forsythia*+IL1beta+IL13+*P.intermedia*, *T.forsythia*+IL2+IL13+*P.intermedia*, *T.denticola*+IL10+TNFa+*C.rectus*, MMP8+*T.forsythia*+TNFa+*F.nucleatum*, Calprotectin+*T.forsythia*+*T.denticola*+TNFa, Calprotectin+*T.forsythia*+ICTP+*F.nucleatum*, *P.gingivalis*+ICTP+IL13+*P.intermedia*, *P.gingivalis*+IL10+IL13+*P.intermedia*, MMP9+*P.gingivalis*+*T.forsythia*+IL6, OPG+*T.forsythia*+*T.denticola*+IL10, MMP8+*P.gingivalis*+*T.forsythia*+IL6, Calprotectin+*T.forsythia*+*T.denticola*+IL1beta, OPG+*T.forsythia*+*T.denticola*+IL2, *P.gingivalis*+ICTP+IL1beta+*P.intermedia*, *T.denticola*+IL1beta+IL13+*C.rectus*, Calprotectin+*T.forsythia*+*T.denticola*+IL2, *P.gingivalis*+ICTP+TNFa+*P.intermedia*, MMP9+*T.forsythia*+IL4+*C.rectus*, *T.forsythia*+IL6+ICTP+*P.intermedia*, *T.denticola*+IL2+IL13+*C.rectus*, MMP9+*T.forsythia*+IL13+*F.nucleatum*, MMP9+*T.forsythia*+IL13+*C.rectus*, OPG+*T.forsythia*+ICTP+*P.intermedia*, MMP8+*P.gingivalis*+*T.forsythia*+IL2, OPG+*T.forsythia*+IL13+*P.intermedia*, *T.forsythia*+*T.denticola*+IL13+IL4, *T.denticola*+IL2+TNFa+*C.rectus*, *P.gingivalis*+ICTP+IL10+*P.intermedia*, *T.forsythia*+*T.denticola*+IL1beta+IL13, *T.forsythia*+IL13+IL4+*P.intermedia*, *P.gingivalis*+IL1beta+IL13+*P.intermedia*, MMP8+*T.forsythia*+IL13+*F.nucleatum*, Calprotectin+*P.gingivalis*+*T.forsythia*+ICTP, *T.forsythia*+*T.denticola*+IL2+TNFa, MMP8+MMP9+*T.forsythia*+*C.rectus*, MMP8+*T.forsythia*+IL13+*C.rectus*, Calprotectin+*T.forsythia*+*T.denticola*+IL4, Calprotectin+*T.forsythia*+IL13+*F.nucleatum*, OPG+*T.denticola*+IL1beta+*C.rectus*, *T.denticola*+IL1beta+IL2+*C.rectus*, *T.denticola*+IL2+IL4+*C.rectus*, MMP8+OPG+*T.forsythia*+*F.nucleatum*, MMP8+*T.forsythia*+IL4+*C.rectus*, Calprotectin+OPG+*P.gingivalis*+*T.denticola*, OPG+*T.denticola*+IL2+*C.rectus*, *T.forsythia*+IL1beta+TNFa+*P.intermedia*, *P.gingivalis*+ICTP+IL2+*P.intermedia*, *T.forsythia*+IL10+TNFa+*P.intermedia*, Calprotectin+*P.gingivalis*+*T.denticola*+IL13, Calprotectin+*T.forsythia*+IL1beta+*F.nucleatum*, OPG+*P.gingivalis*+ICTP+*P.intermedia*, *P.gingivalis*+ICTP+IL4+*P.intermedia*, *T.forsythia*+*T.denticola*+IL1beta+IL10, *T.forsythia*+*T.denticola*+IL10+TNFa, MMP8+*T.forsythia*+IL2+*C.rectus*, Calprotectin+*T.forsythia*+IL13+*C.rectus*, *T.forsythia*+*T.denticola*+IL6+IL4, *T.forsythia*+IL6+TNFa+*P.intermedia*, Calprotectin+OPG+*P.gingivalis*+*T.forsythia*, *T.forsythia*+*T.denticola*+IL6+TNFa, *T.forsythia*+*T.denticola*+IL13+TNFa, *T.denticola*+IL13+IL4+*C.rectus*, MMP9+*T.forsythia*+IL6+*C.rectus*, OPG+*P.gingivalis*+*T.denticola*+IL13, OPG+*T.forsythia*+TNFa+*P.intermedia*, *P.gingivalis*+*T.forsythia*+IL6+ICTP, *T.forsythia*+*T.denticola*+IL6+IL1beta, Calprotectin+*P.gingivalis*+*T.denticola*+IL6, OPG+*P.gingivalis*+*T.denticola*+IL10, *T.forsythia*+*T.denticola*+IL1beta+IL2, MMP9+*T.forsythia*+TNFa+*C.rectus*, Calprotectin+*P.gingivalis*+ICTP+*F.nucleatum*, MMP9+*T.forsythia*+IL10+*C.rectus*, OPG+*T.denticola*+IL4+*C.rectus*, *T.forsythia*+*T.denticola*+IL2+IL4, OPG+*P.gingivalis*+*T.denticola*+IL6, OPG+*T.denticola*+TNFa+*C.rectus*, *P.gingivalis*+*T.denticola*+IL10+IL13, *T.forsythia*+IL2+TNFa+*P.intermedia*, *T.denticola*+IL13+TNFa+*C.rectus*, *T.denticola*+IL4+TNFa+*C.rectus*, *T.forsythia*+IL1beta+IL10+*P.intermedia*, *T.forsythia*+IL4+TNFa+*P.intermedia*, Calprotectin+OPG+*P.gingivalis*+*C.rectus*, *T.forsythia*+*T.denticola*+IL6+IL2, *T.forsythia*+*T.denticola*+IL1beta+TNFa, *T.denticola*+IL1beta+IL4+*C.rectus*, Calprotectin+*T.denticola*+IL6+*F.nucleatum*, *P.gingivalis*+*T.forsythia*+

IL6+IL13, P.gingivalis+IL6+IL13+P.intermedia, Calprotectin+T.forsythia+TNFa+F.nucleatum, MMP9+T.forsythia+IL4+F.nucleatum, OPG+P.gingivalis+T.denticola+IL4, P.gingivalis+IL6+TNFa+P.intermedia, Calprotectin+T.forsythia+IL1beta+C.rectus, MMP9+P.gingivalis+IL6+F.nucleatum, MMP9+P.gingivalis+IL10+F.nucleatum, P.gingivalis+T.denticola+IL6+IL13, T.forsythia+T.denticola+IL1beta+IL4, T.forsythia+IL6+IL10+P.intermedia, T.forsythia+IL6+IL13+C.rectus, T.denticola+IL1beta+TNFa+C.rectus, MMP8+P.gingivalis+IL10+F.nucleatum, MMP8+T.forsythia+IL10+C.rectus, MMP9+P.gingivalis+IL6+C.rectus, MMP9+P.gingivalis+TNFa+C.rectus, T.forsythia+T.denticola+IL10+IL4, T.forsythia+IL6+IL1beta+P.intermedia, MMP8+T.forsythia+IL6+C.rectus, Calprotectin+P.gingivalis+T.forsythia+IL6, Calprotectin+T.forsythia+TNFa+C.rectus, MMP9+T.forsythia+IL2+F.nucleatum, OPG+P.gingivalis+T.denticola+IL1beta, OPG+P.gingivalis+T.denticola+IL2, T.forsythia+IL6+ICTP+C.rectus, MMP8+P.gingivalis+IL1beta+F.nucleatum, MMP9+OPG+P.gingivalis+C.rectus, OPG+P.gingivalis+IL13+P.intermedia, OPG+T.forsythia+IL1beta+P.intermedia, T.forsythia+T.denticola+IL4+TNFa, MMP8+MMP9+P.gingivalis+C.rectus, MMP8+T.forsythia+IL4+F.nucleatum, Calprotectin+T.forsythia+IL10+C.rectus, Calprotectin+T.denticola+IL2+F.nucleatum, P.gingivalis+T.denticola+IL2+IL13, P.gingivalis+IL13+IL4+P.intermedia, MMP8+T.forsythia+IL6+F.nucleatum, MMP9+T.forsythia+IL6+F.nucleatum, P.gingivalis+T.denticola+IL1beta+IL13, P.gingivalis+IL6+IL4+P.intermedia, T.forsythia+T.denticola+IL10+IL2, Calprotectin+OPG+P.gingivalis+F.nucleatum, Calprotectin+T.forsythia+IL6+F.nucleatum, OPG+T.forsythia+IL2+P.intermedia, P.gingivalis+IL6+ICTP+F.nucleatum, P.gingivalis+IL6+IL1beta+P.intermedia, Calprotectin+T.forsythia+IL4+F.nucleatum, MMP9+P.gingivalis+IL1beta+F.nucleatum, MMP9+P.gingivalis+IL4+C.rectus, OPG+T.forsythia+IL6+P.intermedia, T.forsythia+T.denticola+IL6+IL10, T.forsythia+IL10+IL4+P.intermedia, MMP9+P.gingivalis+TNFa+F.nucleatum, OPG+P.gingivalis+T.forsythia+IL6, OPG+P.gingivalis+T.denticola+TNFa, P.gingivalis+IL2+IL13+P.intermedia, T.forsythia+IL6+IL13+F.nucleatum, Calprotectin+T.denticola+IL10+F.nucleatum, MMP9+P.gingivalis+IL13+C.rectus, T.forsythia+IL10+IL2+P.intermedia, MMP8+OPG+P.gingivalis+C.rectus, Calprotectin+T.forsythia+IL2+C.rectus, MMP9+P.gingivalis+IL10+C.rectus, T.forsythia+ICTP+IL13+F.nucleatum, MMP8+OPG+P.gingivalis+F.nucleatum, MMP8+P.gingivalis+IL6+F.nucleatum, Calprotectin+T.denticola+IL13+F.nucleatum, MMP9+OPG+T.forsythia+F.nucleatum, MMP9+P.gingivalis+IL2+C.rectus, P.gingivalis+T.denticola+IL13+IL4, Calprotectin+P.gingivalis+T.denticola+IL10, Calprotectin+T.forsythia+IL4+C.rectus, OPG+T.forsythia+IL10+P.intermedia, P.gingivalis+IL6+IL10+P.intermedia, P.gingivalis+IL6+IL2+P.intermedia, MMP8+T.forsythia+IL2+F.nucleatum, Calprotectin+T.denticola+TNFa+F.nucleatum, MMP9+T.forsythia+IL10+F.nucleatum, OPG+P.gingivalis+IL6+P.intermedia, OPG+T.forsythia+IL4+P.intermedia, P.gingivalis+T.denticola+IL13+TNFa, T.forsythia+IL1beta+IL2+P.intermedia, T.forsythia+IL1beta+IL4+P.intermedia, MMP8+MMP9+T.forsythia+F.nucleatum, MMP8+P.gingivalis+TNFa+C.rectus, P.gingivalis+IL6+ICTP+C.rectus, Calprotectin+P.gingivalis+T.denticola+IL2, Calprotectin+P.gingivalis+IL6+F.nucleatum, P.gingivalis+IL1beta+IL10+P.intermedia, T.forsythia+ICTP+IL13+C.rectus, MMP8+P.gingivalis+IL4+C.rectus, P.gingivalis+T.forsythia+IL6+TNFa, P.gingivalis+T.forsythia+ICTP+IL13, T.forsythia+IL6+IL4+P.intermedia, MMP8+P.gingivalis+IL1beta+C.rectus, MMP8+T.forsythia+IL10+F.nucleatum, MMP9+P.gingivalis+IL1beta+C.rectus, P.gingivalis+IL13+TNFa+P.intermedia, MMP9+P.gingivalis+IL4+F.nucleatum, T.denticola+IL6+IL13+F.nucleatum, OPG+P.gingivalis+TNFa+P.intermedia, T.forsythia+ICTP+TNFa+F.nucleatum, MMP8+P.gingivalis+IL10+C.rectus, Calprotectin+T.denticola+IL4+F.nucleatum, OPG+T.denticola+IL13+F.nucleatum, P.gingivalis+IL1beta+TNFa+P.intermedia, T.forsythia+IL6+IL2+P.intermedia, T.denticola+IL10+IL13+F.nucleatum, T.denticola+IL2+TNFa+F.nucleatum, MMP8+MMP9+P.gingivalis+F.nucleatum, Calprotectin+P.gingivalis+ICTP+C.rectus, OPG+T.denticola+IL6+F.nucleatum, MMP8+P.gingivalis+TNFa+F.nucleatum, OPG+P.gingivalis+IL1beta+P.intermedia, OPG+P.gingivalis+IL4+P.intermedia, P.gingivalis+T.forsythia+IL10+IL13, P.gingivalis+IL1beta+IL2+P.intermedia, P.gingivalis+IL1beta+IL4+P.intermedia, T.forsythia+IL6+ICTP+F.nucleatum, MMP8+P.gingivalis+IL13+C.rectus, Calprotectin+T.denticola+IL1beta+F.nucleatum, MMP9+P.gingivalis+IL13+F.nucleatum, P.gingivalis+T.forsythia+IL6+IL4, P.gingivalis+IL10+TNFa+P.intermedia, Calprotectin+P.gingivalis+T.forsythia+IL10, Calprotectin+P.gingivalis+IL10+C.rectus, P.gingivalis+T.forsythia+ICTP+IL10, P.gingivalis+IL4+TNFa+P.intermedia, OPG+P.gingivalis+IL10+P.intermedia, OPG+P.gingivalis+IL2+P.intermedia, MMP8+P.gingivalis+IL6+C.rectus, MMP8+P.gingivalis+IL4+F.nucleatum, Calprotectin+P.gingivalis+T.denticola+IL1beta, Calprotectin+T.forsythia+IL2+F.nucleatum, OPG+P.gingivalis+T.forsythia+ICTP, P.gingivalis+T.denticola+IL6+IL1beta, P.gingivalis+T.denticola+IL6+IL2, P.gingivalis+IL2+IL4+P.intermedia, P.gingivalis+IL2+TNFa+P.intermedia, MMP8+P.gingivalis+IL2+F.nucleatum, OPG+T.denticola+IL10+F.nucleatum, P.gingivalis+IL10+IL2+P.intermedia, T.denticola+IL2+IL13+F.nucleatum, Calprotectin+P.gingivalis+T.denticola+TNFa, MMP9+P.gingivalis+IL2+F.nucleatum, P.gingivalis+T.forsythia+IL6+IL1beta, P.gingivalis+T.denticola+IL10+IL2, MMP8+P.gingivalis+IL13+F.nucleatum, OPG+T.denticola+IL2+F.nucleatum, P.gingivalis+T.denticola+IL6+IL10, P.gingivalis+T.denticola+IL6+TNFa, MMP9+OPG+P.gingivalis+F.nucleatum, T.forsythia+IL2+IL4+P.intermedia, OPG+T.denticola+TNFa+F.nucleatum, P.gingivalis+T.denticola+IL6+IL4, P.gingivalis+T.forsythia+IL2+TNFa, T.forsythia+IL10+IL13+F.nucleatum, Calprotectin+T.forsythia+IL10+F.nucleatum, P.gingivalis+T.forsythia+IL6+IL10, Calprotectin+P.gingivalis+T.denticola+IL4, Calprotectin+P.gingivalis+IL10+F.nucleatum, OPG+T.denticola+IL1beta+F.nucleatum, P.gingivalis+IL10+IL4+P.intermedia, T.forsythia+ICTP+IL10+C.rectus, P.gingivalis+T.denticola+IL10+TNFa, P.gingivalis+T.forsythia+IL6+IL2, P.gingivalis+T.denticola+IL1beta+IL10, P.gingivalis+T.denticola+IL1beta+IL2, T.forsythia+IL6+TNFa+C.rectus, Calprotectin+P.gingivalis+T.forsythia+IL4, OPG+T.forsythia+IL13+F.nucleatum, MMP8+P.gingivalis+IL2+C.rectus, Calprotectin+P.gingivalis+T.forsythia+TNFa, OPG+P.gingivalis+T.forsythia+IL10, T.forsythia+IL6+TNFa+F.nucleatum, T.denticola+IL6+IL10+F.nucleatum, Calprotectin+P.gingivalis+T.forsythia+IL2, OPG+T.forsythia+ICTP+F.nucleatum, OPG+T.forsythia+ICTP+C.rectus, P.gingivalis+T.denticola+IL10+IL4, T.denticola+IL6+IL1beta+F.nucleatum, Calprotectin+P.gingivalis+IL4+C.rectus, P.gingivalis+T.forsythia+ICTP+IL2, P.gingivalis+T.denticola+IL2+IL4, T.forsythia+ICTP+IL2+F.nucleatum, P.gingivalis+T.forsythia+ICTP+IL4, P.gingivalis+T.forsythia+IL1beta+IL13, Calprotectin+P.gingivalis+IL2+C.rectus, P.gingivalis+T.forsythia+ICTP+TNFa, T.denticola+IL13+IL4+F.nucleatum, T.denticola+IL6+TNFa+

F.nucleatum, OPG+T.denticola+IL4+F.nucleatum, Calprotectin+P.gingivalis+T.forsythia+IL1beta, T.forsythia+IL6+IL1beta+F.nucleatum, T.forsythia+ICTP+IL4+F.nucleatum, T.forsythia+IL2+IL13+F.nucleatum, T.denticola+IL1beta+IL10+F.nucleatum, Calprotectin+P.gingivalis+TNFa+C.rectus, OPG+T.forsythia+TNFa+F.nucleatum, T.forsythia+ICTP+IL1beta+F.nucleatum, T.denticola+IL10+TNFa+F.nucleatum, Calprotectin+P.gingivalis+IL1beta+C.rectus, OPG+P.gingivalis+T.forsythia+IL13, T.forsythia+ICTP+IL10+F.nucleatum, T.forsythia+ICTP+TNFa+C.rectus, T.denticola+IL6+IL2+F.nucleatum, T.forsythia+IL1beta+IL13+F.nucleatum, OPG+T.forsythia+IL6+F.nucleatum, T.forsythia+IL10+IL13+C.rectus, T.forsythia+ICTP+IL4+C.rectus, P.gingivalis+T.forsythia+IL2+IL13, P.gingivalis+T.forsythia+IL13+TNFa, T.forsythia+IL6+IL4+C.rectus, T.forsythia+ICTP+IL1beta+C.rectus, P.gingivalis+T.forsythia+ICTP+IL1beta, T.denticola+IL1beta+IL2+F.nucleatum, T.denticola+IL1beta+IL13+F.nucleatum, P.gingivalis+T.denticola+IL4+TNFa, T.forsythia+IL13+IL4+F.nucleatum, T.denticola+IL6+IL4+F.nucleatum, T.forsythia+IL6+IL1beta+C.rectus, T.forsythia+IL6+IL10+C.rectus, OPG+P.gingivalis+T.forsythia+IL2, T.forsythia+IL6+IL2+C.rectus, P.gingivalis+T.denticola+IL1beta+IL4, T.forsythia+ICTP+IL2+C.rectus, Calprotectin+P.gingivalis+IL13+F.nucleatum, P.gingivalis+IL6+TNFa+F.nucleatum, T.forsythia+IL6+IL4+F.nucleatum, T.denticola+IL2+IL4+F.nucleatum, OPG+P.gingivalis+T.forsythia+IL4, OPG+T.forsythia+IL6+C.rectus, P.gingivalis+IL6+IL13+F.nucleatum, Calprotectin+P.gingivalis+TNFa+F.nucleatum, P.gingivalis+IL10+IL13+F.nucleatum, OPG+P.gingivalis+T.forsythia+TNFa, P.gingivalis+T.forsythia+IL13+IL4, P.gingivalis+ICTP+IL10+F.nucleatum, Calprotectin+P.gingivalis+IL2+F.nucleatum, Calprotectin+P.gingivalis+IL4+F.nucleatum, T.forsythia+IL13+TNFa+F.nucleatum, T.denticola+IL13+TNFa+F.nucleatum, Calprotectin+P.gingivalis+IL13+C.rectus, T.denticola+IL10+IL4+F.nucleatum, P.gingivalis+T.denticola+IL1beta+TNFa, OPG+T.forsythia+IL4+C.rectus, OPG+T.forsythia+IL1beta+C.rectus, OPG+T.forsythia+IL13+C.rectus, P.gingivalis+T.forsythia+IL10+IL2, T.forsythia+IL10+TNFa+F.nucleatum, Calprotectin+P.gingivalis+IL1beta+F.nucleatum, OPG+T.forsythia+IL4+F.nucleatum, P.gingivalis+ICTP+IL1beta+F.nucleatum, T.forsythia+IL1beta+TNFa+F.nucleatum, OPG+P.gingivalis+IL6+F.nucleatum, OPG+T.forsythia+IL1beta+F.nucleatum, T.forsythia+IL4+TNFa+F.nucleatum, OPG+P.gingivalis+T.forsythia+IL1beta, T.denticola+IL1beta+IL4+F.nucleatum, OPG+T.forsythia+TNFa+C.rectus, P.gingivalis+IL6+IL1beta+F.nucleatum, P.gingivalis+IL6+IL13+C.rectus, T.forsythia+IL6+IL10+F.nucleatum, T.forsythia+IL6+IL2+F.nucleatum, T.forsythia+IL13+TNFa+C.rectus, OPG+T.forsythia+IL2+F.nucleatum, OPG+T.forsythia+IL2+C.rectus, P.gingivalis+IL6+IL10+F.nucleatum, T.forsythia+IL13+IL4+C.rectus, OPG+P.gingivalis+ICTP+F.nucleatum, T.forsythia+IL2+IL13+C.rectus, T.forsythia+IL2+TNFa+F.nucleatum, T.denticola+IL10+IL2+F.nucleatum, T.denticola+IL4+TNFa+F.nucleatum, P.gingivalis+T.forsythia+IL10+IL4, OPG+T.forsythia+IL10+F.nucleatum, P.gingivalis+IL6+IL4+F.nucleatum, T.forsythia+IL1beta+IL13+C.rectus, P.gingivalis+IL6+IL2+F.nucleatum, P.gingivalis+ICTP+IL4+F.nucleatum, P.gingivalis+ICTP+IL2+F.nucleatum, OPG+T.forsythia+IL10+C.rectus, P.gingivalis+T.forsythia+IL2+IL4, T.forsythia+IL1beta+IL10+F.nucleatum, T.forsythia+IL1beta+IL2+F.nucleatum, OPG+P.gingivalis+IL10+C.rectus, P.gingivalis+T.forsythia+IL1beta+IL10, T.forsythia+IL1beta+IL4+F.nucleatum, T.forsythia+IL2+IL4+F.nucleatum, P.gingivalis+T.forsythia+IL10+TNFa, T.forsythia+IL2+IL4+C.rectus, T.denticola+IL1beta+TNFa+F.nucleatum, T.forsythia+IL1beta+IL4+C.rectus, T.forsythia+IL2+TNFa+C.rectus, T.forsythia+IL1beta+IL2+C.rectus, T.forsythia+IL1beta+IL2+F.nucleatum, T.forsythia+IL10+C.rectus, T.forsythia+IL1beta+TNFa+C.rectus, T.forsythia+IL10+IL4+F.nucleatum, P.gingivalis+T.forsythia+IL2+TNFa, P.gingivalis+IL6+TNFa+C.rectus, P.gingivalis+IL6+IL4+C.rectus, P.gingivalis+ICTP+TNFa+F.nucleatum, MMP8+Calprotectin+P.intermedia+C.rectus, P.gingivalis+IL6+IL2+C.rectus, P.gingivalis+IL6+IL1beta+C.rectus, OPG+P.gingivalis+IL10+F.nucleatum, P.gingivalis+ICTP+IL13+F.nucleatum, T.forsythia+IL10+IL4+C.rectus, T.forsythia+IL10+TNFa+C.rectus, T.forsythia+IL4+TNFa+C.rectus, P.gingivalis+ICTP+IL10+C.rectus, P.gingivalis+ICTP+IL1beta+C.rectus, P.gingivalis+ICTP+IL4+C.rectus, P.gingivalis+T.forsythia+IL1beta+IL4, P.gingivalis+ICTP+IL2+C.rectus, P.gingivalis+T.forsythia+IL4+TNFa, P.gingivalis+ICTP+TNFa+C.rectus, T.forsythia+IL10+IL2+F.nucleatum, Calprotectin+MMP9+P.intermedia+C.rectus, P.gingivalis+IL6+IL10+C.rectus, OPG+P.gingivalis+ICTP+C.rectus, P.gingivalis+T.forsythia+IL1beta+TNFa, Calprotectin+MMP9+P.intermedia+F.nucleatum, P.gingivalis+T.forsythia+IL1beta+IL2, MMP8+Calprotectin+P.intermedia+F.nucleatum, T.forsythia+IL10+IL2+C.rectus, P.gingivalis+ICTP+IL13+C.rectus, P.gingivalis+IL10+TNFa+F.nucleatum, MMP8+ICTP+P.intermedia+F.nucleatum, MMP8+ICTP+P.intermedia+C.rectus, OPG+P.gingivalis+IL4+F.nucleatum, P.gingivalis+IL10+IL2+F.nucleatum, P.gingivalis+IL1beta+IL10+F.nucleatum, P.gingivalis+IL10+IL4+F.nucleatum, OPG+P.gingivalis+IL1beta+F.nucleatum, MMP8+TNFa+P.intermedia+F.nucleatum, OPG+P.gingivalis+IL2+F.nucleatum, P.gingivalis+IL13+IL4+F.nucleatum, OPG+P.gingivalis+TNFa+F.nucleatum, P.gingivalis+IL1beta+IL4+F.nucleatum, P.gingivalis+IL2+IL13+F.nucleatum, P.gingivalis+IL2+IL4+F.nucleatum, OPG+P.gingivalis+IL13+F.nucleatum, P.gingivalis+IL2+TNFa+F.nucleatum, P.gingivalis+IL1beta+IL2+F.nucleatum, P.gingivalis+IL4+TNFa+F.nucleatum, P.gingivalis+IL13+TNFa+F.nucleatum, P.gingivalis+IL1beta+IL13+F.nucleatum, P.gingivalis+IL1beta+TNFa+F.nucleatum, MMP8+IL1beta+P.intermedia+F.nucleatum, MMP8+TNFa+P.intermedia+C.rectus, P.gingivalis+IL10+IL13+C.rectus, MMP9+TNFa+P.intermedia+C.rectus, P.gingivalis+IL1beta+IL10+C.rectus, OPG+P.gingivalis+IL10+C.rectus, MMP8+IL1beta+P.intermedia+C.rectus, P.gingivalis+IL1beta+IL2+C.rectus, P.gingivalis+IL10+IL2+C.rectus, P.gingivalis+IL2+IL13+C.rectus, Calprotectin+TNFa+P.intermedia+F.nucleatum, MMP9+TNFa+P.intermedia+F.nucleatum, OPG+P.gingivalis+IL13+C.rectus, MMP8+IL10+P.intermedia+F.nucleatum, MMP8+IL6+P.intermedia+F.nucleatum, OPG+P.gingivalis+IL1beta+C.rectus, P.gingivalis+IL13+IL4+C.rectus, Calprotectin+ICTP+P.intermedia+F.nucleatum, MMP9+IL1beta+P.intermedia+C.rectus, MMP9+ICTP+P.intermedia+C.rectus, OPG+P.gingivalis+IL2+C.rectus, OPG+P.gingivalis+TNFa+C.rectus, MMP8+OPG+P.intermedia+F.nucleatum, OPG+P.gingivalis+IL4+C.rectus, MMP8+IL13+P.intermedia+C.rectus, MMP8+IL13+P.intermedia+F.nucleatum, MMP9+ICTP+P.intermedia+F.nucleatum, P.gingivalis+IL2+IL4+C.rectus, P.gingivalis+IL10+TNFa+C.rectus, Calprotectin+ICTP+P.intermedia+C.rectus, MMP8+IL2+P.intermedia+F.nucleatum, P.gingivalis+IL10+IL4+C.rectus, MMP8+MMP9+P.intermedia+C.rectus, MMP8+IL4+P.intermedia+F.nucleatum, MMP9+IL1beta+P.intermedia+F.nucleatum, P.gingivalis+IL13+TNFa+C.rectus, MMP8+MMP9+P.intermedia+F.nucleatum, MMP8+OPG+P.intermedia+C.rectus, MMP8+IL10+P.intermedia+C.rectus, MMP9+IL2+P.intermedia+*C.rectus*, *P.gingivalis*+IL2+TNFa+*C.rectus*, Calprotectin+MMP9+*F.nucleatum*+*C.rectus*, MMP8+IL2+*P.intermedia*+*C.rectus*, MMP8+IL6+*P.intermedia*+*C.rectus*, *P.gingivalis*+IL1beta+IL4+*C.rectus*, MMP9+IL4+*P.intermedia*+*F.nucleatum*, *P.gingivalis*+IL1beta+TNFa+*C.rectus*, *P.gingivalis*+IL4+TNFa+*C.rectus*, MMP8+IL4+*P.intermedia*+*C.rectus*, Calprotectin+IL2+*P.intermedia*+*F.nucleatum*, Calprotectin+IL10+*P.intermedia*+*F.nucleatum*, Calprotectin+OPG+*P.intermedia*+*F.nucleatum*, Calprotectin+TNFa+*P.intermedia*+*C.rectus*, Calprotectin+IL13+*P.intermedia*+*F.nucleatum*, MMP9+IL2+*P.intermedia*+*F.nucleatum*, *P.gingivalis*+IL1beta+IL13+*C.rectus*, Calprotectin+IL6+*P.intermedia*+*F.nucleatum*, MMP9+IL6+*P.intermedia*+*F.nucleatum*, Calprotectin+IL1beta+*P.intermedia*+*F.nucleatum*, Calprotectin+IL4+*P.intermedia*+*F.nucleatum*, MMP9+IL6+*P.intermedia*+*C.rectus*, Calprotectin+OPG+*P.intermedia*+*C.rectus*, MMP9+IL13+*P.intermedia*+*C.rectus*, MMP9+OPG+*P.intermedia*+*C.rectus*, MMP9+IL10+*P.intermedia*+*C.rectus*, Calprotectin+IL10+*P.intermedia*+*C.rectus*, Calprotectin+IL2+*P.intermedia*+*C.rectus*, MMP9+IL13+*P.intermedia*+*F.nucleatum*, Calprotectin+IL6+*P.intermedia*+*C.rectus*, Calprotectin+IL4+*P.intermedia*+*C.rectus*, MMP9+OPG+*P.intermedia*+*F.nucleatum*, IL4+TNFa+*P.intermedia*+*F.nucleatum*, MMP8+Calprotectin+*F.nucleatum*+*C.rectus*, MMP9+IL10+*P.intermedia*+*F.nucleatum*, Calprotectin+IL1beta+*P.intermedia*+*C.rectus*, Calprotectin+IL13+*P.intermedia*+*C.rectus*, MMP9+IL4+*P.intermedia*+*C.rectus*, ICTP+TNFa+*P.intermedia*+*F.nucleatum*, IL1beta+TNFa+*P.intermedia*+*F.nucleatum*, IL10+TNFa+*P.intermedia*+*F.nucleatum*, MMP8+ICTP+*F.nucleatum*+*C.rectus*, ICTP+IL4+*P.intermedia*+*F.nucleatum*, IL6+ICTP+*P.intermedia*+*F.nucleatum*, ICTP+IL1beta+*P.intermedia*+*F.nucleatum*, MMP9+ICTP+*F.nucleatum*+*C.rectus*, ICTP+IL2+*P.intermedia*+*F.nucleatum*, IL2+TNFa+*P.intermedia*+*F.nucleatum*, ICTP+TNFa+*P.intermedia*+*C.rectus*, ICTP+IL10+*P.intermedia*+*F.nucleatum*, IL13+TNFa+*P.intermedia*+*F.nucleatum*, ICTP+IL13+*P.intermedia*+*F.nucleatum*, OPG+ICTP+*P.intermedia*+*F.nucleatum*, IL6+TNFa+*P.intermedia*+*F.nucleatum*, OPG+TNFa+*P.intermedia*+*F.nucleatum*, Calprotectin+IL10+*F.nucleatum*+*C.rectus*, IL6+ICTP+*P.intermedia*+*C.rectus*, Calprotectin+OPG+*F.nucleatum*+*C.rectus*, IL13+IL4+*P.intermedia*+*F.nucleatum*, MMP9+TNFa+*F.nucleatum*+*C.rectus*, IL4+TNFa+*P.intermedia*+*C.rectus*, OPG+IL4+*P.intermedia*+*F.nucleatum*, OPG+ICTP+*P.intermedia*+*C.rectus*, ICTP+IL4+*P.intermedia*+*C.rectus*, ICTP+IL10+*P.intermedia*+*C.rectus*, IL2+IL4+*P.intermedia*+*F.nucleatum*, ICTP+IL1beta+*P.intermedia*+*C.rectus*, MMP9+IL6+*F.nucleatum*+*C.rectus*, IL10+IL2+*P.intermedia*+*F.nucleatum*, IL6+IL10+*P.intermedia*+*F.nucleatum*, IL6+IL4+*P.intermedia*+*F.nucleatum*, IL1beta+IL4+*P.intermedia*+*F.nucleatum*, Calprotectin+IL1beta+*F.nucleatum*+*C.rectus*, ICTP+IL2+*P.intermedia*+*C.rectus*, IL10+IL4+*P.intermedia*+*F.nucleatum*, ICTP+IL13+*P.intermedia*+*C.rectus*, OPG+IL2+*P.intermedia*+*F.nucleatum*, IL1beta+IL10+*P.intermedia*+*F.nucleatum*, MMP8+TNFa+*F.nucleatum*+*C.rectus*, MMP9+OPG+*F.nucleatum*+*C.rectus*, OPG+IL10+*P.intermedia*+*F.nucleatum*, IL1beta+IL13+*P.intermedia*+*F.nucleatum*, IL2+IL13+*P.intermedia*+*F.nucleatum*, MMP9+IL2+*F.nucleatum*+*C.rectus*, MMP9+IL13+*F.nucleatum*+*C.rectus*, OPG+IL1beta+*P.intermedia*+*F.nucleatum*, IL6+IL1beta+*P.intermedia*+*F.nucleatum*, IL1beta+IL2+*P.intermedia*+*F.nucleatum*, Calprotectin+IL6+*F.nucleatum*+*C.rectus*, IL10+IL13+*P.intermedia*+*F.nucleatum*, OPG+IL6+*P.intermedia*+*F.nucleatum*, IL6+IL2+*P.intermedia*+*F.nucleatum*, IL10+TNFa+*P.intermedia*+*C.rectus*, Calprotectin+ICTP+*F.nucleatum*+*C.rectus*, MMP8+MMP9+*F.nucleatum*+*C.rectus*, MMP9+IL1beta+*F.nucleatum*+*C.rectus*, MMP8+IL10+*F.nucleatum*+*C.rectus*, Calprotectin+IL4+*F.nucleatum*+*C.rectus*, MMP9+IL10+*F.nucleatum*+*C.rectus*, OPG+IL13+*P.intermedia*+*F.nucleatum*, IL6+IL13+*P.intermedia*+*F.nucleatum*, IL1beta+TNFa+*P.intermedia*+*C.rectus*, MMP9+IL4+*F.nucleatum*+*C.rectus*, IL6+TNFa+*P.intermedia*+*C.rectus*, IL2+TNFa+*P.intermedia*+*C.rectus*, Calprotectin+IL13+*F.nucleatum*+*C.rectus*, MMP8+IL6+*F.nucleatum*+*C.rectus*, MMP8+IL13+*F.nucleatum*+*C.rectus*, MMP8+IL4+*F.nucleatum*+*C.rectus*, MMP8+IL1beta+*F.nucleatum*+*C.rectus*, IL13+IL4+*P.intermedia*+*C.rectus*, IL6+IL4+*P.intermedia*+*C.rectus*, MMP8+OPG+*F.nucleatum*+*C.rectus*, IL13+TNFa+*P.intermedia*+*C.rectus*, OPG+TNFa+*P.intermedia*+*C.rectus*, Calprotectin+TNFa+*F.nucleatum*+*C.rectus*, MMP8+IL2+*F.nucleatum*+*C.rectus*, IL6+IL1beta+*P.intermedia*+*C.rectus*, IL10+IL4+*P.intermedia*+*C.rectus*, IL2+IL4+*P.intermedia*+*C.rectus*, IL6+IL13+*P.intermedia*+*C.rectus*, IL1beta+IL4+*P.intermedia*+*C.rectus*, OPG+IL4+*P.intermedia*+*C.rectus*, Calprotectin+IL2+*F.nucleatum*+*C.rectus*, IL10+IL13+*P.intermedia*+*C.rectus*, IL6+IL2+*P.intermedia*+*C.rectus*, IL10+IL2+*P.intermedia*+*C.rectus*, IL6+IL10+*P.intermedia*+*C.rectus*, IL2+IL13+*P.intermedia*+*C.rectus*, OPG+IL2+*P.intermedia*+*C.rectus*, OPG+IL1beta+*P.intermedia*+*C.rectus*, OPG+IL10+*P.intermedia*+*C.rectus*, OPG+IL13+*P.intermedia*+*C.rectus*, IL1beta+IL10+*P.intermedia*+*C.rectus*, IL1beta+IL13+*P.intermedia*+*C.rectus*, IL1beta+IL2+*P.intermedia*+*C.rectus*, OPG+IL6+*P.intermedia*+*C.rectus*, IL6+ICTP+*F.nucleatum*+*C.rectus*, IL4+TNFa+*F.nucleatum*+*C.rectus*, ICTP+IL1beta+*F.nucleatum*+*C.rectus*, ICTP+IL4+*F.nucleatum*+*C.rectus*, ICTP+TNFa+*F.nucleatum*+*C.rectus*, ICTP+IL10+*F.nucleatum*+*C.rectus*, IL6+IL4+*F.nucleatum*+*C.rectus*, IL6+TNFa+*F.nucleatum*+*C.rectus*, ICTP+IL13+*F.nucleatum*+*C.rectus*, OPG+ICTP+*F.nucleatum*+*C.rectus*, ICTP+IL2+*F.nucleatum*+*C.rectus*, OPG+IL6+*F.nucleatum*+*C.rectus*, IL6+IL1beta+*F.nucleatum*+*C.rectus*, IL6+IL2+*F.nucleatum*+*C.rectus*, IL6+IL10+*F.nucleatum*+*C.rectus*, IL6+IL13+*F.nucleatum*+*C.rectus*, IL2+IL4+*F.nucleatum*+*C.rectus*, IL10+TNFa+*F.nucleatum*+*C.rectus*, IL13+IL4+*F.nucleatum*+*C.rectus*, OPG+IL4+*F.nucleatum*+*C.rectus*, IL1beta+IL10+*F.nucleatum*+*C.rectus*, OPG+IL1beta+*F.nucleatum*+*C.rectus*, IL1beta+IL4+*F.nucleatum*+*C.rectus*, IL10+IL13+*F.nucleatum*+*C.rectus*, OPG+IL10+*F.nucleatum*+*C.rectus*, IL1beta+IL13+*F.nucleatum*+*C.rectus*, IL13+TNFa+*F.nucleatum*+*C.rectus*, IL10+IL4+*F.nucleatum*+*C.rectus*, OPG+IL13+*F.nucleatum*+*C.rectus*, IL1beta+IL2+*F.nucleatum*+*C.rectus*, IL10+IL2+*F.nucleatum*+*C.rectus*, IL1beta+TNFa+*F.nucleatum*+*C.rectus*, IL2+IL13+*F.nucleatum*+*C.rectus*, OPG+TNFa+*F.nucleatum*+*C.rectus*, IL2+TNFa+*F.nucleatum*+*C.rectus*, and OPG+IL2+*F.nucleatum*+*C.rectus*.

The present invention provides a method wherein the probability of oral disease is calculated comprising the steps of: determining the levels of two or more biomarkers in said first individual and a second individual, generating a receiver operating characteristic (ROC) curve, and calculating area under said ROC curve (AUC), said area providing the probability of said oral disease.

In various aspects of the invention, the sample is selected from the group consisting of a bodily fluid, tissue and organ.

In some aspects, the fluid is saliva.

In other aspects of the invention, the biomarker levels are biomarker protein levels in the sample.

In an embodiment of the invention, the oral disease is periodontal disease.

In another embodiment, the oral disease is peri-implant disease.

The present invention also provides a kit for carrying out different embodiments of the method of the invention, the kit comprising: a) a sterile container for sample collection, and b) one or more components selected from the group consisting of one or more reagents for performing the assay, a calibration standard and a quality control sample.

DETAILED DESCRIPTION OF THE INVENTION

Figure 1:
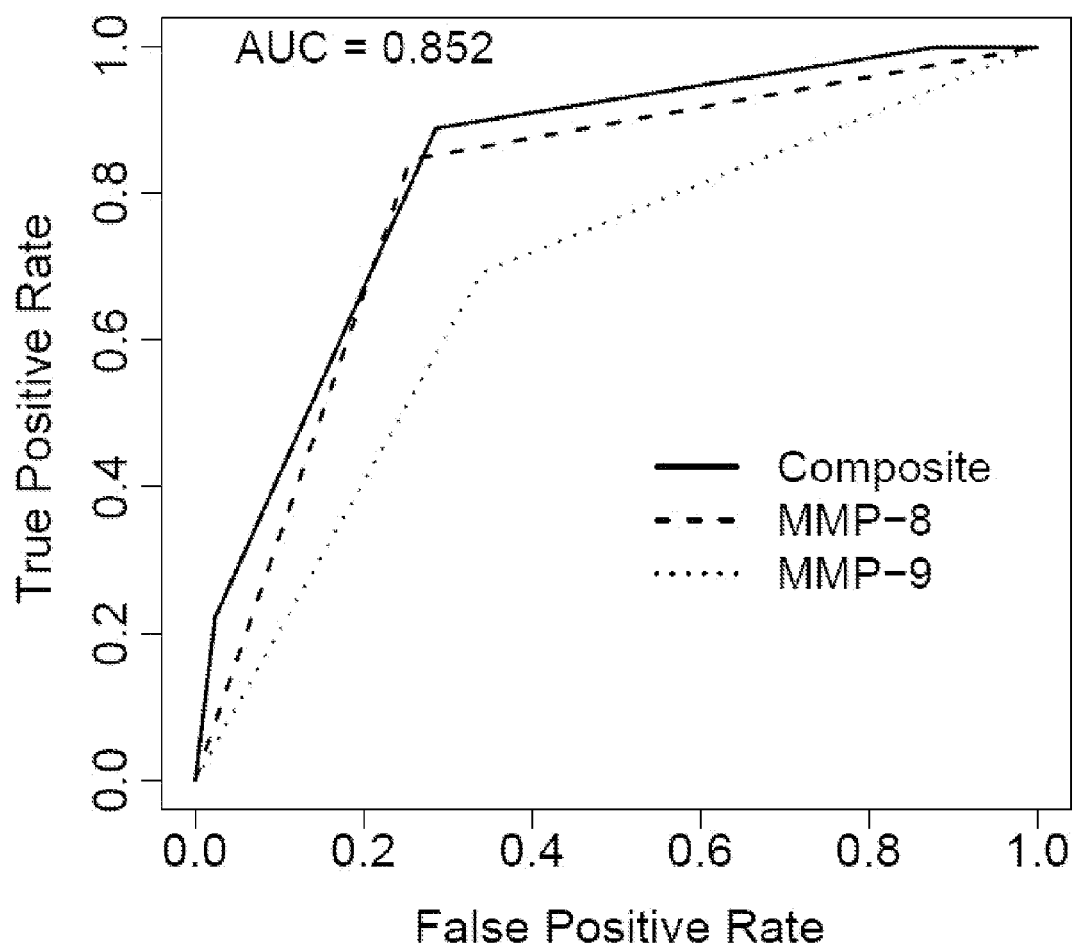
FIG. 1 depicts a receiver operating characteristic curve (ROC) and area under the curve data for the combination of MMP-8 and MMP-9.
Figure 2:
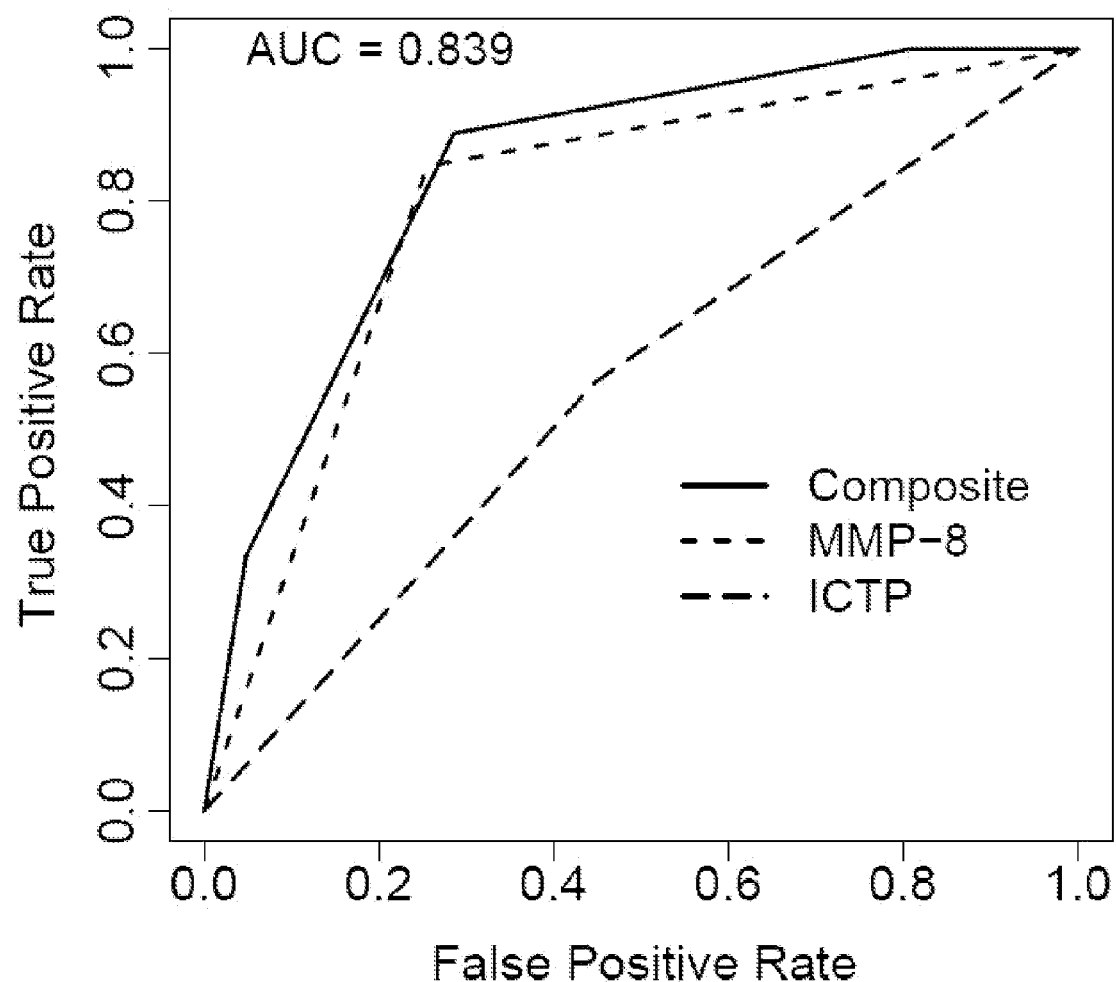
FIG. 2 depicts a receiver operating characteristic curve (ROC) and area under the curve data for the combination of MMP-8 and ICTP.
Figure 3:
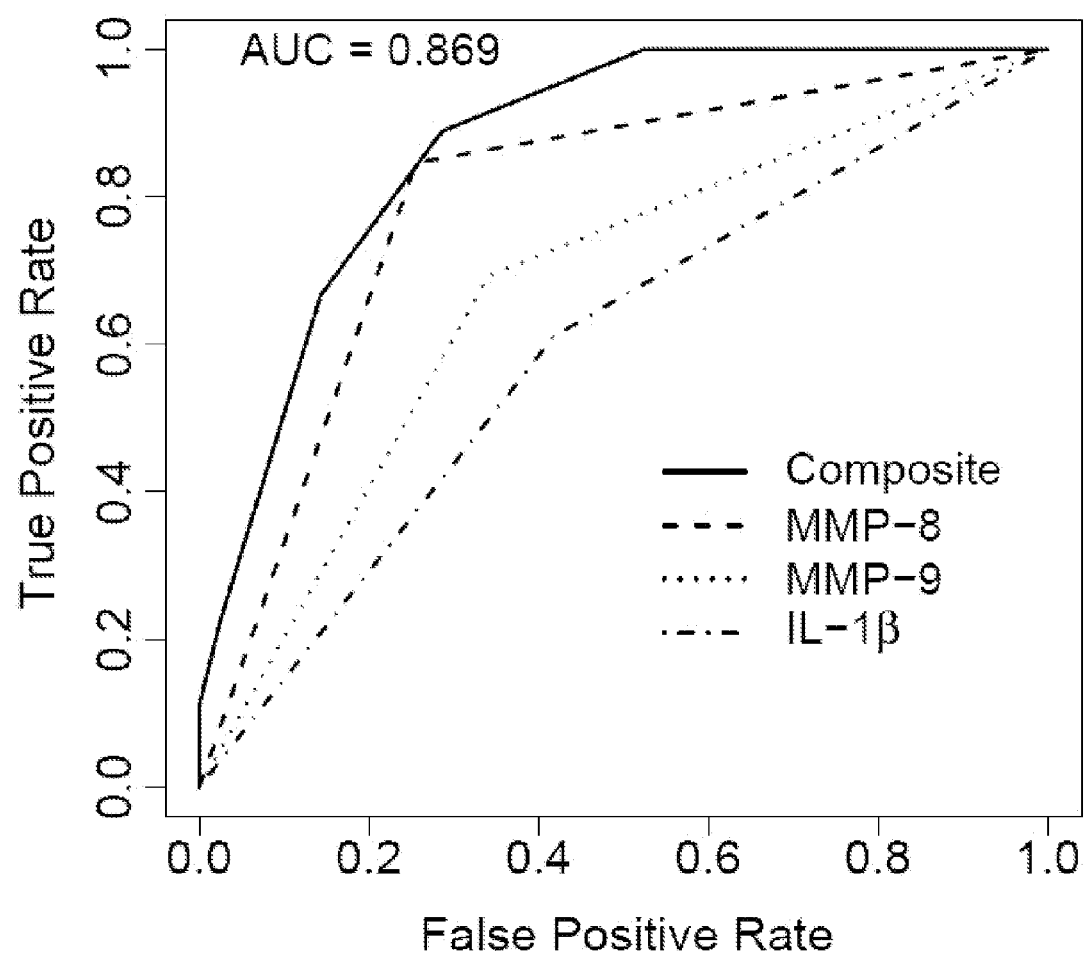
FIG. 3 depicts a receiver operating characteristic curve (ROC) and area under the curve data for the combination of MMP-8, MMP-9 and IL-1β.
Figure 4:
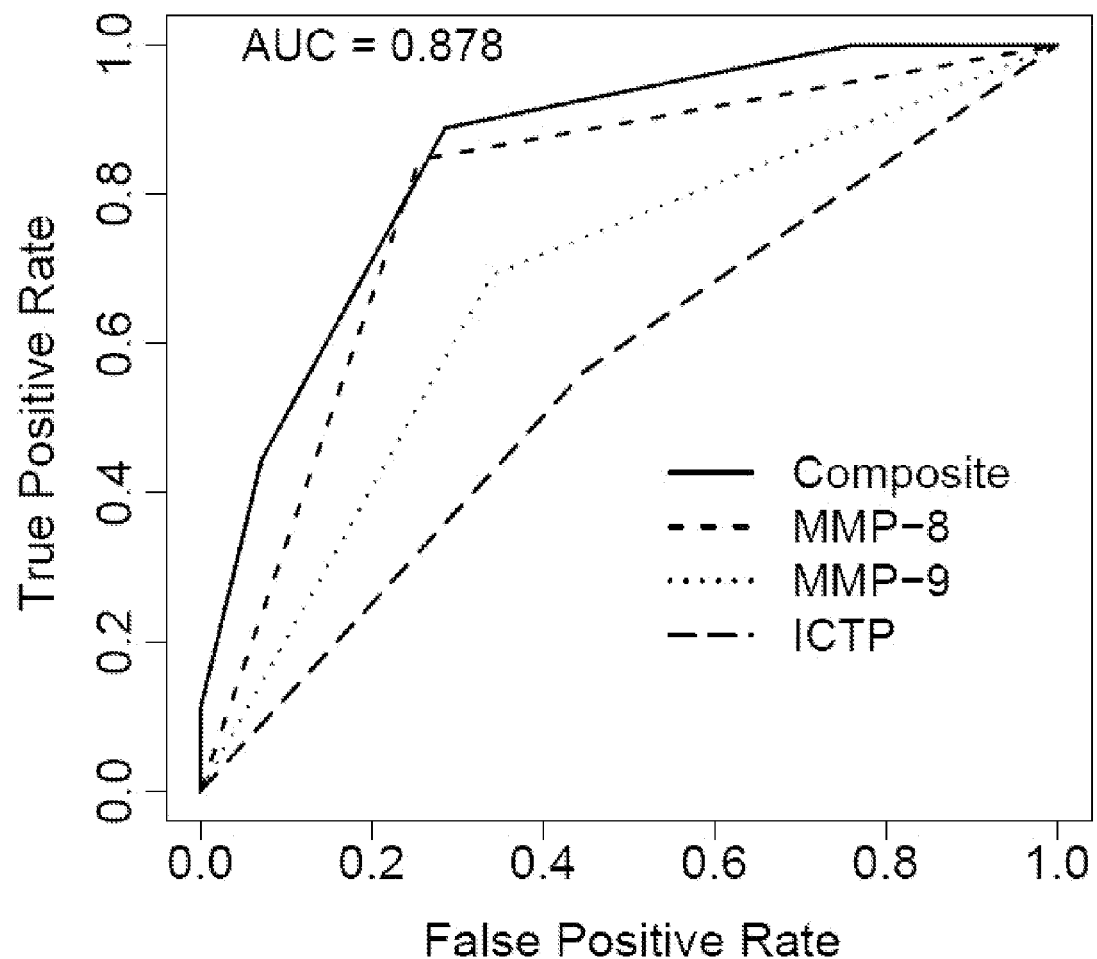
FIG. 4 depicts a receiver operating characteristic curve (ROC) and area under the curve data for the combination of MMP-8, MMP-9 and ICTP.
Figure 5:
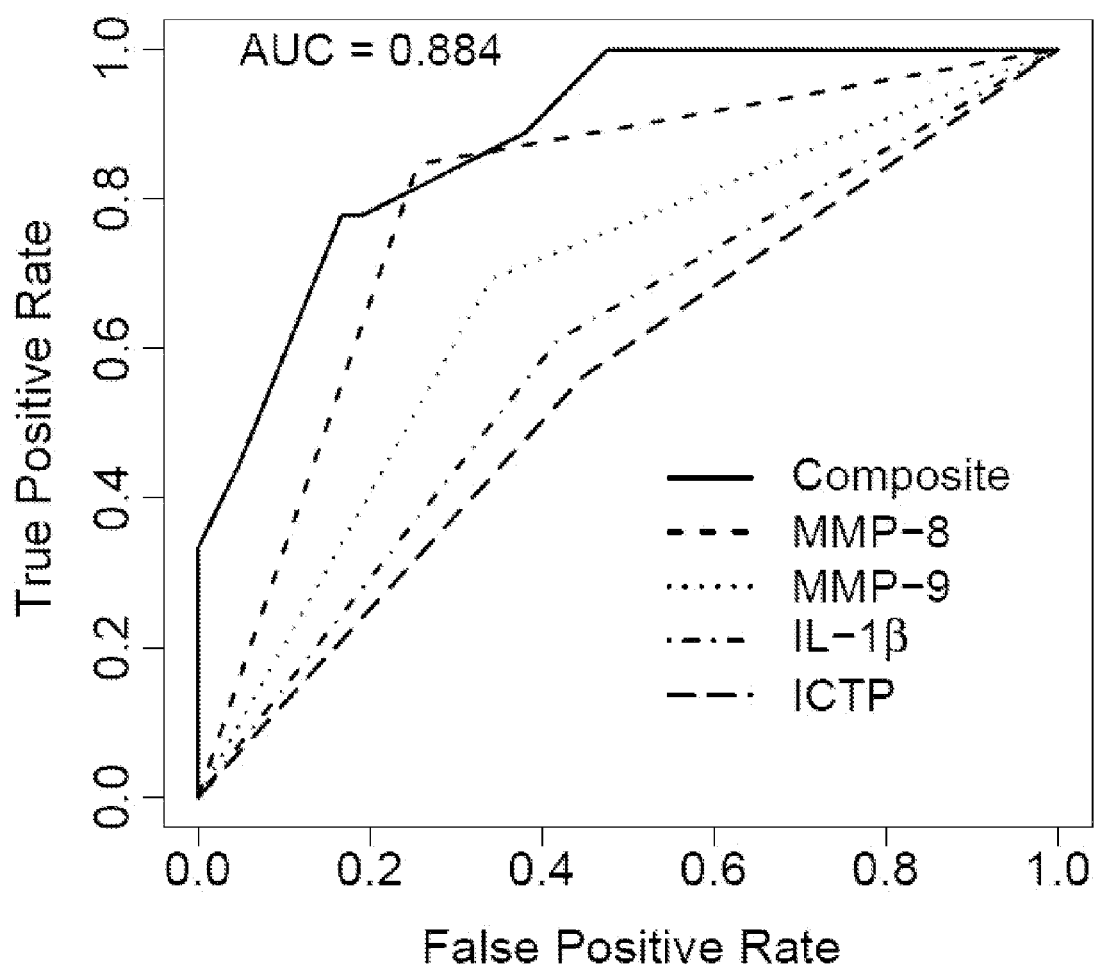
FIG. 5 depicts a receiver operating characteristic curve (ROC) and area under the curve data for the combination of MMP-8, MMP-9, IL-1β and ICTP.
Figure 6:
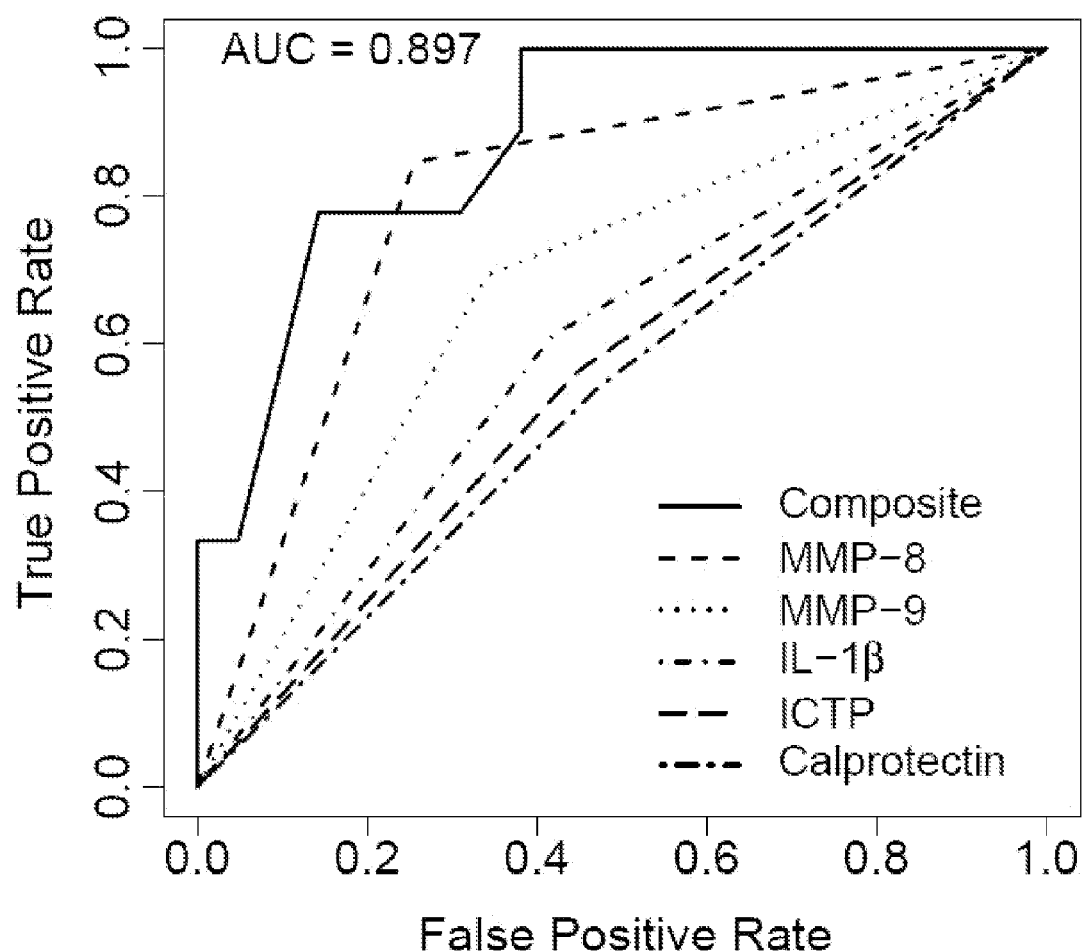
FIG. 6 depicts a receiver operating characteristic curve (ROC) and area under the curve data for the combination of MMP-8, MMP-9, IL-1β, ICTP and Calprotectin.

Demonstrated herein is a method using combinations of 14 pro-inflammatory and bone-specific markers from patient samples coupled with plaque biofilm pathogens (collectively referred to herein as "biomarkers" and used interchangeably) for the identification of periodontal disease. This novel combinatorial approach resulted in robust probability predictions of periodontitis in human subjects.

As used herein, "probability" is a calculated numerical likelihood based on an AUC value derived from a ROC curve and not simply a vague likelihood of a disease state.

As used herein, "oral disease" includes periodontal disease, peri-implant disease or any other gingival disease.

As used herein, the term "biomarker" means a substance that is measured objectively and evaluated as an indicator of normal biologic processes, pathogenic processes, or pharmacologic responses to a therapeutic intervention.

Provided herein is a method to accurately identify clinical signs of periodontal disease by a multi-analyte measurement of salivary biomarkers indicative of periodontitis. The described approach evaluates multiple analytes in oral fluids that, when combined, identify and permit calculation of a probability of the patient disease state. Supporting data demonstrate that the biomarkers, for example, matrix metalloproteinase-8 (MMP-8), matrix metalloproteinase-9 (MMP-9), pyridinoline-cross-linked carboxyterminal telopeptide of type collagen (ICTP), interleukin-1 beta (IL-1) and calprotectin as well as other biomarkers described herein used in various permutations result in a high level of prediction of periodontal disease status is achieved. Various combinations of the foregoing biomarkers were analyzed using a "receiver operating characteristics curve" (herein after "ROC"). A ROC curve is a graphical plot of the sensitivity versus (1-specificity) for a binary classifier or diagnostic system as its discrimination threshold is varied. The model maps outcomes into classes or groups. The classifier or "diagnosis" may be a continuous output of values in which the boundary between classes is determined by a threshold value, or it may be a discrete label indicating one of a limited number of outcomes (typically two, e.g., positive or negative). For a binary (two-class) predictive problem in which the classes are identified as either positive (p) or negative (n) there are four possible outcomes. If the outcome from a prediction is p and the actual value is also p, then it is called a true positive (TP); however if the actual value is n then it is said a false positive (FP). Conversely, a true negative has occurred when both the prediction outcome and the actual value are n, and false negative is when the prediction outcome is n while the actual value is p. The ROC curve displays the outcomes graphically by plotting the fraction of true positive results versus the fraction of false positive results and the area under the curve (AUC) of this plot provides a relative measure of the accuracy of the diagnosis, or the probability of oral disease. In particular, the closer the ROC curve follows the left-hand border and then the top border of the plot, the more accurate the diagnosis, while conversely the closer the curve comes to the 45-degree diagonal between the plot axes, the less accurate the diagnosis.

In general, ROC curves and AUC values are generated as follows. For a given sample of subjects, some of whom are healthy and some of whom are diseased, we have measured the value of a biomarker "Y" for each of the subjects, and we assume that higher values of "Y" are more indicative of disease. Next, a value "c" is chosen. For this value of "c", a pair of values (FPF, TPF) are computed, in which $$FPF = \text{false positive fraction} \qquad (1)$$
$$= \text{percentage of healthy subjects}$$
$$\text{with a "}Y\text{" value above "}c\text{"}$$

$$TPF = \text{true positive fraction} \qquad (2)$$
$$= \text{percentage of diseased subjects}$$
$$\text{with a "}Y\text{" value above "}c\text{"}$$

(FPF, TPF) is then generated for a continuum of values of "c" and then a scatterplot of these pairs is produced, with FPF on the x-axis and TPF on the y-axis. The curve that connects the points in this scatterplot is known as a receiver operating characteristic (ROC) curve.

The area under the ROC curve is referred to as the AUC and can be computed using the standard trapezoidal rule. It is also well-established that the value of AUC derived from the trapezoidal rule is equivalent to the Mann-Whitney U-statistic used to compare the median values of "Y" between healthy and diseased subjects. AUC values range from 0.5, which indicates that "Y" is useless for predicting disease, and 1.0, which indicates that "Y" is perfect for predicting disease.

The biomarkers discussed hereinabove individually demonstrate a high AUC and were used in determining the probability of periodontitis, if measured solely by AUC. In addition, the utilization of a classification and regression tree analysis (CART) shown in FIG. 7 determined multiple combinations of biomarkers that can best discriminate among various disease states. This method allows highly accurate measures of disease status leading to accurate diagnostic indices (high sensitivity, specificity) (>0.9) and strong and significant odds ratios for disease classification prediction (OR>20). Further, disclosure is included regarding a lab-on-a-chip demonstration of a diagnostic developed for one of these putative biomarkers (MMP-8) in saliva.

As recently reviewed, these biomarkers represent three distinct phases of periodontal disease—periodontal tissue inflammation, matrix degradation and alveolar bone resorption (Kinney et al., 2007, Ann N Y Acad Sci 1098: 230-251). The complementation of the dataset with subgingival biofilm proportions supplements the microbe-host influences on periodontal disease identification to accepted clinical measures of disease. These results describe the development of disease signatures for periodontitis using rapid diagnostic techniques.

During the initiation of an inflammatory response in the periodontal connective tissue, numerous cytokines such as PGE$_2$, IL-1β, IL-6, or TNF-α are released from cells of the junctional epithelia, connective tissue fibroblasts, and macrophages. Additionally, a number of enzymes such as MMP-8, MMP-9, or calprotectin are produced by PMNs and osteoclasts, leading to the degradation of connective tissue collagen and alveolar bone. During connective tissue inflammation and following bone resorption, cytokines and bone resorptive/turnover proteins migrate towards the gingival sulcus or periodontal pocket and further into GCF where they are released into and contribute to whole saliva. The host-cell-derived matrix metalloproteinases MMP-8 and MMP-9 are believed to mediate, to a substantial extent, the matrix-destroying events during the stages of periodontal disease.

Biostatistical methods for the quality assessment of biomarkers today consist of determining if one single biomarker has both adequate reliability (repeatability) and validity for its use in diagnostic applications (Looney, 2004, Statistical Methods for Assessing Biomarkers. In: Looney S W, editor. Biostatistical Methods. Louisville: Humana Press, Inc Baker & Taylor. pp. 81-106). With previous research on the detection of periodontal biomarkers in GCF, both reliability and validity have been well demonstrated for all the 14 biomarkers selected in this study. The individual correlation of each biomarker with disease via receiver operating characteristic (ROC) curves and nonparametric estimates of the area under the ROC curve (AUC) was assessed from subjects above the selected threshold of each biomarker.

Specific biofilm organisms or exposures may have the capacity to affect the "inflammatory set point" of the local tissues in certain patients via epigenetic mechanisms (Bobetsis et al., 2007, J Dent Res 86: 169-174; Kornman et al., 2002, Re: A critical assessment of interleukin-1 (IL-1) genotyping when used in a genetic susceptibility test for severe chronic periodontitis. Greenstein G, Hart T C (2002; 73:231-247). J Periodontol 73: 1553-1556; author reply 1556-1558). Thus, the utilization of rapid POC diagnostics that identify disease in the concept of the host-microbe interaction is demonstrated herein to lead to more rationally-tailored therapeutic strategies. The highest diagnostic accuracy in disease identification was noted when MMP-8 or MMP-9 was coupled with "red complex" periodontal organisms *T. denticola, P. gingivalis* or *T. forsythia* (Socransky et al., 1998, J Clin Periodontol 25: 134-144). The concept of MMP-8 as a diagnostic has been well described (Herr et al., 2007, Proc Natl Acad Sci USA 104: 5268-5273; Christodoulides et al., 2007, Ann N Y Acad Sci 1098: 411-428; Golub et al., 1997, Inflamm Res 46: 310-319; Kinane et al., 2003, J Periodontal Res 38: 400-404; Prescher et al., 2007, Ann N Y Acad Sci 1098: 493-495) and the linkage between red complex bacteria and collagen destruction, previously reported (Oringer et al., 1998, Clin Oral Implants Res 9: 365-373; Palys et al., 1998, J Clin Periodontol 25: 865-871). The red complex bacteria are known for their potent ability to display trypsin-like enzyme activity that are responsible for destroying collagen matrices (Loesche et al., 1987, J Periodontol 58: 266-273). Thus, these data substantiate the combinatorial utilization of MMP-destroying enzymes and corresponding initiating pathogens such as *T. denticola* for periodontal disease identification. The data presented herein now support how the coupling of this information may lead to more accurate periodontal diagnoses from a biologic standpoint.

The utility of the methods provided is also demonstrated by the use of the combinations of biomarker levels to generate an AUC probability value that can diagnose oral disease. This probability value is useful in the diagnosis, determination of the susceptibility to, determination of the progression of, and determination of the effectiveness of treatment for oral disease.

Biomarkers contemplated for use in the present invention include but are not limited to *Aggregatibacter actinomycetemcomitans, Campylobacter rectus, Fusobacterium nucleatum, Prevotella intermedia, Porphyromonas gingivalis, Tannerella forsythia, Treponema denticola*, matrix metalloproteinase-8 (MMP-8), matrix metalloproteinase-9 (MMP-9), osteoprotegerin (OPG), type I collagen pyridinoline cross-linked telopeptide (ICTP), interleukin-1 beta (IL-1β), interleukin-6 (IL-6), interleukin-4 (IL-4), interleukin-10 (IL-10), interleukin-2 (IL-2), interleukin-13 (IL-13), calprotectin, and tumor necrosis factor α (TNFα).

The biomarker levels generated by the methods of the present invention are contemplated for use in combination to calculate AUC probability values that are indicative of relative disease state. Combinations of biomarkers for use in the present invention include but are not limited to those set out in Tables 1, 2 and 3 below.

TABLE 1

Biomarker combinations resulting in an AUC (probability) value greater than at least 70%.

| Signature | AUC |
|---|---|
| Calprotectin + OPG + *P. intermedia* | 0.79 |
| MMP9 + IL13 + *P. intermedia* | 0.79 |
| MMP9 + *P. intermedia* | 0.79 |
| ICTP + TNFa + *P. intermedia* + *F. nucleatum* | 0.79 |
| *P. gingivalis* + TNFa | 0.79 |
| Calprotectin + IL13 + *P. intermedia* | 0.79 |
| MMP9 + IL10 + *P. intermedia* | 0.79 |
| Calprotectin + IL2 + *P. intermedia* | 0.79 |
| MMP8 + Calprotectin + *C. rectus* | 0.79 |
| Calprotectin + IL6 + *P. intermedia* | 0.79 |
| Calprotectin + IL1beta + *P. intermedia* | 0.79 |
| MMP9 + IL4 + *P. intermedia* | 0.79 |
| Calprotectin + IL10 + *P. intermedia* | 0.79 |
| IL1beta + TNFa + *P. intermedia* + *F. nucleatum* | 0.79 |
| IL10 + TNFa + *P. intermedia* + *F. nucleatum* | 0.79 |
| *P. gingivalis* | 0.78 |
| Calprotectin + IL4 + *P. intermedia* | 0.78 |
| Calprotectin + *P. intermedia* | 0.78 |
| MMP8 + ICTP + *F. nucleatum* + *C. rectus* | 0.78 |
| ICTP + IL4 + *P. intermedia* + *F. nucleatum* | 0.78 |
| IL6 + ICTP + *P. intermedia* + *F. nucleatum* | 0.78 |
| ICTP + IL1beta + *P. intermedia* + *F. nucleatum* | 0.78 |
| MMP9 + ICTP + *F. nucleatum* + *C. rectus* | 0.78 |
| ICTP + IL2 + *P. intermedia* + *F. nucleatum* | 0.78 |
| IL2 + TNFa + *P. intermedia* + *F. nucleatum* | 0.78 |

TABLE 1-continued

Biomarker combinations resulting in an AUC (probability) value greater than at least 70%.

| Signature | AUC |
|---|---|
| ICTP + TNFa + P. intermedia + C. rectus | 0.78 |
| ICTP + IL10 + P. intermedia + F. nucleatum | 0.78 |
| IL13 + TNFa + P. intermedia + F. nucleatum | 0.78 |
| MMP8 + ICTP + C. rectus | 0.78 |
| ICTP + IL13 + P. intermedia + F. nucleatum | 0.78 |
| MMP9 + ICTP + C. rectus | 0.78 |
| ICTP + P. intermedia + F. nucleatum | 0.78 |
| OPG + ICTP + P. intermedia + F. nucleatum | 0.78 |
| IL6 + TNFa + P. intermedia + F. nucleatum | 0.78 |
| TNFa + P. intermedia + F. nucleatum | 0.78 |
| OPG + TNFa + P. intermedia + F. nucleatum | 0.77 |
| Calprotectin + IL10 + F. nucleatum + C. rectus | 0.77 |
| IL6 + ICTP + P. intermedia + C. rectus | 0.77 |
| Calprotectin + OPG + F. nucleatum + C. rectus | 0.77 |
| ICTP + TNFa + P. intermedia | 0.77 |
| IL13 + IL4 + P. intermedia + F. nucleatum | 0.77 |
| MMP9 + TNFa + F. nucleatum + C. rectus | 0.77 |
| IL4 + TNFa + P. intermedia + C. rectus | 0.77 |
| MMP9 + TNFa + C. rectus | 0.77 |
| OPG + IL4 + P. intermedia + F. nucleatum | 0.77 |
| OPG + ICTP + P. intermedia + C. rectus | 0.77 |
| ICTP + IL4 + P. intermedia + C. rectus | 0.77 |
| Calprotectin + MMP9 + F. nucleatum | 0.77 |
| ICTP + IL10 + P. intermedia + C. rectus | 0.77 |
| IL2 + IL4 + P. intermedia + F. nucleatum | 0.77 |
| IL4 + P. intermedia + F. nucleatum | 0.77 |
| ICTP + IL1beta + P. intermedia + C. rectus | 0.77 |
| MMP9 + IL6 + F. nucleatum + C. rectus | 0.77 |
| IL10 + IL2 + P. intermedia + F. nucleatum | 0.77 |
| MMP9 + IL6 + C. rectus | 0.77 |
| IL6 + IL10 + P. intermedia + F. nucleatum | 0.77 |
| IL6 + IL4 + P. intermedia + F. nucleatum | 0.77 |
| IL1beta + IL4 + P. intermedia + F. nucleatum | 0.77 |
| Calprotectin + IL1beta + F. nucleatum + C. rectus | 0.77 |
| ICTP + IL2 + P. intermedia + C. rectus | 0.77 |
| IL10 + IL4 + P. intermedia + F. nucleatum | 0.77 |
| ICTP + P. intermedia + C. rectus | 0.77 |
| IL4 + TNFa + P. intermedia | 0.77 |
| ICTP + IL13 + P. intermedia + C. rectus | 0.77 |
| OPG + IL2 + P. intermedia + F. nucleatum | 0.76 |
| IL1beta + IL10 + P. intermedia + F. nucleatum | 0.76 |
| P. intermedia + F. nucleatum + C. rectus | 0.76 |
| MMP8 + TNFa + F. nucleatum + C. rectus | 0.76 |
| IL10 + P. intermedia + F. nucleatum | 0.76 |
| MMP9 + OPG + F. nucleatum + C. rectus | 0.76 |
| OPG + IL10 + P. intermedia + F. nucleatum | 0.76 |
| IL1beta + IL13 + P. intermedia + F. nucleatum | 0.76 |
| IL2 + IL13 + P. intermedia + F. nucleatum | 0.76 |
| MMP9 + IL2 + F. nucleatum + C. rectus | 0.76 |
| MMP9 + IL13 + F. nucleatum + C. rectus | 0.76 |
| OPG + IL1beta + P. intermedia + F. nucleatum | 0.76 |
| IL1beta + P. intermedia + F. nucleatum | 0.76 |
| IL6 + ICTP + P. intermedia | 0.76 |
| IL6 + IL1beta + P. intermedia + F. nucleatum | 0.76 |
| IL1beta + IL2 + P. intermedia + F. nucleatum | 0.76 |
| Calprotectin + IL6 + F. nucleatum + C. rectus | 0.76 |
| IL10 + IL13 + P. intermedia + F. nucleatum | 0.76 |
| IL6 + P. intermedia + F. nucleatum | 0.76 |
| MMP8 + MMP9 + C. rectus | 0.76 |
| ICTP + IL4 + P. intermedia | 0.76 |
| OPG + IL6 + P. intermedia + F. nucleatum | 0.76 |
| IL6 + IL2 + P. intermedia + F. nucleatum | 0.76 |
| IL10 + TNFa + P. intermedia + C. rectus | 0.76 |
| OPG + P. intermedia + F. nucleatum | 0.76 |
| IL2 + P. intermedia + F. nucleatum | 0.76 |
| ICTP + IL1beta + P. intermedia | 0.76 |
| Calprotectin + ICTP + F. nucleatum + C. rectus | 0.76 |
| MMP8 + TNFa + C. rectus | 0.76 |
| MMP8 + MMP9 + F. nucleatum + C. rectus | 0.76 |
| MMP9 + IL1beta + F. nucleatum + C. rectus | 0.76 |
| MMP8 + IL10 + F. nucleatum + C. rectus | 0.76 |
| Calprotectin + IL4 + F. nucleatum + C. rectus | 0.76 |
| IL13 + P. intermedia + F. nucleatum | 0.76 |
| MMP9 + OPG + C. rectus | 0.76 |
| MMP9 + IL1beta + C. rectus | 0.76 |
| IL1beta + TNFa + P. intermedia | 0.76 |
| MMP9 + IL10 + F. nucleatum + C. rectus | 0.76 |
| OPG + IL13 + P. intermedia + F. nucleatum | 0.76 |
| IL6 + IL13 + P. intermedia + F. nucleatum | 0.76 |
| IL1beta + TNFa + P. intermedia + C. rectus | 0.76 |
| MMP9 + IL10 + C. rectus | 0.76 |
| MMP9 + IL4 + F. nucleatum + C. rectus | 0.76 |
| P. intermedia + F. nucleatum | 0.76 |
| ICTP + IL13 + P. intermedia | 0.76 |
| IL6 + TNFa + P. intermedia + C. rectus | 0.76 |
| IL6 + TNFa + P. intermedia | 0.76 |
| IL2 + TNFa + P. intermedia + C. rectus | 0.76 |
| Calprotectin + IL13 + F. nucleatum + C. rectus | 0.76 |
| MMP8 + IL10 + C. rectus | 0.76 |
| IL2 + TNFa + P. intermedia | 0.76 |
| MMP8 + IL6 + F. nucleatum + C. rectus | 0.76 |
| MMP8 + IL13 + F. nucleatum + C. rectus | 0.76 |
| MMP9 + F. nucleatum + C. rectus | 0.76 |
| MMP9 + IL2 + C. rectus | 0.76 |
| ICTP + IL2 + P. intermedia | 0.76 |
| MMP9 + IL13 + C. rectus | 0.76 |
| MMP9 + IL4 + C. rectus | 0.76 |
| MMP8 + IL4 + F. nucleatum + C. rectus | 0.76 |
| ICTP + IL10 + P. intermedia | 0.76 |
| IL10 + TNFa + P. intermedia | 0.76 |
| Calprotectin + OPG + C. rectus | 0.76 |
| MMP8 + IL1beta + F. nucleatum + C. rectus | 0.76 |
| TNFa + P. intermedia + C. rectus | 0.76 |
| IL13 + IL4 + P. intermedia + C. rectus | 0.76 |
| ICTP + P. intermedia | 0.76 |
| IL6 + IL4 + P. intermedia + C. rectus | 0.76 |
| MMP8 + ICTP + F. nucleatum | 0.75 |
| OPG + ICTP + P. intermedia | 0.75 |
| MMP8 + IL6 + C. rectus | 0.75 |
| MMP8 + IL1beta + C. rectus | 0.75 |
| MMP8 + OPG + F. nucleatum + C. rectus | 0.75 |
| IL13 + TNFa + P. intermedia + C. rectus | 0.75 |
| OPG + TNFa + P. intermedia + C. rectus | 0.75 |
| Calprotectin + MMP9 | 0.75 |
| MMP8 + Calprotectin + F. nucleatum | 0.75 |
| MMP9 + C. rectus | 0.75 |
| MMP8 + IL13 + C. rectus | 0.75 |
| MMP8 + F. nucleatum + C. rectus | 0.75 |
| MMP8 + IL4 + C. rectus | 0.75 |
| OPG + TNFa + P. intermedia | 0.75 |
| MMP8 + OPG + C. rectus | 0.75 |
| Calprotectin + TNFa + F. nucleatum + C. rectus | 0.75 |
| MMP8 + IL2 + F. nucleatum + C. rectus | 0.75 |
| IL6 + IL1beta + P. intermedia + C. rectus | 0.75 |
| TNFa + P. intermedia | 0.75 |
| IL4 + P. intermedia + C. rectus | 0.75 |
| Calprotectin + F. nucleatum + C. rectus | 0.75 |
| IL13 + TNFa + P. intermedia | 0.75 |
| IL10 + IL4 + P. intermedia + C. rectus | 0.75 |
| IL2 + IL4 + P. intermedia + C. rectus | 0.75 |
| MMP8 + C. rectus | 0.75 |
| MMP8 + IL2 + C. rectus | 0.75 |
| Calprotectin + IL6 + C. rectus | 0.75 |
| IL13 + IL4 + P. intermedia | 0.75 |
| IL6 + IL13 + P. intermedia + C. rectus | 0.75 |
| IL1beta + IL4 + P. intermedia + C. rectus | 0.75 |
| MMP9 + TNFa + F. nucleatum | 0.75 |
| OPG + IL4 + P. intermedia + C. rectus | 0.75 |
| Calprotectin + IL2 + F. nucleatum + C. rectus | 0.74 |
| IL1beta + IL13 + P. intermedia | 0.74 |
| IL10 + IL13 + P. intermedia + C. rectus | 0.74 |
| IL6 + IL13 + P. intermedia | 0.74 |
| IL6 + P. intermedia + C. rectus | 0.74 |
| MMP8 + Calprotectin | 0.74 |
| IL6 + IL2 + P. intermedia + C. rectus | 0.74 |
| IL10 + P. intermedia + C. rectus | 0.74 |
| MMP8 + TNFa + F. nucleatum | 0.74 |
| MMP9 + ICTP + F. nucleatum | 0.74 |
| MMP8 + ICTP | 0.74 |
| IL10 + IL2 + P. intermedia + C. rectus | 0.74 |

TABLE 1-continued

Biomarker combinations resulting in an AUC (probability) value greater than at least 70%.

| Signature | AUC |
|---|---|
| Calprotectin + IL10 + C. rectus | 0.74 |
| IL6 + IL4 + P. intermedia | 0.74 |
| IL6 + IL10 + P. intermedia + C. rectus | 0.74 |
| IL1beta + P. intermedia + C. rectus | 0.74 |
| IL6 + IL1beta + P. intermedia | 0.74 |
| IL10 + IL13 + P. intermedia | 0.74 |
| IL13 + P. intermedia + C. rectus | 0.74 |
| OPG + IL4 + P. intermedia | 0.74 |
| IL2 + IL13 + P. intermedia + C. rectus | 0.74 |
| P. intermedia + C. rectus | 0.74 |
| OPG + IL2 + P. intermedia + C. rectus | 0.74 |
| IL10 + IL4 + P. intermedia | 0.74 |
| OPG + IL1beta + P. intermedia + C. rectus | 0.74 |
| OPG + IL10 + P. intermedia + C. rectus | 0.74 |
| OPG + IL13 + P. intermedia + C. rectus | 0.74 |
| IL1beta + IL4 + P. intermedia | 0.74 |
| IL1beta + IL10 + P. intermedia + C. rectus | 0.74 |
| Calprotectin + ICTP + C. rectus | 0.74 |
| IL2 + IL13 + P. intermedia | 0.74 |
| IL1beta + IL13 + P. intermedia + C. rectus | 0.74 |
| IL1beta + IL2 + P. intermedia + C. rectus | 0.74 |
| IL2 + P. intermedia + C. rectus | 0.74 |
| OPG + IL1beta + P. intermedia | 0.74 |
| OPG + P. intermedia + C. rectus | 0.74 |
| MMP8 + IL10 + F. nucleatum | 0.74 |
| OPG + IL13 + P. intermedia | 0.74 |
| IL4 + P. intermedia | 0.73 |
| MMP9 + IL10 + F. nucleatum | 0.73 |
| IL1beta + IL10 + P. intermedia | 0.73 |
| IL13 + P. intermedia | 0.73 |
| IL2 + IL4 + P. intermedia | 0.73 |
| IL1beta + P. intermedia | 0.73 |
| MMP8 + OPG + F. nucleatum | 0.73 |
| MMP8 + IL1beta + F. nucleatum | 0.73 |
| IL1beta + IL2 + P. intermedia | 0.73 |
| MMP9 + TNFa | 0.73 |
| MMP9 + ICTP | 0.73 |
| MMP8 + IL4 + F. nucleatum | 0.73 |
| IL6 + P. intermedia | 0.73 |
| MMP9 + IL1beta + F. nucleatum | 0.73 |
| OPG + IL6 + P. intermedia + C. rectus | 0.73 |
| OPG + IL2 + P. intermedia | 0.73 |
| IL6 + ICTP + F. nucleatum + C. rectus | 0.73 |
| IL6 + IL2 + P. intermedia | 0.73 |
| MMP9 + IL4 + F. nucleatum | 0.73 |
| OPG + IL10 + P. intermedia | 0.73 |
| Calprotectin + IL1beta + C. rectus | 0.73 |
| MMP8 + IL2 + F. nucleatum | 0.73 |
| Calprotectin + IL4 + C. rectus | 0.73 |
| MMP8 + IL6 + F. nucleatum | 0.73 |
| MMP9 + OPG + F. nucleatum | 0.73 |
| OPG + IL6 + P. intermedia | 0.73 |
| OPG + P. intermedia | 0.73 |
| IL10 + IL2 + P. intermedia | 0.73 |
| IL6 + IL10 + P. intermedia | 0.73 |
| MMP8 + TNFa | 0.73 |
| MMP8 + MMP9 + F. nucleatum | 0.73 |
| MMP8 + IL13 + F. nucleatum | 0.73 |
| MMP9 + IL6 + F. nucleatum | 0.73 |
| MMP9 + IL13 + F. nucleatum | 0.73 |
| MMP8 + OPG | 0.72 |
| IL2 + P. intermedia | 0.72 |
| IL10 + P. intermedia | 0.72 |
| P. intermedia | 0.72 |
| MMP9 + F. nucleatum | 0.72 |
| MMP8 + F. nucleatum | 0.72 |
| MMP9 + OPG | 0.72 |
| MMP9 + IL2 + F. nucleatum | 0.72 |
| IL6 + ICTP + C. rectus | 0.72 |
| MMP8 + IL1beta | 0.72 |
| Calprotectin + OPG + F. nucleatum | 0.72 |
| Calprotectin + IL13 + C. rectus | 0.72 |
| MMP8 + MMP9 | 0.72 |
| MMP8 + IL10 | 0.71 |
| MMP9 + IL1beta | 0.71 |
| IL4 + TNFa + F. nucleatum + C. rectus | 0.71 |
| ICTP + IL1beta + F. nucleatum + C. rectus | 0.71 |
| MMP9 + IL6 | 0.71 |
| MMP8 + IL4 | 0.71 |
| MMP9 + IL4 | 0.71 |
| MMP8 + IL6 | 0.71 |
| MMP8 + IL2 | 0.71 |
| MMP9 + IL10 | 0.70 |
| ICTP + IL4 + F. nucleatum + C. rectus | 0.70 |
| Calprotectin + TNFa + C. rectus | 0.70 |
| MMP9 + IL2 | 0.70 |
| ICTP + TNFa + F. nucleatum + C. rectus | 0.70 |
| ICTP + IL10 + F. nucleatum + C. rectus | 0.70 |
| IL6 + IL4 + F. nucleatum + C. rectus | 0.70 |
| MMP9 + IL13 | 0.70 |
| MMP8 + IL13 | 0.70 |
| Calprotectin + IL2 + C. rectus | 0.70 |
| Calprotectin + IL6 + F. nucleatum | 0.70 |
| Calprotectin + C. rectus | 0.70 |
| IL6 + TNFa + F. nucleatum + C. rectus | 0.70 |
| ICTP + IL13 + F. nucleatum + C. rectus | 0.70 |
| MMP8 | 0.70 |
| MMP9 | 0.70 |

TABLE 2

Biomarker combinations resulting in an AUC (probability) value great than at least 80%.

| Signature | AUC |
|---|---|
| T. denticola + TNFa + P. intermedia | 0.89 |
| Calprotectin + MMP9 + P. gingivalis | 0.89 |
| MMP8 + T. forsythia + IL1beta + F. nucleatum | 0.89 |
| MMP9 + OPG + P. gingivalis + T. forsythia | 0.89 |
| MMP9 + P. gingivalis + T. denticola + IL10 | 0.89 |
| MMP9 + T. forsythia + ICTP + C. rectus | 0.89 |
| MMP9 + OPG + T. denticola | 0.89 |
| MMP8 + P. gingivalis + ICTP + F. nucleatum | 0.89 |
| Calprotectin + P. gingivalis + IL6 + P. intermedia | 0.89 |
| Calprotectin + T. forsythia + IL4 + P. intermedia | 0.89 |
| T. forsythia + T. denticola + C. rectus | 0.89 |
| Calprotectin + MMP9 + T. denticola | 0.89 |
| MMP9 + T. denticola + IL1beta | 0.89 |
| T. denticola + ICTP + IL13 | 0.89 |
| Calprotectin + MMP9 + T. forsythia + F. nucleatum | 0.89 |
| Calprotectin + T. forsythia + IL10 + P. intermedia | 0.89 |
| MMP9 + T. forsythia + IL6 + P. intermedia | 0.89 |
| OPG + T. denticola + IL6 + C. rectus | 0.89 |
| T. forsythia + T. denticola + IL10 + IL13 | 0.89 |
| T. forsythia + ICTP + IL13 + P. intermedia | 0.89 |
| T. denticola + IL6 + IL1beta + P. intermedia | 0.89 |
| T. denticola + IL6 + TNFa + C. rectus | 0.89 |
| T. denticola + IL1beta + TNFa + P. intermedia | 0.89 |
| T. denticola + IL4 + TNFa + P. intermedia | 0.89 |
| T. denticola + IL4 + P. intermedia | 0.89 |
| Calprotectin + MMP9 + P. gingivalis + F. nucleatum | 0.89 |
| MMP8 + OPG + P. gingivalis + T. forsythia | 0.89 |
| MMP8 + T. denticola + IL2 + F. nucleatum | 0.89 |
| OPG + T. denticola + IL10 + P. intermedia | 0.89 |
| T. denticola + IL1beta + IL2 + P. intermedia | 0.89 |
| MMP9 + P. gingivalis + IL10 + P. intermedia | 0.89 |
| MMP9 + T. denticola + IL10 + F. nucleatum | 0.89 |
| OPG + T. denticola + IL2 + P. intermedia | 0.89 |
| T. denticola + IL6 + IL4 + C. rectus | 0.89 |
| T. denticola + IL1beta + IL4 + P. intermedia | 0.89 |
| T. denticola + ICTP + IL2 | 0.89 |
| MMP8 + Calprotectin + P. gingivalis + C. rectus | 0.89 |
| Calprotectin + T. forsythia + P. intermedia | 0.89 |
| MMP9 + T. forsythia + P. intermedia | 0.89 |
| MMP8 + Calprotectin + T. denticola | 0.89 |
| MMP8 + Calprotectin + T. forsythia + F. nucleatum | 0.89 |

TABLE 2-continued

Biomarker combinations resulting in an AUC (probability) value great than at least 80%.

| Signature | AUC |
|---|---|
| MMP8 + T. forsythia + ICTP + F. nucleatum | 0.89 |
| MMP8 + T. denticola + IL10 + F. nucleatum | 0.89 |
| Calprotectin + T. forsythia + IL2 + P. intermedia | 0.89 |
| MMP9 + T. forsythia + IL1beta + C. rectus | 0.89 |
| OPG + T. denticola + IL10 + C. rectus | 0.89 |
| P. gingivalis + T. forsythia + P. intermedia | 0.89 |
| T. denticola + ICTP + TNFa | 0.89 |
| MMP8 + Calprotectin + T. forsythia + C. rectus | 0.89 |
| Calprotectin + T. forsythia + IL6 + P. intermedia | 0.89 |
| Calprotectin + T. forsythia + IL6 + C. rectus | 0.89 |
| T. forsythia + IL13 + TNFa + P. intermedia | 0.89 |
| T. denticola + IL1beta + IL10 + P. intermedia | 0.89 |
| T. denticola + IL6 + IL2 + C. rectus | 0.89 |
| MMP8 + MMP9 + P. gingivalis + T. forsythia | 0.89 |
| T. denticola + IL6 + IL1beta + C. rectus | 0.89 |
| MMP9 + T. forsythia + IL1beta + F. nucleatum | 0.89 |
| OPG + T. forsythia + T. denticola + IL13 | 0.89 |
| T. forsythia + ICTP + IL1beta + P. intermedia | 0.89 |
| T. denticola + IL6 + P. intermedia | 0.89 |
| T. denticola + IL6 + C. rectus | 0.89 |
| MMP9 + T. denticola + IL2 + F. nucleatum | 0.89 |
| P. gingivalis + IL6 + ICTP + P. intermedia | 0.89 |
| T. forsythia + ICTP + TNFa + P. intermedia | 0.89 |
| T. denticola + IL6 + IL10 + P. intermedia | 0.89 |
| T. denticola + IL6 + IL10 + C. rectus | 0.89 |
| T. denticola + IL1beta + P. intermedia | 0.89 |
| MMP9 + T. denticola + TNFa + F. nucleatum | 0.89 |
| T. forsythia + ICTP + IL4 + P. intermedia | 0.89 |
| MMP8 + T. denticola + IL13 + F. nucleatum | 0.89 |
| MMP8 + T. denticola + TNFa + F. nucleatum | 0.89 |
| MMP8 + MMP9 + T. denticola + F. nucleatum | 0.89 |
| Calprotectin + T. forsythia + ICTP + C. rectus | 0.89 |
| MMP9 + T. denticola + IL6 + F. nucleatum | 0.89 |
| MMP9 + T. denticola + IL13 + F. nucleatum | 0.89 |
| MMP9 + T. denticola + IL4 + F. nucleatum | 0.89 |
| MMP8 + P. gingivalis + ICTP + C. rectus | 0.89 |
| OPG + T. denticola + IL13 + C. rectus | 0.89 |
| T. denticola + IL10 + IL2 + P. intermedia | 0.89 |
| T. denticola + IL10 + IL13 + C. rectus | 0.89 |
| MMP8 + T. denticola + IL2 | 0.89 |
| MMP8 + T. denticola + IL6 + F. nucleatum | 0.89 |
| Calprotectin + OPG + T. denticola + F. nucleatum | 0.89 |
| OPG + T. forsythia + T. denticola + TNFa | 0.89 |
| T. forsythia + T. denticola + IL2 + IL13 | 0.89 |
| T. forsythia + IL6 + IL13 + P. intermedia | 0.89 |
| MMP8 + T. denticola + F. nucleatum | 0.89 |
| MMP9 + T. denticola + F. nucleatum | 0.89 |
| MMP9 + T. denticola + TNFa | 0.89 |
| MMP9 + P. gingivalis + ICTP + C. rectus | 0.89 |
| T. forsythia + IL10 + IL13 + P. intermedia | 0.89 |
| T. denticola + IL10 + IL2 + C. rectus | 0.89 |
| T. denticola + IL2 + P. intermedia | 0.89 |
| MMP8 + T. denticola + IL4 + F. nucleatum | 0.89 |
| Calprotectin + OPG + T. forsythia + F. nucleatum | 0.89 |
| MMP9 + P. gingivalis + T. forsythia + IL2 | 0.89 |
| MMP8 + Calprotectin + P. gingivalis | 0.89 |
| MMP8 + T. forsythia + TNFa + C. rectus | 0.89 |
| MMP8 + T. denticola + IL10 | 0.89 |
| MMP8 + T. denticola + TNFa | 0.89 |
| MMP8 + Calprotectin + P. gingivalis + F. nucleatum | 0.89 |
| MMP8 + T. denticola + IL13 | 0.89 |
| Calprotectin + MMP9 + T. forsythia | 0.89 |
| MMP9 + T. denticola + IL13 | 0.89 |
| MMP9 + T. forsythia + ICTP + F. nucleatum | 0.89 |
| MMP9 + T. forsythia + IL2 + C. rectus | 0.89 |
| OPG + T. forsythia + T. denticola + IL4 | 0.89 |
| T. forsythia + ICTP + IL10 + P. intermedia | 0.89 |
| T. denticola + ICTP + IL4 | 0.89 |
| Calprotectin + P. gingivalis + T. forsythia + IL13 | 0.89 |
| OPG + T. forsythia + T. denticola + IL6 | 0.89 |
| MMP9 + P. gingivalis + T. forsythia + IL10 | 0.89 |
| T. denticola + P. intermedia | 0.89 |
| T. denticola + ICTP | 0.89 |
| MMP8 + P. gingivalis + ICTP | 0.89 |
| MMP9 + T. denticola + IL6 | 0.89 |
| MMP8 + OPG + T. forsythia + C. rectus | 0.89 |
| Calprotectin + T. forsythia + T. denticola + IL6 | 0.89 |
| MMP9 + P. gingivalis + ICTP + F. nucleatum | 0.89 |
| MMP9 + T. forsythia + TNFa + F. nucleatum | 0.89 |
| T. forsythia + ICTP + IL2 + P. intermedia | 0.89 |
| T. denticola + IL1beta + IL10 + C. rectus | 0.89 |
| T. denticola + IL10 + IL4 + C. rectus | 0.89 |
| P. gingivalis + T. denticola + C. rectus | 0.89 |
| MMP9 + T. denticola + IL2 | 0.89 |
| T. denticola + ICTP + IL1beta | 0.89 |
| MMP8 + P. gingivalis + T. forsythia + IL10 | 0.89 |
| Calprotectin + P. gingivalis + IL6 + C. rectus | 0.89 |
| Calprotectin + T. forsythia + T. denticola + IL10 | 0.89 |
| MMP9 + OPG + T. forsythia + C. rectus | 0.89 |
| OPG + T. forsythia + T. denticola + IL1beta | 0.89 |
| T. forsythia + IL1beta + IL13 + P. intermedia | 0.89 |
| T. forsythia + IL2 + IL13 + P. intermedia | 0.89 |
| T. denticola + IL10 + TNFa + C. rectus | 0.89 |
| T. denticola + IL10 + C. rectus | 0.89 |
| MMP8 + MMP9 + T. denticola | 0.89 |
| MMP9 + T. denticola + IL10 | 0.89 |
| MMP8 + T. denticola + IL6 | 0.89 |
| MMP8 + T. forsythia + TNFa + F. nucleatum | 0.89 |
| Calprotectin + T. forsythia + T. denticola + TNFa | 0.89 |
| Calprotectin + T. forsythia + ICTP + F. nucleatum | 0.89 |
| P. gingivalis + ICTP + IL13 + P. intermedia | 0.89 |
| P. gingivalis + IL10 + IL13 + P. intermedia | 0.89 |
| T. denticola + IL10 + P. intermedia | 0.89 |
| MMP9 + P. gingivalis + T. forsythia + IL6 | 0.89 |
| OPG + T. forsythia + T. denticola + IL10 | 0.89 |
| T. forsythia + IL13 + P. intermedia | 0.88 |
| MMP8 + P. gingivalis + T. forsythia + IL6 | 0.88 |
| Calprotectin + T. forsythia + T. denticola + IL1beta | 0.88 |
| OPG + T. forsythia + T. denticola + IL2 | 0.88 |
| P. gingivalis + ICTP + IL1beta + P. intermedia | 0.88 |
| T. denticola + IL1beta + IL13 + C. rectus | 0.88 |
| Calprotectin + T. forsythia + T. denticola + IL2 | 0.88 |
| P. gingivalis + ICTP + TNFa + P. intermedia | 0.88 |
| MMP9 + T. forsythia + IL4 + C. rectus | 0.88 |
| T. forsythia + IL6 + ICTP + P. intermedia | 0.88 |
| T. denticola + IL2 + IL13 + C. rectus | 0.88 |
| OPG + T. denticola + C. rectus | 0.88 |
| MMP9 + T. forsythia + IL13 + F. nucleatum | 0.88 |
| MMP9 + T. forsythia + IL13 + C. rectus | 0.88 |
| OPG + T. forsythia + ICTP + P. intermedia | 0.88 |
| OPG + T. forsythia + T. denticola | 0.88 |
| MMP8 + P. gingivalis + T. forsythia + IL2 | 0.88 |
| OPG + T. forsythia + IL13 + P. intermedia | 0.88 |
| T. forsythia + T. denticola + IL13 + IL4 | 0.88 |
| T. denticola + IL2 + TNFa + C. rectus | 0.88 |
| T. forsythia + T. denticola + IL13 | 0.88 |
| P. gingivalis + ICTP + IL10 + P. intermedia | 0.88 |
| T. forsythia + T. denticola + IL1beta + IL13 | 0.88 |
| T. forsythia + IL13 + IL4 + P. intermedia | 0.88 |
| MMP8 + T. denticola + IL4 | 0.88 |
| MMP9 + T. denticola + IL4 | 0.88 |
| P. gingivalis + IL1beta + IL13 + P. intermedia | 0.88 |
| T. forsythia + P. intermedia + F. nucleatum | 0.88 |
| MMP8 + T. forsythia + IL13 + F. nucleatum | 0.88 |
| Calprotectin + P. gingivalis + T. forsythia + ICTP | 0.88 |
| T. forsythia + T. denticola + IL2 + TNFa | 0.88 |
| MMP8 + MMP9 + T. forsythia + C. rectus | 0.88 |
| MMP8 + T. forsythia + IL13 + C. rectus | 0.88 |
| Calprotectin + T. forsythia + T. denticola + IL4 | 0.88 |
| Calprotectin + T. forsythia + IL13 + F. nucleatum | 0.88 |
| OPG + T. forsythia + IL1beta + C. rectus | 0.88 |
| T. denticola + IL1beta + IL2 + C. rectus | 0.88 |
| MMP8 + T. denticola | 0.88 |
| MMP9 + T. denticola | 0.88 |
| Calprotectin + T. forsythia + T. denticola | 0.88 |
| P. gingivalis + ICTP + P. intermedia | 0.88 |
| T. denticola + IL2 + C. rectus | 0.88 |
| T. denticola + IL2 + IL4 + C. rectus | 0.88 |
| MMP8 + P. gingivalis + T. forsythia | 0.88 |
| MMP9 + P. gingivalis + T. forsythia | 0.88 |

TABLE 2-continued

Biomarker combinations resulting in an AUC (probability) value great than at least 80%.

| Signature | AUC |
|---|---|
| T. forsythia + ICTP + P. intermedia | 0.88 |
| MMP8 + OPG + T. forsythia + F. nucleatum | 0.88 |
| MMP8 + T. forsythia + IL4 + C. rectus | 0.88 |
| Calprotectin + OPG + P. gingivalis + T. denticola | 0.88 |
| OPG + T. denticola + IL2 + C. rectus | 0.88 |
| T. forsythia + IL1beta + TNFa + P. intermedia | 0.88 |
| P. gingivalis + P. intermedia + F. nucleatum | 0.88 |
| P. gingivalis + ICTP + IL2 + P. intermedia | 0.88 |
| T. forsythia + IL10 + TNFa + P. intermedia | 0.88 |
| T. denticola + F. nucleatum + C. rectus | 0.88 |
| Calprotectin + P. gingivalis + T. denticola + IL13 | 0.88 |
| Calprotectin + T. forsythia + IL1beta + F. nucleatum | 0.88 |
| OPG + P. gingivalis + ICTP + P. intermedia | 0.88 |
| P. gingivalis + ICTP + IL4 + P. intermedia | 0.88 |
| T. forsythia + T. denticola + IL1beta + IL10 | 0.88 |
| T. forsythia + T. denticola + IL10 + TNFa | 0.88 |
| MMP8 + T. forsythia + IL2 + C. rectus | 0.88 |
| Calprotectin + T. forsythia + IL13 + C. rectus | 0.88 |
| T. forsythia + T. denticola + IL6 + IL4 | 0.88 |
| T. forsythia + IL6 + TNFa + P. intermedia | 0.88 |
| Calprotectin + OPG + P. gingivalis + T. forsythia | 0.88 |
| T. forsythia + T. denticola + IL6 + TNFa | 0.88 |
| T. forsythia + T. denticola + IL13 + TNFa | 0.88 |
| T. denticola + IL13 + IL4 + C. rectus | 0.88 |
| T. denticola + IL13 + C. rectus | 0.88 |
| MMP8 + T. forsythia + ICTP | 0.88 |
| MMP9 + P. gingivalis + ICTP | 0.88 |
| MMP9 + T. forsythia + IL6 + C. rectus | 0.88 |
| OPG + P. gingivalis + T. denticola + IL13 | 0.88 |
| OPG + T. forsythia + TNFa + P. intermedia | 0.88 |
| P. gingivalis + T. forsythia + IL6 + ICTP | 0.88 |
| T. forsythia + T. denticola + IL6 + IL1beta | 0.88 |
| Calprotectin + P. gingivalis + T. denticola + IL6 | 0.88 |
| OPG + P. gingivalis + T. denticola + IL10 | 0.88 |
| T. forsythia + T. denticola + IL1beta + IL2 | 0.88 |
| T. forsythia + T. denticola + F. nucleatum | 0.88 |
| MMP8 + T. forsythia + IL1beta | 0.88 |
| MMP9 + T. forsythia + TNFa + C. rectus | 0.88 |
| Calprotectin + P. gingivalis + ICTP + F. nucleatum | 0.88 |
| MMP9 + T. forsythia + IL10 + C. rectus | 0.88 |
| OPG + T. denticola + IL4 + C. rectus | 0.88 |
| T. forsythia + T. denticola + IL2 + IL4 | 0.88 |
| MMP9 + T. forsythia + C. rectus | 0.88 |
| MMP9 + T. forsythia + ICTP | 0.88 |
| OPG + P. gingivalis + T. denticola + IL6 | 0.88 |
| OPG + T. denticola + TNFa + C. rectus | 0.88 |
| P. gingivalis + T. denticola + IL10 + IL13 | 0.88 |
| T. forsythia + IL2 + TNFa + P. intermedia | 0.88 |
| T. denticola + IL13 + TNFa + C. rectus | 0.88 |
| T. denticola + IL4 + TNFa + C. rectus | 0.88 |
| MMP8 + Calprotectin + T. forsythia | 0.88 |
| T. forsythia + IL1beta + IL10 + P. intermedia | 0.88 |
| T. forsythia + IL4 + TNFa + P. intermedia | 0.88 |
| Calprotectin + OPG + P. gingivalis + C. rectus | 0.88 |
| T. forsythia + T. denticola + IL6 + IL2 | 0.88 |
| T. forsythia + T. denticola + IL1beta + TNFa | 0.88 |
| T. denticola + IL1beta + IL4 + C. rectus | 0.88 |
| T. forsythia + TNFa + P. intermedia | 0.88 |
| Calprotectin + T. denticola + IL6 + F. nucleatum | 0.88 |
| P. gingivalis + T. forsythia + IL6 + IL13 | 0.88 |
| T. denticola + IL4 + C. rectus | 0.88 |
| P. gingivalis + IL6 + IL13 + P. intermedia | 0.88 |
| MMP8 + OPG + T. forsythia | 0.88 |
| MMP9 + OPG + T. forsythia | 0.88 |
| Calprotectin + T. forsythia + TNFa + F. nucleatum | 0.88 |
| MMP9 + T. forsythia + IL4 + F. nucleatum | 0.88 |
| OPG + P. gingivalis + T. denticola + IL4 | 0.88 |
| P. gingivalis + IL6 + TNFa + P. intermedia | 0.88 |
| T. denticola + TNFa + C. rectus | 0.88 |
| MMP9 + T. forsythia + IL1beta | 0.88 |
| MMP9 + T. forsythia + TNFa | 0.88 |
| Calprotectin + T. forsythia + IL1beta + C. rectus | 0.88 |
| MMP9 + P. gingivalis + IL6 + F. nucleatum | 0.88 |
| MMP9 + P. gingivalis + IL10 + F. nucleatum | 0.88 |
| P. gingivalis + T. denticola + IL6 + IL13 | 0.88 |
| T. forsythia + T. denticola + IL1beta + IL4 | 0.88 |
| T. forsythia + IL6 + IL10 + P. intermedia | 0.88 |
| T. forsythia + IL6 + IL13 + C. rectus | 0.88 |
| T. denticola + IL1beta + TNFa + C. rectus | 0.88 |
| T. denticola + C. rectus | 0.88 |
| T. forsythia + T. denticola + TNFa | 0.88 |
| T. denticola + IL1beta + C. rectus | 0.88 |
| MMP8 + P. gingivalis + IL10 + F. nucleatum | 0.88 |
| MMP8 + T. forsythia + IL10 + C. rectus | 0.88 |
| MMP9 + P. gingivalis + IL6 + C. rectus | 0.88 |
| MMP9 + P. gingivalis + TNFa + C. rectus | 0.88 |
| T. forsythia + T. denticola + IL10 + IL4 | 0.88 |
| T. forsythia + IL6 + IL1beta + P. intermedia | 0.88 |
| T. forsythia + T. denticola + IL1beta | 0.88 |
| MMP9 + T. forsythia + IL13 | 0.88 |
| MMP8 + T. forsythia + IL6 + C. rectus | 0.88 |
| Calprotectin + P. gingivalis + T. forsythia + IL6 | 0.88 |
| Calprotectin + T. forsythia + TNFa + C. rectus | 0.88 |
| MMP9 + T. forsythia + IL2 + F. nucleatum | 0.88 |
| OPG + P. gingivalis + T. denticola + IL1beta | 0.88 |
| OPG + P. gingivalis + T. denticola + IL2 | 0.88 |
| T. forsythia + IL6 + ICTP + C. rectus | 0.88 |
| MMP8 + P. gingivalis + IL1beta + F. nucleatum | 0.88 |
| MMP9 + OPG + P. gingivalis + C. rectus | 0.88 |
| OPG + P. gingivalis + IL13 + P. intermedia | 0.88 |
| OPG + T. forsythia + IL1beta + P. intermedia | 0.88 |
| T. forsythia + T. denticola + IL4 + TNFa | 0.88 |
| MMP8 + T. forsythia + IL13 | 0.88 |
| MMP8 + MMP9 + P. gingivalis + C. rectus | 0.88 |
| MMP8 + T. forsythia + IL4 + F. nucleatum | 0.88 |
| Calprotectin + T. forsythia + IL10 + C. rectus | 0.88 |
| Calprotectin + T. denticola + IL2 + F. nucleatum | 0.88 |
| P. gingivalis + T. denticola + IL2 + IL13 | 0.88 |
| P. gingivalis + IL13 + IL4 + P. intermedia | 0.88 |
| OPG + P. gingivalis + T. denticola | 0.88 |
| MMP8 + T. forsythia + IL6 + F. nucleatum | 0.88 |
| MMP9 + T. forsythia + IL6 + F. nucleatum | 0.88 |
| P. gingivalis + T. denticola + IL1beta + IL13 | 0.88 |
| P. gingivalis + IL6 + IL4 + P. intermedia | 0.88 |
| T. forsythia + T. denticola + IL10 + IL2 | 0.88 |
| MMP8 + T. forsythia + C. rectus | 0.88 |
| T. forsythia + T. denticola + IL6 | 0.88 |
| Calprotectin + OPG + P. gingivalis + F. nucleatum | 0.88 |
| Calprotectin + T. forsythia + IL6 + F. nucleatum | 0.88 |
| OPG + T. forsythia + IL2 + P. intermedia | 0.88 |
| P. gingivalis + IL6 + ICTP + F. nucleatum | 0.88 |
| P. gingivalis + IL6 + IL1beta + P. intermedia | 0.88 |
| Calprotectin + T. forsythia + IL4 + F. nucleatum | 0.87 |
| MMP9 + P. gingivalis + IL1beta + F. nucleatum | 0.87 |
| MMP9 + P. gingivalis + IL4 + C. rectus | 0.87 |
| OPG + T. forsythia + IL6 + P. intermedia | 0.87 |
| T. forsythia + T. denticola + IL6 + IL10 | 0.87 |
| T. forsythia + IL10 + IL4 + P. intermedia | 0.87 |
| P. gingivalis + IL13 + P. intermedia | 0.87 |
| MMP8 + T. forsythia + TNFa | 0.87 |
| MMP9 + P. gingivalis + TNFa + F. nucleatum | 0.87 |
| OPG + P. gingivalis + T. forsythia + IL6 | 0.87 |
| OPG + P. gingivalis + T. denticola + TNFa | 0.87 |
| P. gingivalis + IL2 + IL13 + P. intermedia | 0.87 |
| T. forsythia + IL6 + IL13 + F. nucleatum | 0.87 |
| Calprotectin + T. denticola + IL10 + F. nucleatum | 0.87 |
| MMP9 + P. gingivalis + IL13 + C. rectus | 0.87 |
| T. forsythia + IL10 + IL2 + P. intermedia | 0.87 |
| T. forsythia + T. denticola + IL4 | 0.87 |
| T. forsythia + IL10 + P. intermedia | 0.87 |
| MMP8 + OPG + P. gingivalis + C. rectus | 0.87 |
| Calprotectin + T. forsythia + IL2 + C. rectus | 0.87 |
| MMP9 + P. gingivalis + IL10 + C. rectus | 0.87 |
| T. forsythia + ICTP + IL13 + F. nucleatum | 0.87 |
| MMP9 + T. forsythia + F. nucleatum | 0.87 |
| MMP8 + OPG + P. gingivalis + F. nucleatum | 0.87 |
| MMP8 + P. gingivalis + IL6 + F. nucleatum | 0.87 |
| Calprotectin + T. denticola + IL13 + F. nucleatum | 0.87 |
| MMP9 + OPG + T. forsythia + F. nucleatum | 0.87 |
| MMP9 + P. gingivalis + IL2 + C. rectus | 0.87 |

TABLE 2-continued

Biomarker combinations resulting in an AUC (probability) value great than at least 80%.

| Signature | AUC |
|---|---|
| P. gingivalis + T. denticola + IL13 + IL4 | 0.87 |
| Calprotectin + T. forsythia + C. rectus | 0.87 |
| P. gingivalis + IL6 + P. intermedia | 0.87 |
| Calprotectin + P. gingivalis + T. denticola + IL10 | 0.87 |
| Calprotectin + T. forsythia + IL4 + C. rectus | 0.87 |
| OPG + T. forsythia + IL10 + P. intermedia | 0.87 |
| P. gingivalis + IL6 + IL10 + P. intermedia | 0.87 |
| P. gingivalis + IL6 + IL2 + P. intermedia | 0.87 |
| MMP8 + T. forsythia + F. nucleatum | 0.87 |
| T. forsythia + IL1beta + P. intermedia | 0.87 |
| MMP8 + T. forsythia + IL2 + F. nucleatum | 0.87 |
| Calprotectin + T. denticola + TNFa + F. nucleatum | 0.87 |
| MMP9 + T. forsythia + IL10 + F. nucleatum | 0.87 |
| OPG + P. gingivalis + IL6 + P. intermedia | 0.87 |
| OPG + T. forsythia + IL4 + P. intermedia | 0.87 |
| P. gingivalis + T. denticola + IL13 + TNFa | 0.87 |
| T. forsythia + IL1beta + IL2 + P. intermedia | 0.87 |
| T. forsythia + IL1beta + IL4 + P. intermedia | 0.87 |
| MMP8 + MMP9 + T. forsythia + F. nucleatum | 0.87 |
| MMP8 + P. gingivalis + TNFa + C. rectus | 0.87 |
| P. gingivalis + IL6 + ICTP + C. rectus | 0.87 |
| T. forsythia + T. denticola + IL10 | 0.87 |
| T. forsythia + T. denticola + IL2 | 0.87 |
| Calprotectin + P. gingivalis + T. denticola + IL2 | 0.87 |
| Calprotectin + P. gingivalis + IL6 + F. nucleatum | 0.87 |
| P. gingivalis + IL1beta + IL10 + P. intermedia | 0.87 |
| T. forsythia + ICTP + IL13 + C. rectus | 0.87 |
| MMP8 + P. gingivalis + IL4 + C. rectus | 0.87 |
| P. gingivalis + T. forsythia + IL6 + TNFa | 0.87 |
| P. gingivalis + T. forsythia + ICTP + IL13 | 0.87 |
| T. forsythia + IL6 + IL4 + P. intermedia | 0.87 |
| MMP8 + P. gingivalis + IL1beta + C. rectus | 0.87 |
| MMP8 + T. forsythia + IL10 + F. nucleatum | 0.87 |
| MMP9 + P. gingivalis + IL1beta + C. rectus | 0.87 |
| P. gingivalis + IL13 + TNFa + P. intermedia | 0.87 |
| T. forsythia + P. intermedia + C. rectus | 0.87 |
| OPG + T. forsythia + P. intermedia | 0.87 |
| MMP9 + P. gingivalis + IL4 + F. nucleatum | 0.87 |
| T. denticola + IL6 + IL13 + F. nucleatum | 0.87 |
| MMP9 + P. gingivalis + C. rectus | 0.87 |
| OPG + P. gingivalis + TNFa + P. intermedia | 0.87 |
| T. forsythia + ICTP + TNFa + F. nucleatum | 0.87 |
| MMP9 + OPG + P. gingivalis | 0.87 |
| MMP9 + P. gingivalis + IL1beta | 0.87 |
| MMP8 + P. gingivalis + IL10 + C. rectus | 0.87 |
| Calprotectin + T. denticola + IL4 + F. nucleatum | 0.87 |
| OPG + T. denticola + IL13 + F. nucleatum | 0.87 |
| MMP9 + P. gingivalis + IL6 | 0.87 |
| P. gingivalis + IL1beta + TNFa + P. intermedia | 0.87 |
| T. forsythia + IL6 + IL2 + P. intermedia | 0.87 |
| T. denticola + IL10 + IL13 + F. nucleatum | 0.87 |
| T. denticola + IL2 + TNFa + F. nucleatum | 0.87 |
| MMP8 + MMP9 + P. gingivalis + F. nucleatum | 0.87 |
| Calprotectin + P. gingivalis + ICTP + C. rectus | 0.87 |
| OPG + T. denticola + IL6 + F. nucleatum | 0.87 |
| T. forsythia + IL4 + P. intermedia | 0.87 |
| MMP8 + OPG + P. gingivalis | 0.87 |
| MMP8 + P. gingivalis + IL6 | 0.87 |
| MMP8 + P. gingivalis + IL10 | 0.87 |
| MMP8 + P. gingivalis + TNFa + F. nucleatum | 0.87 |
| OPG + P. gingivalis + IL1beta + P. intermedia | 0.87 |
| OPG + P. gingivalis + IL4 + P. intermedia | 0.87 |
| P. gingivalis + T. forsythia + IL10 + IL13 | 0.87 |
| P. gingivalis + IL1beta + IL2 + P. intermedia | 0.87 |
| P. gingivalis + IL1beta + IL4 + P. intermedia | 0.87 |
| T. forsythia + IL6 + ICTP + F. nucleatum | 0.87 |
| MMP9 + P. gingivalis + F. nucleatum | 0.87 |
| OPG + P. gingivalis + P. intermedia | 0.87 |
| MMP8 + P. gingivalis + IL1beta | 0.87 |
| T. forsythia + IL6 + P. intermedia | 0.87 |
| MMP8 + T. forsythia + IL4 | 0.87 |
| MMP9 + T. forsythia + IL4 | 0.87 |
| MMP8 + P. gingivalis + IL13 + C. rectus | 0.87 |
| Calprotectin + T. denticola + IL1beta + F. nucleatum | 0.87 |
| MMP9 + P. gingivalis + IL13 + F. nucleatum | 0.87 |
| P. gingivalis + T. forsythia + IL6 + IL4 | 0.87 |
| P. gingivalis + IL10 + TNFa + P. intermedia | 0.87 |
| Calprotectin + T. denticola + F. nucleatum | 0.87 |
| P. gingivalis + T. denticola + IL13 | 0.87 |
| Calprotectin + OPG + T. denticola | 0.87 |
| P. gingivalis + IL1beta + P. intermedia | 0.87 |
| P. gingivalis + TNFa + P. intermedia | 0.87 |
| Calprotectin + P. gingivalis + T. forsythia + IL10 | 0.87 |
| Calprotectin + P. gingivalis + IL10 + C. rectus | 0.87 |
| P. gingivalis + T. forsythia + ICTP + IL10 | 0.87 |
| P. gingivalis + IL4 + TNFa + P. intermedia | 0.87 |
| P. gingivalis + T. forsythia + C. rectus | 0.87 |
| Calprotectin + P. gingivalis + T. denticola | 0.87 |
| MMP9 + P. gingivalis + TNFa | 0.87 |
| OPG + P. gingivalis + IL10 + P. intermedia | 0.87 |
| OPG + P. gingivalis + IL2 + P. intermedia | 0.87 |
| MMP8 + P. gingivalis + F. nucleatum | 0.87 |
| P. gingivalis + IL2 + P. intermedia | 0.87 |
| MMP8 + P. gingivalis + IL6 + C. rectus | 0.87 |
| MMP8 + P. gingivalis + IL4 + F. nucleatum | 0.87 |
| Calprotectin + P. gingivalis + T. denticola + IL1beta | 0.87 |
| Calprotectin + T. forsythia + IL2 + F. nucleatum | 0.87 |
| OPG + P. gingivalis + T. forsythia + ICTP | 0.87 |
| P. gingivalis + T. denticola + IL6 + IL1beta | 0.87 |
| P. gingivalis + T. denticola + IL6 + IL2 | 0.87 |
| P. gingivalis + IL2 + IL4 + P. intermedia | 0.87 |
| P. gingivalis + IL2 + TNFa + P. intermedia | 0.87 |
| P. gingivalis + P. intermedia + C. rectus | 0.87 |
| MMP8 + P. gingivalis + TNFa | 0.87 |
| MMP8 + P. gingivalis + IL2 + F. nucleatum | 0.87 |
| OPG + T. denticola + IL10 + F. nucleatum | 0.87 |
| P. gingivalis + IL10 + IL2 + P. intermedia | 0.87 |
| T. denticola + IL2 + IL13 + F. nucleatum | 0.87 |
| MMP8 + P. gingivalis + C. rectus | 0.87 |
| Calprotectin + T. forsythia + F. nucleatum | 0.87 |
| P. gingivalis + IL4 + P. intermedia | 0.87 |
| Calprotectin + P. gingivalis + T. denticola + TNFa | 0.87 |
| MMP9 + P. gingivalis + IL2 + F. nucleatum | 0.87 |
| P. gingivalis + T. forsythia + IL6 + IL1beta | 0.87 |
| T. forsythia + T. denticola | 0.87 |
| P. gingivalis + T. denticola + IL10 + IL2 | 0.87 |
| T. forsythia + IL2 + P. intermedia | 0.87 |
| MMP8 + P. gingivalis + IL13 + F. nucleatum | 0.87 |
| OPG + T. denticola + IL2 + F. nucleatum | 0.87 |
| P. gingivalis + T. denticola + IL6 + IL10 | 0.87 |
| P. gingivalis + T. denticola + IL6 + TNFa | 0.87 |
| MMP9 + OPG + P. gingivalis + F. nucleatum | 0.87 |
| T. forsythia + IL2 + IL4 + P. intermedia | 0.87 |
| P. gingivalis + T. forsythia + T. denticola | 0.87 |
| MMP8 + MMP9 + P. gingivalis | 0.87 |
| OPG + T. denticola + TNFa + F. nucleatum | 0.87 |
| P. gingivalis + T. denticola + IL6 + IL4 | 0.87 |
| P. gingivalis + T. denticola + IL2 + TNFa | 0.87 |
| T. forsythia + IL10 + IL13 + F. nucleatum | 0.87 |
| MMP9 + P. gingivalis + IL13 | 0.87 |
| Calprotectin + T. forsythia + IL10 + F. nucleatum | 0.87 |
| P. gingivalis + T. forsythia + IL6 + IL10 | 0.87 |
| P. gingivalis + P. intermedia | 0.87 |
| T. forsythia + P. intermedia | 0.87 |
| P. gingivalis + T. forsythia + IL6 | 0.87 |
| P. gingivalis + T. denticola + IL6 | 0.87 |
| MMP9 + P. gingivalis + IL10 | 0.87 |
| Calprotectin + P. gingivalis + T. denticola + IL4 | 0.87 |
| Calprotectin + P. gingivalis + IL10 + F. nucleatum | 0.87 |
| OPG + T. denticola + IL1beta + F. nucleatum | 0.87 |
| P. gingivalis + IL10 + IL4 + P. intermedia | 0.87 |
| T. forsythia + ICTP + IL10 + C. rectus | 0.87 |
| P. gingivalis + IL10 + P. intermedia | 0.86 |
| MMP8 + P. gingivalis + IL4 | 0.86 |
| MMP9 + P. gingivalis + IL4 | 0.86 |
| P. gingivalis + T. denticola + IL10 + TNFa | 0.86 |
| P. gingivalis + T. forsythia + F. nucleatum | 0.86 |
| MMP9 + T. forsythia + IL2 | 0.86 |
| P. gingivalis + T. forsythia + IL6 + IL2 | 0.86 |
| MMP9 + T. forsythia + IL10 | 0.86 |

TABLE 2-continued

Biomarker combinations resulting in an AUC (probability) value great than at least 80%.

| Signature | AUC |
|---|---|
| P. gingivalis + T. denticola + IL1beta + IL10 | 0.86 |
| P. gingivalis + T. denticola + IL1beta + IL2 | 0.86 |
| T. forsythia + IL6 + TNFa + C. rectus | 0.86 |
| P. gingivalis + T. denticola + IL10 | 0.86 |
| MMP8 + P. gingivalis + IL13 | 0.86 |
| Calprotectin + P. gingivalis + T. forsythia + IL4 | 0.86 |
| OPG + T. forsythia + IL13 + F. nucleatum | 0.86 |
| P. gingivalis + T. denticola + F. nucleatum | 0.86 |
| MMP8 + MMP9 + T. forsythia | 0.86 |
| Calprotectin + T. denticola + IL6 | 0.86 |
| MMP9 + T. forsythia + IL6 | 0.86 |
| MMP8 + P. gingivalis + IL2 + C. rectus | 0.86 |
| Calprotectin + P. gingivalis + T. forsythia + TNFa | 0.86 |
| OPG + P. gingivalis + T. forsythia + IL10 | 0.86 |
| T. forsythia + IL6 + TNFa + F. nucleatum | 0.86 |
| T. denticola + IL6 + IL10 + F. nucleatum | 0.86 |
| P. gingivalis + T. denticola + IL2 | 0.86 |
| Calprotectin + P. gingivalis + T. forsythia + IL2 | 0.86 |
| OPG + T. forsythia + ICTP + F. nucleatum | 0.86 |
| OPG + T. forsythia + ICTP + C. rectus | 0.86 |
| P. gingivalis + T. denticola + IL10 + IL4 | 0.86 |
| T. denticola + IL6 + IL1beta + F. nucleatum | 0.86 |
| MMP8 + T. forsythia + IL6 | 0.86 |
| Calprotectin + OPG + T. forsythia | 0.86 |
| Calprotectin + P. gingivalis + IL4 + C. rectus | 0.86 |
| P. gingivalis + T. forsythia + ICTP + IL2 | 0.86 |
| P. gingivalis + T. denticola + IL2 + IL4 | 0.86 |
| T. forsythia + ICTP + IL2 + F. nucleatum | 0.86 |
| P. gingivalis + T. forsythia + ICTP + IL4 | 0.86 |
| P. gingivalis + T. forsythia + IL1beta + IL13 | 0.86 |
| Calprotectin + T. forsythia + ICTP | 0.86 |
| Calprotectin + T. forsythia + IL13 | 0.86 |
| Calprotectin + P. gingivalis + IL2 + C. rectus | 0.86 |
| P. gingivalis + T. forsythia + ICTP + TNFa | 0.86 |
| T. denticola + IL13 + IL4 + F. nucleatum | 0.86 |
| MMP8 + T. forsythia + IL2 | 0.86 |
| T. denticola + IL6 + TNFa + F. nucleatum | 0.86 |
| Calprotectin + P. gingivalis + T. forsythia | 0.86 |
| OPG + T. denticola + F. nucleatum | 0.86 |
| MMP8 + T. forsythia + IL10 | 0.86 |
| T. denticola + IL6 + IL13 | 0.86 |
| OPG + T. denticola + IL4 + F. nucleatum | 0.86 |
| MMP8 + P. gingivalis + IL2 | 0.86 |
| Calprotectin + T. denticola + IL13 | 0.86 |
| OPG + T. denticola + IL6 | 0.86 |
| Calprotectin + P. gingivalis + T. forsythia + IL1beta | 0.86 |
| T. forsythia + IL6 + IL1beta + F. nucleatum | 0.86 |
| T. forsythia + ICTP + IL4 + F. nucleatum | 0.86 |
| T. forsythia + IL2 + IL13 + F. nucleatum | 0.86 |
| T. denticola + IL1beta + IL10 + F. nucleatum | 0.86 |
| Calprotectin + P. gingivalis + TNFa + C. rectus | 0.86 |
| OPG + T. forsythia + TNFa + F. nucleatum | 0.86 |
| T. forsythia + ICTP + IL1beta + F. nucleatum | 0.86 |
| T. denticola + IL10 + TNFa + F. nucleatum | 0.86 |
| P. gingivalis + T. forsythia + ICTP | 0.86 |
| Calprotectin + P. gingivalis + IL1beta + C. rectus | 0.86 |
| OPG + P. gingivalis + T. forsythia + IL13 | 0.86 |
| T. forsythia + ICTP + IL10 + F. nucleatum | 0.86 |
| T. forsythia + ICTP + TNFa + C. rectus | 0.86 |
| T. denticola + IL6 + IL2 + F. nucleatum | 0.86 |
| T. forsythia + ICTP + F. nucleatum | 0.86 |
| T. forsythia + IL1beta + IL13 + F. nucleatum | 0.86 |
| MMP8 + P. gingivalis | 0.86 |
| MMP9 + P. gingivalis | 0.86 |
| P. gingivalis + T. denticola + IL4 | 0.86 |
| T. denticola + IL6 + F. nucleatum | 0.86 |
| Calprotectin + T. forsythia + IL6 | 0.86 |
| OPG + T. forsythia + IL6 + F. nucleatum | 0.86 |
| T. forsythia + IL10 + IL13 + C. rectus | 0.86 |
| MMP8 + T. forsythia | 0.86 |
| MMP9 + T. forsythia | 0.86 |
| T. forsythia + IL6 + IL13 | 0.86 |
| T. forsythia + ICTP + IL4 + C. rectus | 0.86 |
| Calprotectin + T. denticola + IL10 | 0.86 |
| P. gingivalis + T. forsythia + IL2 + IL13 | 0.86 |
| P. gingivalis + T. forsythia + IL13 + TNFa | 0.86 |
| T. forsythia + IL6 + IL4 + C. rectus | 0.86 |
| T. forsythia + ICTP + IL1beta + C. rectus | 0.86 |
| Calprotectin + P. gingivalis + IL6 | 0.86 |
| P. gingivalis + T. forsythia + ICTP + IL1beta | 0.86 |
| T. denticola + IL1beta + IL2 + F. nucleatum | 0.86 |
| T. denticola + IL1beta + IL13 + F. nucleatum | 0.86 |
| P. gingivalis + T. denticola + IL4 + TNFa | 0.86 |
| T. forsythia + IL13 + IL4 + F. nucleatum | 0.86 |
| T. denticola + IL6 + IL4 + F. nucleatum | 0.86 |
| T. forsythia + IL6 + IL1beta + C. rectus | 0.86 |
| T. forsythia + IL6 + IL10 + C. rectus | 0.86 |
| Calprotectin + T. denticola + IL2 | 0.86 |
| OPG + P. gingivalis + T. forsythia + IL2 | 0.86 |
| T. forsythia + IL6 + IL2 + C. rectus | 0.86 |
| MMP9 + P. gingivalis + IL2 | 0.86 |
| P. gingivalis + T. denticola + IL1beta + IL4 | 0.86 |
| T. forsythia + ICTP + IL2 + C. rectus | 0.86 |
| Calprotectin + P. gingivalis + IL13 + F. nucleatum | 0.86 |
| T. forsythia + ICTP + C. rectus | 0.86 |
| T. forsythia + ICTP + IL13 | 0.86 |
| P. gingivalis + IL6 + TNFa + F. nucleatum | 0.86 |
| T. forsythia + IL6 + IL4 + F. nucleatum | 0.86 |
| T. denticola + IL2 + IL4 + F. nucleatum | 0.86 |
| T. denticola + IL2 + F. nucleatum | 0.86 |
| T. denticola + IL10 + IL13 | 0.86 |
| OPG + P. gingivalis + T. forsythia + IL4 | 0.86 |
| OPG + T. forsythia + IL6 + C. rectus | 0.86 |
| P. gingivalis + IL6 + IL13 + F. nucleatum | 0.86 |
| Calprotectin + P. gingivalis + C. rectus | 0.86 |
| Calprotectin + P. gingivalis + ICTP | 0.86 |
| P. gingivalis + T. denticola | 0.86 |
| P. gingivalis + T. denticola + TNFa | 0.86 |
| Calprotectin + P. gingivalis + TNFa + F. nucleatum | 0.86 |
| P. gingivalis + IL10 + IL13 + F. nucleatum | 0.86 |
| OPG + P. gingivalis + T. forsythia | 0.86 |
| P. gingivalis + T. forsythia + IL13 | 0.86 |
| T. denticola + IL13 + F. nucleatum | 0.86 |
| P. gingivalis + IL6 + ICTP | 0.86 |
| OPG + P. gingivalis + T. forsythia + TNFa | 0.86 |
| P. gingivalis + T. forsythia + IL13 + IL4 | 0.86 |
| P. gingivalis + ICTP + IL10 + F. nucleatum | 0.86 |
| T. denticola + IL10 + F. nucleatum | 0.86 |
| OPG + T. denticola + IL13 | 0.86 |
| Calprotectin + P. gingivalis + IL2 + F. nucleatum | 0.86 |
| Calprotectin + P. gingivalis + IL4 + F. nucleatum | 0.86 |
| T. forsythia + IL13 + TNFa + F. nucleatum | 0.86 |
| T. denticola + IL13 + TNFa + F. nucleatum | 0.86 |
| Calprotectin + P. gingivalis + F. nucleatum | 0.86 |
| Calprotectin + T. denticola + IL4 | 0.86 |
| OPG + T. denticola + IL10 | 0.86 |
| Calprotectin + P. gingivalis + IL13 + C. rectus | 0.86 |
| T. denticola + IL10 + IL4 + F. nucleatum | 0.86 |
| P. gingivalis + T. forsythia + IL10 | 0.85 |
| P. gingivalis + T. denticola + IL1beta | 0.85 |
| P. gingivalis + T. denticola + IL1beta + TNFa | 0.85 |
| OPG + T. forsythia + IL4 + C. rectus | 0.85 |
| OPG + T. forsythia + IL1beta + C. rectus | 0.85 |
| OPG + T. forsythia + IL13 + C. rectus | 0.85 |
| P. gingivalis + T. forsythia + IL10 + IL2 | 0.85 |
| T. forsythia + IL10 + TNFa + F. nucleatum | 0.85 |
| Calprotectin + T. denticola + TNFa | 0.85 |
| T. forsythia + F. nucleatum + C. rectus | 0.85 |
| Calprotectin + P. gingivalis + IL1beta + F. nucleatum | 0.85 |
| OPG + T. forsythia + IL4 + F. nucleatum | 0.85 |
| P. gingivalis + ICTP + IL1beta + F. nucleatum | 0.85 |
| T. forsythia + IL1beta + TNFa + F. nucleatum | 0.85 |
| T. denticola + IL6 + IL2 | 0.85 |
| OPG + P. gingivalis + IL6 + F. nucleatum | 0.85 |
| OPG + T. forsythia + IL1beta + F. nucleatum | 0.85 |
| T. forsythia + IL4 + TNFa + F. nucleatum | 0.85 |
| T. forsythia + IL6 + ICTP | 0.85 |
| OPG + P. gingivalis + T. forsythia + IL1beta | 0.85 |
| T. denticola + IL1beta + IL4 + F. nucleatum | 0.85 |
| T. forsythia + IL6 + C. rectus | 0.85 |

TABLE 2-continued

Biomarker combinations resulting in an AUC (probability) value great than at least 80%.

| Signature | AUC |
|---|---|
| *T. forsythia* + IL13 + *F. nucleatum* | 0.85 |
| OPG + *T. forsythia* + TNFa + *C. rectus* | 0.85 |
| *P. gingivalis* + IL6 + IL1beta + *F. nucleatum* | 0.85 |
| *P. gingivalis* + IL6 + IL13 + *C. rectus* | 0.85 |
| *T. forsythia* + IL6 + IL10 + *F. nucleatum* | 0.85 |
| *T. forsythia* + IL6 + IL2 + *F. nucleatum* | 0.85 |
| Calprotectin + *T. denticola* | 0.85 |
| Calprotectin + OPG + *P. gingivalis* | 0.85 |
| *T. forsythia* + IL13 + TNFa + *C. rectus* | 0.85 |
| *T. denticola* + IL6 + TNFa | 0.85 |
| OPG + *T. forsythia* + IL2 + *F. nucleatum* | 0.85 |
| OPG + *T. forsythia* + IL2 + *C. rectus* | 0.85 |
| *P. gingivalis* + IL6 + IL10 + *F. nucleatum* | 0.85 |
| *T. forsythia* + IL13 + IL4 + *C. rectus* | 0.85 |
| Calprotectin + *T. denticola* + IL1beta | 0.85 |
| OPG + *T. denticola* + TNFa | 0.85 |
| OPG + *P. gingivalis* + ICTP + *F. nucleatum* | 0.85 |
| Calprotectin + *T. forsythia* + TNFa | 0.85 |
| *T. forsythia* + IL2 + IL13 + *C. rectus* | 0.85 |
| *T. forsythia* + IL2 + TNFa + *F. nucleatum* | 0.85 |
| *T. denticola* + IL10 + IL2 + *F. nucleatum* | 0.85 |
| *T. forsythia* + IL13 + *C. rectus* | 0.85 |
| *T. denticola* + IL6 + IL1beta | 0.85 |
| *T. denticola* + IL4 + TNFa + *F. nucleatum* | 0.85 |
| *T. forsythia* + IL6 + *F. nucleatum* | 0.85 |
| *T. denticola* + IL6 + IL4 | 0.85 |
| *P. gingivalis* + *T. forsythia* + IL10 + IL4 | 0.85 |
| *T. denticola* + IL4 + *F. nucleatum* | 0.85 |
| OPG + *T. forsythia* + IL10 + *F. nucleatum* | 0.85 |
| *P. gingivalis* + IL6 + IL4 + *F. nucleatum* | 0.85 |
| *T. forsythia* + IL1beta + IL13 + *C. rectus* | 0.85 |
| OPG + *T. forsythia* + *F. nucleatum* | 0.85 |
| *T. forsythia* + TNFa + *F. nucleatum* | 0.85 |
| Calprotectin + *T. forsythia* + IL1beta | 0.85 |
| *P. gingivalis* + IL6 + IL2 + *F. nucleatum* | 0.85 |
| *P. gingivalis* + ICTP + IL4 + *F. nucleatum* | 0.85 |
| OPG + *T. denticola* + IL2 | 0.85 |
| *P. gingivalis* + ICTP + IL2 + *F. nucleatum* | 0.85 |
| *P. gingivalis* + IL6 + *F. nucleatum* | 0.85 |
| *T. denticola* + IL1beta + *F. nucleatum* | 0.85 |
| OPG + *T. forsythia* + IL10 + *C. rectus* | 0.85 |
| OPG + *T. forsythia* + *C. rectus* | 0.85 |
| *P. gingivalis* + *T. forsythia* + IL2 + IL4 | 0.85 |
| *T. forsythia* + IL1beta + IL10 + *F. nucleatum* | 0.85 |
| *T. forsythia* + IL1beta + IL2 + *F. nucleatum* | 0.85 |
| *T. denticola* + TNFa + *F. nucleatum* | 0.85 |
| OPG + *T. denticola* + IL1beta | 0.85 |
| OPG + *P. gingivalis* + IL6 + *C. rectus* | 0.85 |
| *T. forsythia* + ICTP + TNFa | 0.85 |
| *T. denticola* + IL2 + IL13 | 0.85 |
| *P. gingivalis* + *T. forsythia* + IL1beta + IL10 | 0.85 |
| *T. forsythia* + IL1beta + IL4 + *F. nucleatum* | 0.85 |
| *T. denticola* + *F. nucleatum* | 0.85 |
| *T. denticola* + IL6 + IL10 | 0.85 |
| *T. denticola* + IL1beta + IL13 | 0.85 |
| *T. forsythia* + IL2 + IL4 + *F. nucleatum* | 0.85 |
| *T. forsythia* + IL6 | 0.85 |
| *T. forsythia* + IL1beta + *F. nucleatum* | 0.85 |
| Calprotectin + *P. gingivalis* + IL10 | 0.85 |
| OPG + *T. forsythia* + ICTP | 0.85 |
| *P. gingivalis* + *T. forsythia* + IL10 + TNFa | 0.85 |
| OPG + *T. denticola* | 0.85 |
| Calprotectin + *T. forsythia* + IL4 | 0.85 |
| OPG + *T. denticola* + IL4 | 0.85 |
| *T. forsythia* + IL10 + IL13 | 0.85 |
| *T. forsythia* + IL2 + IL4 + *C. rectus* | 0.85 |
| *T. denticola* + IL1beta + TNFa + *F. nucleatum* | 0.85 |
| *P. gingivalis* + *T. forsythia* + IL2 | 0.85 |
| *T. forsythia* + IL1beta + IL4 + *C. rectus* | 0.85 |
| *T. forsythia* + IL2 + TNFa + *C. rectus* | 0.85 |
| *T. denticola* + IL13 + IL4 | 0.85 |
| Calprotectin + *T. forsythia* + IL10 | 0.85 |
| *T. forsythia* + IL1beta + IL10 + *C. rectus* | 0.85 |
| *T. forsythia* + IL1beta + IL2 + *C. rectus* | 0.85 |
| *T. forsythia* + IL1beta + TNFa + *C. rectus* | 0.85 |
| *T. forsythia* + IL10 + IL4 + *F. nucleatum* | 0.85 |
| Calprotectin + *P. gingivalis* + IL2 | 0.84 |
| *P. gingivalis* + IL6 + IL13 | 0.84 |
| *P. gingivalis* + *T. forsythia* + IL2 + TNFa | 0.84 |
| *P. gingivalis* + IL6 + TNFa + *C. rectus* | 0.84 |
| *T. forsythia* + IL1beta + *C. rectus* | 0.84 |
| *P. gingivalis* + IL6 + IL4 + *C. rectus* | 0.84 |
| Calprotectin + *T. forsythia* | 0.84 |
| *P. gingivalis* + ICTP + *F. nucleatum* | 0.84 |
| *T. denticola* + IL10 + IL2 | 0.84 |
| *P. gingivalis* + ICTP + TNFa + *F. nucleatum* | 0.84 |
| *T. forsythia* + IL4 + *F. nucleatum* | 0.84 |
| MMP8 + Calprotectin + *P. intermedia* + *C. rectus* | 0.84 |
| *P. gingivalis* + IL6 + IL2 + *C. rectus* | 0.84 |
| *T. forsythia* + TNFa + *C. rectus* | 0.84 |
| OPG + *T. forsythia* + IL13 | 0.84 |
| *P. gingivalis* + IL6 + IL1beta + *C. rectus* | 0.84 |
| *P. gingivalis* + *T. forsythia* + IL4 | 0.84 |
| *P. gingivalis* + IL6 + *C. rectus* | 0.84 |
| *T. forsythia* + ICTP + IL1beta | 0.84 |
| *T. denticola* + IL2 + TNFa | 0.84 |
| OPG + *P. gingivalis* + IL10 + *F. nucleatum* | 0.84 |
| *P. gingivalis* + ICTP + IL13 + *F. nucleatum* | 0.84 |
| *T. forsythia* + IL10 + IL4 + *C. rectus* | 0.84 |
| *T. forsythia* + IL10 + TNFa + *C. rectus* | 0.84 |
| *T. forsythia* + IL4 + TNFa + *C. rectus* | 0.84 |
| *T. forsythia* + IL4 + *C. rectus* | 0.84 |
| Calprotectin + *T. forsythia* + IL2 | 0.84 |
| Calprotectin + *P. gingivalis* + IL13 | 0.84 |
| *T. denticola* + IL10 + TNFa | 0.84 |
| *T. denticola* + IL13 + TNFa | 0.84 |
| *P. gingivalis* + ICTP + IL10 + *C. rectus* | 0.84 |
| *T. forsythia* + IL2 + *F. nucleatum* | 0.84 |
| Calprotectin + *P. gingivalis* + IL1beta | 0.84 |
| *P. gingivalis* + ICTP + IL1beta + *C. rectus* | 0.84 |
| *P. gingivalis* + ICTP + IL4 + *C. rectus* | 0.84 |
| Calprotectin + *P. gingivalis* + IL4 | 0.84 |
| *T. forsythia* + IL13 + TNFa | 0.84 |
| *P. gingivalis* + *T. forsythia* + IL1beta + IL4 | 0.84 |
| *P. gingivalis* + ICTP + IL2 + *C. rectus* | 0.84 |
| *T. denticola* + IL13 | 0.84 |
| *T. forsythia* + ICTP + IL4 | 0.84 |
| *P. gingivalis* + ICTP + IL10 | 0.84 |
| *T. forsythia* + IL13 + IL4 | 0.84 |
| *P. gingivalis* + *T. forsythia* + IL4 + TNFa | 0.84 |
| *P. gingivalis* + ICTP + TNFa + *C. rectus* | 0.84 |
| *T. forsythia* + IL10 + IL2 + *F. nucleatum* | 0.84 |
| *P. gingivalis* + *T. forsythia* + TNFa | 0.84 |
| *T. forsythia* + IL2 + IL13 | 0.84 |
| Calprotectin + MMP9 + *P. intermedia* + *C. rectus* | 0.84 |
| *P. gingivalis* + IL6 + IL10 + *C. rectus* | 0.84 |
| *T. forsythia* + IL10 + *F. nucleatum* | 0.84 |
| OPG + *P. gingivalis* + IL6 | 0.84 |
| *T. forsythia* + ICTP + IL10 | 0.84 |
| *P. gingivalis* + *T. forsythia* | 0.84 |
| *T. denticola* + IL1beta + IL10 | 0.84 |
| OPG + *P. gingivalis* + ICTP + *C. rectus* | 0.84 |
| *P. gingivalis* + *T. forsythia* + IL1beta + TNFa | 0.84 |
| *T. forsythia* + *F. nucleatum* | 0.84 |
| *T. forsythia* + IL10 + *C. rectus* | 0.84 |
| *T. denticola* + IL10 + IL4 | 0.84 |
| Calprotectin + *P. gingivalis* + TNFa | 0.84 |
| Calprotectin + MMP9 + *P. intermedia* + *F. nucleatum* | 0.84 |
| *P. gingivalis* + *T. forsythia* + IL1beta + IL2 | 0.84 |
| *T. denticola* + IL10 | 0.84 |
| *T. forsythia* + IL6 + TNFa | 0.84 |
| MMP8 + Calprotectin + *P. intermedia* + *F. nucleatum* | 0.84 |
| *T. forsythia* + ICTP + IL2 | 0.84 |
| *T. forsythia* + IL10 + IL2 + *C. rectus* | 0.84 |
| *P. gingivalis* + ICTP + *C. rectus* | 0.84 |
| *T. forsythia* + IL2 + *C. rectus* | 0.84 |
| *T. forsythia* + IL1beta + IL13 | 0.84 |
| *T. denticola* + IL2 + IL4 | 0.84 |
| *P. gingivalis* + ICTP + IL13 + *C. rectus* | 0.84 |
| *P. gingivalis* + IL10 + TNFa + *F. nucleatum* | 0.84 |

TABLE 2-continued

Biomarker combinations resulting in an AUC (probability) value great than at least 80%.

| Signature | AUC |
|---|---|
| P. gingivalis + T. forsythia + IL1beta | 0.84 |
| T. denticola + IL1beta + IL2 | 0.84 |
| T. forsythia + C. rectus | 0.84 |
| T. forsythia + ICTP | 0.84 |
| MMP8 + ICTP + P. intermedia + F. nucleatum | 0.84 |
| MMP8 + ICTP + P. intermedia + C. rectus | 0.84 |
| OPG + P. gingivalis + IL4 + F. nucleatum | 0.84 |
| P. gingivalis + IL10 + IL2 + F. nucleatum | 0.84 |
| T. forsythia + IL13 | 0.84 |
| P. gingivalis + IL10 + F. nucleatum | 0.84 |
| Calprotectin + P. gingivalis | 0.84 |
| T. denticola + IL2 | 0.84 |
| OPG + T. forsythia + IL6 | 0.84 |
| P. gingivalis + ICTP + IL1beta | 0.84 |
| P. gingivalis + IL1beta + IL10 + F. nucleatum | 0.84 |
| P. gingivalis + IL10 + IL4 + F. nucleatum | 0.84 |
| P. gingivalis + IL6 + TNFa | 0.84 |
| T. forsythia + IL6 + IL1beta | 0.83 |
| P. gingivalis + IL6 + IL2 | 0.83 |
| P. gingivalis + ICTP + IL4 | 0.83 |
| OPG + P. gingivalis + IL1beta + F. nucleatum | 0.83 |
| P. gingivalis + ICTP + IL2 | 0.83 |
| MMP8 + TNFa + P. intermedia + F. nucleatum | 0.83 |
| OPG + P. gingivalis + IL2 + F. nucleatum | 0.83 |
| P. gingivalis + IL13 + IL4 + F. nucleatum | 0.83 |
| MMP8 + Calprotectin + P. intermedia | 0.83 |
| OPG + P. gingivalis + TNFa + F. nucleatum | 0.83 |
| T. forsythia + IL6 + IL10 | 0.83 |
| OPG + P. gingivalis + ICTP | 0.83 |
| P. gingivalis + IL6 + IL10 | 0.83 |
| T. forsythia + IL6 + IL4 | 0.83 |
| P. gingivalis + IL6 + IL1beta | 0.83 |
| T. denticola + IL4 + TNFa | 0.83 |
| OPG + P. gingivalis + F. nucleatum | 0.83 |
| P. gingivalis + IL6 | 0.83 |
| OPG + T. forsythia + TNFa | 0.83 |
| P. gingivalis + IL1beta + IL4 + F. nucleatum | 0.83 |
| P. gingivalis + IL2 + IL13 + F. nucleatum | 0.83 |
| P. gingivalis + IL2 + IL4 + F. nucleatum | 0.83 |
| OPG + P. gingivalis + IL13 + F. nucleatum | 0.83 |
| Calprotectin + MMP9 + P. intermedia | 0.83 |
| P. gingivalis + IL2 + TNFa + F. nucleatum | 0.83 |
| P. gingivalis + IL1beta + IL2 + F. nucleatum | 0.83 |
| P. gingivalis + IL4 + F. nucleatum | 0.83 |
| P. gingivalis + IL6 + IL4 | 0.83 |
| P. gingivalis + IL2 + F. nucleatum | 0.83 |
| MMP8 + ICTP + P. intermedia | 0.83 |
| P. gingivalis + ICTP + IL13 | 0.83 |
| P. gingivalis + IL4 + TNFa + F. nucleatum | 0.83 |
| P. gingivalis + ICTP + TNFa | 0.83 |
| P. gingivalis + IL13 + TNFa + F. nucleatum | 0.83 |
| P. gingivalis + IL1beta + F. nucleatum | 0.83 |
| P. gingivalis + IL1beta + IL13 + F. nucleatum | 0.83 |
| P. gingivalis + IL1beta + TNFa + F. nucleatum | 0.83 |
| T. forsythia + IL6 + IL2 | 0.83 |
| T. denticola + IL1beta + IL4 | 0.83 |
| P. gingivalis + F. nucleatum + C. rectus | 0.83 |
| P. gingivalis + ICTP | 0.83 |
| MMP8 + TNFa + P. intermedia | 0.83 |
| OPG + T. forsythia + IL1beta | 0.83 |
| OPG + T. forsythia + IL4 | 0.83 |
| MMP8 + IL1beta + P. intermedia + F. nucleatum | 0.83 |
| P. gingivalis + TNFa + F. nucleatum | 0.83 |
| T. denticola + IL4 | 0.83 |
| T. denticola + IL1beta + TNFa | 0.83 |
| T. denticola + TNFa | 0.83 |
| MMP8 + TNFa + P. intermedia + C. rectus | 0.83 |
| P. gingivalis + IL10 + IL13 + C. rectus | 0.83 |
| MMP9 + TNFa + P. intermedia + C. rectus | 0.83 |
| P. gingivalis + IL1beta + IL10 + C. rectus | 0.83 |
| P. gingivalis + IL13 + F. nucleatum | 0.83 |
| OPG + P. gingivalis + IL10 + C. rectus | 0.83 |
| MMP8 + IL1beta + P. intermedia + C. rectus | 0.82 |
| T. forsythia + IL6 | 0.82 |
| P. gingivalis + IL1beta + IL2 + C. rectus | 0.82 |
| OPG + T. forsythia + IL10 | 0.82 |
| P. gingivalis + F. nucleatum | 0.82 |
| T. denticola + IL1beta | 0.82 |
| OPG + T. forsythia + IL2 | 0.82 |
| P. gingivalis + IL10 + IL2 + C. rectus | 0.82 |
| P. gingivalis + IL2 + IL13 + C. rectus | 0.82 |
| T. denticola | 0.82 |
| MMP9 + TNFa + P. intermedia | 0.82 |
| T. forsythia + IL2 + TNFa | 0.82 |
| Calprotectin + TNFa + P. intermedia + F. nucleatum | 0.82 |
| MMP9 + TNFa + P. intermedia + F. nucleatum | 0.82 |
| OPG + P. gingivalis + IL13 + C. rectus | 0.82 |
| OPG + T. forsythia | 0.82 |
| MMP8 + IL10 + P. intermedia + F. nucleatum | 0.82 |
| MMP8 + IL6 + P. intermedia + F. nucleatum | 0.82 |
| OPG + P. gingivalis + IL1beta + C. rectus | 0.82 |
| P. gingivalis + IL13 + IL4 + C. rectus | 0.82 |
| Calprotectin + ICTP + P. intermedia + F. nucleatum | 0.82 |
| OPG + P. gingivalis + C. rectus | 0.82 |
| T. forsythia + IL4 + TNFa | 0.82 |
| MMP9 + IL1beta + P. intermedia + C. rectus | 0.82 |
| T. forsythia + IL1beta + TNFa | 0.82 |
| MMP9 + ICTP + P. intermedia + C. rectus | 0.82 |
| OPG + P. gingivalis + IL2 + C. rectus | 0.82 |
| OPG + P. gingivalis + TNFa + C. rectus | 0.82 |
| MMP8 + OPG + P. intermedia + F. nucleatum | 0.82 |
| OPG + P. gingivalis + IL4 + C. rectus | 0.82 |
| MMP8 + P. intermedia + F. nucleatum | 0.82 |
| MMP8 + IL13 + P. intermedia + C. rectus | 0.82 |
| P. gingivalis + IL10 + IL13 | 0.82 |
| MMP8 + IL13 + P. intermedia + F. nucleatum | 0.82 |
| MMP9 + ICTP + P. intermedia + F. nucleatum | 0.82 |
| P. gingivalis + IL2 + IL4 + C. rectus | 0.82 |
| P. gingivalis + IL10 + TNFa + C. rectus | 0.82 |
| Calprotectin + ICTP + P. intermedia + C. rectus | 0.82 |
| T. forsythia + TNFa | 0.82 |
| MMP8 + IL1beta + P. intermedia | 0.82 |
| OPG + P. gingivalis + IL10 | 0.82 |
| MMP8 + IL2 + P. intermedia + F. nucleatum | 0.82 |
| P. gingivalis + IL10 + IL4 + C. rectus | 0.82 |
| MMP8 + MMP9 + P. intermedia + C. rectus | 0.82 |
| MMP8 + IL4 + P. intermedia + F. nucleatum | 0.82 |
| P. gingivalis + IL10 + C. rectus | 0.82 |
| T. forsythia + IL10 + TNFa | 0.82 |
| MMP9 + IL1beta + P. intermedia + F. nucleatum | 0.82 |
| P. gingivalis + IL13 + TNFa + C. rectus | 0.82 |
| P. gingivalis + IL2 + C. rectus | 0.82 |
| MMP8 + MMP9 + P. intermedia + F. nucleatum | 0.82 |
| MMP8 + OPG + P. intermedia + C. rectus | 0.82 |
| MMP8 + IL10 + P. intermedia + C. rectus | 0.82 |
| MMP9 + IL2 + P. intermedia + C. rectus | 0.82 |
| P. gingivalis + IL2 + TNFa + C. rectus | 0.82 |
| Calprotectin + MMP9 + F. nucleatum + C. rectus | 0.81 |
| MMP8 + IL6 + P. intermedia | 0.81 |
| OPG + P. gingivalis + IL1beta | 0.81 |
| MMP8 + IL2 + P. intermedia + C. rectus | 0.81 |
| MMP8 + OPG + P. intermedia | 0.81 |
| OPG + P. gingivalis + IL4 | 0.81 |
| MMP8 + IL6 + P. intermedia + C. rectus | 0.81 |
| P. gingivalis + IL1beta + IL4 + C. rectus | 0.81 |
| MMP8 + P. intermedia + C. rectus | 0.81 |
| P. gingivalis + IL4 + C. rectus | 0.81 |
| P. gingivalis + IL10 + IL2 | 0.81 |
| MMP9 + IL4 + P. intermedia + F. nucleatum | 0.81 |
| P. gingivalis + IL1beta + TNFa + C. rectus | 0.81 |
| P. gingivalis + IL4 + TNFa + C. rectus | 0.81 |
| T. forsythia + IL1beta + IL4 | 0.81 |
| P. gingivalis + TNFa + C. rectus | 0.81 |
| OPG + P. gingivalis + IL2 | 0.81 |
| T. forsythia + IL2 + IL4 | 0.81 |
| MMP8 + IL4 + P. intermedia + C. rectus | 0.81 |
| Calprotectin + IL2 + P. intermedia + F. nucleatum | 0.81 |
| T. forsythia + IL1beta | 0.81 |
| P. gingivalis + IL1beta + C. rectus | 0.81 |
| T. forsythia + IL1beta + IL10 | 0.81 |

TABLE 2-continued

Biomarker combinations resulting in an AUC (probability) value great than at least 80%.

| Signature | AUC |
|---|---|
| MMP9 + ICTP + P. intermedia | 0.81 |
| P. gingivalis + IL1beta + IL10 | 0.81 |
| P. gingivalis + IL2 + IL13 | 0.81 |
| Calprotectin + IL10 + P. intermedia + F. nucleatum | 0.81 |
| P. gingivalis + IL13 + C. rectus | 0.81 |
| Calprotectin + OPG + P. intermedia + F. nucleatum | 0.81 |
| T. forsythia + IL1beta + IL2 | 0.81 |
| Calprotectin + TNFa + P. intermedia + C. rectus | 0.81 |
| Calprotectin + IL13 + P. intermedia + F. nucleatum | 0.81 |
| OPG + P. gingivalis + TNFa | 0.81 |
| MMP9 + IL2 + P. intermedia + F. nucleatum | 0.81 |
| P. gingivalis + IL1beta + IL13 + C. rectus | 0.81 |
| MMP8 + MMP9 + P. intermedia | 0.81 |
| P. gingivalis + IL1beta + IL2 | 0.81 |
| Calprotectin + IL6 + P. intermedia + F. nucleatum | 0.81 |
| MMP9 + IL6 + P. intermedia + F. nucleatum | 0.81 |
| Calprotectin + P. intermedia + F. nucleatum | 0.81 |
| P. gingivalis + IL10 + IL4 | 0.81 |
| T. forsythia + IL10 + IL4 | 0.81 |
| Calprotectin + IL1beta + P. intermedia + F. nucleatum | 0.81 |
| Calprotectin + IL4 + P. intermedia + F. nucleatum | 0.81 |
| MMP9 + IL6 + P. intermedia + C. rectus | 0.81 |
| MMP9 + P. intermedia + F. nucleatum | 0.81 |
| Calprotectin + OPG + P. intermedia + C. rectus | 0.81 |
| OPG + P. gingivalis + IL13 | 0.81 |
| MMP9 + IL13 + P. intermedia + C. rectus | 0.81 |
| P. gingivalis + C. rectus | 0.81 |
| MMP8 + IL13 + P. intermedia | 0.81 |
| P. gingivalis + IL10 + TNFa | 0.81 |
| P. gingivalis + IL13 + TNFa | 0.81 |
| P. gingivalis + IL13 + IL4 | 0.81 |
| MMP9 + OPG + P. intermedia + C. rectus | 0.81 |
| T. forsythia + IL4 | 0.81 |
| P. gingivalis + IL10 | 0.81 |
| MMP8 + IL4 + P. intermedia | 0.81 |
| MMP9 + IL10 + P. intermedia + C. rectus | 0.81 |
| Calprotectin + IL10 + P. intermedia + C. rectus | 0.81 |
| Calprotectin + IL2 + P. intermedia + C. rectus | 0.80 |
| OPG + P. gingivalis | 0.80 |
| MMP9 + P. intermedia + C. rectus | 0.80 |
| MMP8 + IL10 + P. intermedia | 0.80 |
| P. gingivalis + IL2 + IL4 | 0.80 |
| P. gingivalis + IL2 + TNFa | 0.80 |
| T. forsythia + IL10 + IL2 | 0.80 |
| MMP9 + IL13 + P. intermedia + F. nucleatum | 0.80 |
| MMP8 + P. intermedia | 0.80 |
| Calprotectin + IL6 + P. intermedia + C. rectus | 0.80 |
| Calprotectin + IL4 + P. intermedia + C. rectus | 0.80 |
| MMP9 + OPG + P. intermedia + F. nucleatum | 0.80 |
| MMP8 + IL2 + P. intermedia | 0.80 |
| T. forsythia + IL10 | 0.80 |
| IL4 + TNFa + P. intermedia + F. nucleatum | 0.80 |
| P. gingivalis + IL2 | 0.80 |
| MMP9 + IL1beta + P. intermedia | 0.80 |
| MMP8 + Calprotectin + F. nucleatum + C. rectus | 0.80 |
| P. gingivalis + IL1beta + IL4 | 0.80 |
| Calprotectin + P. intermedia + C. rectus | 0.80 |
| MMP9 + IL10 + P. intermedia + F. nucleatum | 0.80 |
| Calprotectin + TNFa + P. intermedia | 0.80 |
| MMP9 + IL2 + P. intermedia | 0.80 |
| Calprotectin + IL1beta + P. intermedia + C. rectus | 0.80 |
| P. gingivalis + IL1beta + IL13 | 0.80 |
| Calprotectin + IL13 + P. intermedia + C. rectus | 0.80 |
| MMP9 + IL4 + P. intermedia + C. rectus | 0.80 |
| MMP9 + IL6 + P. intermedia | 0.80 |
| T. forsythia + IL2 | 0.80 |
| Calprotectin + MMP9 + C. rectus | 0.80 |
| P. gingivalis + IL1beta | 0.80 |
| P. gingivalis + IL1beta + TNFa | 0.80 |
| MMP9 + OPG + P. intermedia | 0.80 |
| P. gingivalis + IL4 + TNFa | 0.80 |
| T. forsythia | 0.80 |
| P. gingivalis + IL4 | 0.80 |
| Calprotectin + ICTP + P. intermedia | 0.80 |

TABLE 3

Biomarker combinations resulting in an AUC (probability) value greater than 90%.

| Signature | AUC |
|---|---|
| MMP8 + T. denticola + ICTP + C. rectus | 0.95 |
| MMP8 + T. denticola + ICTP + P. intermedia | 0.95 |
| MMP9 + T. denticola + ICTP + C. rectus | 0.94 |
| Calprotectin + T. denticola + ICTP + C. rectus | 0.94 |
| T. denticola + IL6 + ICTP + C. rectus | 0.94 |
| MMP8 + T. forsythia + T. denticola + ICTP | 0.94 |
| MMP9 + T. denticola + ICTP + P. intermedia | 0.94 |
| MMP8 + P. gingivalis + T. denticola + ICTP | 0.93 |
| MMP8 + T. denticola + IL1beta + P. intermedia | 0.93 |
| MMP9 + T. forsythia + T. denticola + ICTP | 0.93 |
| MMP8 + Calprotectin + P. gingivalis + P. intermedia | 0.93 |
| Calprotectin + MMP9 + T. denticola + C. rectus | 0.93 |
| T. denticola + ICTP + IL10 + C. rectus | 0.93 |
| T. forsythia + T. denticola + ICTP + IL13 | 0.93 |
| MMP8 + T. denticola + TNFa + P. intermedia | 0.93 |
| MMP8 + Calprotectin + T. denticola + P. intermedia | 0.93 |
| MMP9 + P. gingivalis + T. denticola + ICTP | 0.93 |
| Calprotectin + T. denticola + ICTP + P. intermedia | 0.93 |
| T. denticola + ICTP + TNFa + P. intermedia | 0.93 |
| MMP8 + T. denticola + ICTP + F. nucleatum | 0.93 |
| MMP8 + OPG + T. denticola + P. intermedia | 0.92 |
| MMP8 + T. denticola + IL13 + P. intermedia | 0.92 |
| T. denticola + ICTP + IL13 + P. intermedia | 0.92 |
| T. forsythia + T. denticola + IL6 + ICTP | 0.92 |
| T. denticola + ICTP + IL2 + C. rectus | 0.92 |
| MMP8 + T. denticola + ICTP | 0.92 |
| MMP8 + T. denticola + IL4 + P. intermedia | 0.92 |
| T. denticola + IL6 + ICTP + P. intermedia | 0.92 |
| MMP9 + T. denticola + TNFa + P. intermedia | 0.92 |
| T. denticola + ICTP + IL1beta + C. rectus | 0.92 |
| Calprotectin + MMP9 + T. denticola + P. intermedia | 0.92 |
| T. denticola + ICTP + IL1beta + P. intermedia | 0.92 |
| OPG + T. denticola + ICTP + C. rectus | 0.92 |
| T. denticola + ICTP + IL4 + C. rectus | 0.92 |
| T. denticola + ICTP + C. rectus | 0.92 |
| MMP8 + P. gingivalis + ICTP + P. intermedia | 0.92 |
| MMP8 + T. forsythia + IL1beta + P. intermedia | 0.92 |
| T. denticola + ICTP + IL4 + P. intermedia | 0.92 |
| T. denticola + ICTP + IL13 + C. rectus | 0.92 |
| MMP9 + T. denticola + IL1beta + P. intermedia | 0.92 |
| OPG + T. denticola + ICTP + P. intermedia | 0.92 |
| OPG + T. forsythia + T. denticola + ICTP | 0.92 |
| MMP8 + Calprotectin + T. denticola + C. rectus | 0.92 |
| MMP8 + OPG + T. denticola + C. rectus | 0.92 |
| MMP9 + T. denticola + IL13 + P. intermedia | 0.92 |
| T. denticola + ICTP + IL10 + P. intermedia | 0.92 |
| T. denticola + ICTP + TNFa + C. rectus | 0.92 |
| MMP8 + Calprotectin + T. forsythia + P. intermedia | 0.92 |
| MMP8 + T. denticola + IL6 + P. intermedia | 0.92 |
| MMP9 + T. denticola + IL1beta + C. rectus | 0.92 |
| P. gingivalis + T. denticola + IL6 + ICTP | 0.92 |
| MMP8 + T. denticola + IL1beta + C. rectus | 0.92 |
| T. denticola + ICTP + P. intermedia | 0.92 |
| T. denticola + ICTP + IL2 + P. intermedia | 0.92 |
| MMP8 + T. denticola + P. intermedia | 0.92 |
| MMP8 + P. gingivalis + IL1beta + P. intermedia | 0.92 |
| MMP8 + T. forsythia + T. denticola + IL1beta | 0.92 |
| T. forsythia + T. denticola + ICTP + TNFa | 0.92 |
| MMP8 + T. forsythia + TNFa + P. intermedia | 0.92 |
| MMP9 + OPG + T. denticola + C. rectus | 0.92 |
| T. forsythia + T. denticola + ICTP + IL1beta | 0.92 |
| Calprotectin + T. forsythia + T. denticola + ICTP | 0.92 |
| MMP8 + MMP9 + T. denticola + P. intermedia | 0.92 |
| MMP8 + T. denticola + IL2 + P. intermedia | 0.92 |
| MMP9 + T. denticola + ICTP + F. nucleatum | 0.92 |
| Calprotectin + MMP9 + T. forsythia + P. intermedia | 0.92 |
| MMP9 + OPG + T. denticola + P. intermedia | 0.92 |
| MMP9 + T. denticola + IL4 + P. intermedia | 0.92 |
| MMP9 + T. denticola + ICTP | 0.91 |
| T. forsythia + T. denticola + ICTP + IL10 | 0.91 |
| MMP8 + T. forsythia + ICTP + P. intermedia | 0.91 |
| T. forsythia + T. denticola + ICTP + IL4 | 0.91 |
| MMP8 + P. gingivalis + TNFa + P. intermedia | 0.91 |
| Calprotectin + MMP9 + P. gingivalis + T. denticola | 0.91 |

TABLE 3-continued

Biomarker combinations resulting in an AUC (probability) value greater than 90%

| Signature | AUC |
|---|---|
| Calprotectin + OPG + T. denticola + C. rectus | 0.91 |
| T. forsythia + T. denticola + ICTP + IL2 | 0.91 |
| MMP8 + T. denticola + IL10 + P. intermedia | 0.91 |
| MMP9 + T. forsythia + T. denticola + IL1beta | 0.91 |
| MMP8 + T. forsythia + IL13 + P. intermedia | 0.91 |
| Calprotectin + MMP9 + T. forsythia + T. denticola | 0.91 |
| Calprotectin + T. denticola + IL6 + C. rectus | 0.91 |
| MMP9 + T. denticola + TNFa + C. rectus | 0.91 |
| MMP8 + Calprotectin + T. forsythia + T. denticola | 0.91 |
| Calprotectin + T. denticola + IL13 + P. intermedia | 0.91 |
| MMP8 + MMP9 + T. denticola + C. rectus | 0.91 |
| MMP8 + OPG + T. forsythia + T. denticola | 0.91 |
| Calprotectin + T. denticola + TNFa + P. intermedia | 0.91 |
| T. forsythia + T. denticola + ICTP | 0.91 |
| MMP8 + P. gingivalis + T. denticola + IL1beta | 0.91 |
| MMP8 + T. forsythia + T. denticola + IL13 | 0.91 |
| MMP9 + T. forsythia + T. denticola + IL13 | 0.91 |
| MMP9 + T. forsythia + TNFa + P. intermedia | 0.91 |
| MMP8 + T. denticola + IL6 + C. rectus | 0.91 |
| OPG + P. gingivalis + T. denticola + ICTP | 0.91 |
| Calprotectin + OPG + T. denticola + P. intermedia | 0.91 |
| P. gingivalis + T. denticola + ICTP + IL10 | 0.91 |
| MMP8 + P. gingivalis + IL13 + P. intermedia | 0.91 |
| MMP8 + P. gingivalis + IL4 + P. intermedia | 0.91 |
| MMP8 + T. denticola + IL4 + C. rectus | 0.91 |
| MMP8 + T. denticola + TNFa + C. rectus | 0.91 |
| MMP9 + OPG + T. forsythia + T. denticola | 0.91 |
| MMP9 + T. denticola + IL6 + P. intermedia | 0.91 |
| MMP9 + T. denticola + IL2 + P. intermedia | 0.91 |
| MMP9 + T. denticola + P. intermedia | 0.91 |
| MMP8 + Calprotectin + P. gingivalis + T. denticola | 0.91 |
| MMP9 + P. gingivalis + ICTP + P. intermedia | 0.91 |
| MMP9 + T. forsythia + T. denticola + TNFa | 0.91 |
| MMP8 + T. forsythia + IL4 + P. intermedia | 0.91 |
| MMP9 + P. gingivalis + T. denticola + IL13 | 0.91 |
| MMP9 + T. denticola + IL4 + C. rectus | 0.91 |
| T. denticola + IL6 + ICTP + F. nucleatum | 0.91 |
| MMP8 + T. forsythia + T. denticola + TNFa | 0.91 |
| MMP8 + T. denticola + IL10 + C. rectus | 0.91 |
| Calprotectin + P. gingivalis + T. denticola + ICTP | 0.91 |
| Calprotectin + T. denticola + ICTP + F. nucleatum | 0.91 |
| Calprotectin + T. denticola + IL4 + P. intermedia | 0.91 |
| P. gingivalis + T. denticola + ICTP + IL13 | 0.91 |
| MMP8 + P. gingivalis + T. denticola + IL13 | 0.91 |
| Calprotectin + P. gingivalis + ICTP + P. intermedia | 0.91 |
| MMP8 + T. denticola + IL10 + C. rectus | 0.91 |
| MMP9 + P. gingivalis + IL1beta + P. intermedia | 0.91 |
| MMP8 + OPG + P. gingivalis + T. denticola | 0.91 |
| MMP8 + T. denticola + IL6 + C. rectus | 0.91 |
| MMP9 + OPG + P. gingivalis + T. denticola | 0.91 |
| MMP9 + P. gingivalis + T. denticola + IL1beta | 0.91 |
| MMP9 + T. forsythia + IL13 + P. intermedia | 0.91 |
| MMP8 + T. denticola + IL13 + C. rectus | 0.91 |
| Calprotectin + T. denticola + IL10 + C. rectus | 0.91 |
| MMP8 + T. denticola + C. rectus | 0.91 |
| MMP8 + OPG + T. forsythia + P. intermedia | 0.91 |
| MMP8 + T. forsythia + T. denticola + IL4 | 0.91 |
| MMP9 + T. forsythia + T. denticola + IL4 | 0.91 |
| MMP9 + T. denticola + IL2 + C. rectus | 0.91 |
| MMP9 + T. denticola + IL13 + C. rectus | 0.91 |
| OPG + T. denticola + IL13 + P. intermedia | 0.91 |
| MMP8 + OPG + P. gingivalis + P. intermedia | 0.91 |
| MMP9 + T. forsythia + IL1beta + P. intermedia | 0.91 |
| MMP9 + T. denticola + IL10 + P. intermedia | 0.91 |
| MMP8 + T. denticola + IL2 + C. rectus | 0.91 |
| Calprotectin + T. forsythia + T. denticola + IL13 | 0.91 |
| MMP9 + T. denticola + C. rectus | 0.91 |
| P. gingivalis + T. denticola + ICTP + TNFa | 0.91 |
| MMP8 + P. gingivalis + T. denticola + IL4 | 0.91 |
| MMP8 + P. gingivalis + IL2 + P. intermedia | 0.91 |
| Calprotectin + T. denticola + IL6 + P. intermedia | 0.91 |
| Calprotectin + T. denticola + IL1beta + P. intermedia | 0.91 |
| MMP9 + P. gingivalis + T. denticola + IL4 | 0.91 |
| P. gingivalis + T. denticola + ICTP + IL2 | 0.91 |
| P. gingivalis + T. denticola + ICTP + IL4 | 0.91 |
| T. denticola + IL2 + IL13 + P. intermedia | 0.91 |
| OPG + T. denticola + ICTP + F. nucleatum | 0.90 |
| T. denticola + ICTP + IL10 + F. nucleatum | 0.90 |
| T. denticola + IL1beta + IL13 + P. intermedia | 0.90 |
| T. denticola + IL6 + ICTP | 0.90 |
| MMP8 + T. forsythia + IL10 + P. intermedia | 0.90 |
| T. denticola + ICTP + IL2 + F. nucleatum | 0.90 |
| MMP8 + T. forsythia + IL6 + P. intermedia | 0.90 |
| MMP9 + P. gingivalis + T. denticola + TNFa | 0.90 |
| MMP9 + P. gingivalis + IL13 + P. intermedia | 0.90 |
| MMP9 + T. forsythia + ICTP + P. intermedia | 0.90 |
| T. forsythia + T. denticola + P. intermedia | 0.90 |
| MMP8 + P. gingivalis + P. intermedia | 0.90 |
| MMP8 + MMP9 + P. gingivalis + T. denticola | 0.90 |
| Calprotectin + T. denticola + P. intermedia | 0.90 |
| MMP8 + P. gingivalis + IL6 + P. intermedia | 0.90 |
| Calprotectin + T. forsythia + ICTP + P. intermedia | 0.90 |
| Calprotectin + T. forsythia + IL13 + P. intermedia | 0.90 |
| MMP9 + P. gingivalis + IL4 + P. intermedia | 0.90 |
| MMP9 + P. gingivalis + TNFa + P. intermedia | 0.90 |
| T. denticola + IL10 + IL13 + P. intermedia | 0.90 |
| P. gingivalis + T. denticola + ICTP | 0.90 |
| MMP8 + P. gingivalis + T. forsythia + ICTP | 0.90 |
| MMP8 + P. gingivalis + T. denticola + TNFa | 0.90 |
| Calprotectin + MMP9 + T. forsythia + C. rectus | 0.90 |
| Calprotectin + T. denticola + IL10 + P. intermedia | 0.90 |
| P. gingivalis + T. denticola + P. intermedia | 0.90 |
| MMP8 + P. gingivalis + T. denticola + IL2 | 0.90 |
| MMP8 + MMP9 + T. forsythia + T. denticola | 0.90 |
| Calprotectin + MMP9 + P. gingivalis + T. forsythia | 0.90 |
| MMP9 + P. gingivalis + T. forsythia + ICTP | 0.90 |
| P. gingivalis + T. denticola + ICTP + IL1beta | 0.90 |
| T. denticola + IL6 + IL13 + P. intermedia | 0.90 |
| T. denticola + ICTP + IL13 + F. nucleatum | 0.90 |
| MMP8 + Calprotectin + T. denticola + F. nucleatum | 0.90 |
| MMP8 + P. gingivalis + IL10 + P. intermedia | 0.90 |
| MMP8 + Calprotectin + P. gingivalis + T. forsythia | 0.90 |
| MMP8 + OPG + T. denticola + F. nucleatum | 0.90 |
| MMP8 + T. forsythia + T. denticola + IL2 | 0.90 |
| Calprotectin + T. denticola + IL2 + P. intermedia | 0.90 |
| Calprotectin + T. denticola + IL13 + C. rectus | 0.90 |
| MMP9 + T. forsythia + IL4 + P. intermedia | 0.90 |
| T. denticola + IL13 + IL4 + P. intermedia | 0.90 |
| MMP8 + T. forsythia + IL2 + P. intermedia | 0.90 |
| Calprotectin + MMP9 + T. denticola + F. nucleatum | 0.90 |
| T. denticola + ICTP + TNFa + F. nucleatum | 0.90 |
| T. denticola + IL13 + TNFa + P. intermedia | 0.90 |
| Calprotectin + MMP9 + P. gingivalis + C. rectus | 0.90 |
| MMP9 + T. forsythia + T. denticola + IL10 | 0.90 |
| MMP9 + T. forsythia + IL2 + P. intermedia | 0.90 |
| MMP8 + MMP9 + P. gingivalis + P. intermedia | 0.90 |
| Calprotectin + T. denticola + IL2 + C. rectus | 0.90 |
| Calprotectin + T. denticola + C. rectus | 0.90 |
| T. denticola + IL13 + P. intermedia | 0.90 |
| Calprotectin + T. denticola + ICTP | 0.90 |
| Calprotectin + T. denticola + TNFa + C. rectus | 0.90 |
| OPG + T. denticola + IL4 + P. intermedia | 0.90 |
| T. denticola + ICTP + IL4 + F. nucleatum | 0.90 |
| T. denticola + ICTP + IL1beta + F. nucleatum | 0.90 |
| MMP8 + T. forsythia + T. denticola | 0.90 |
| MMP8 + T. forsythia + P. intermedia | 0.90 |
| MMP9 + T. forsythia + T. denticola | 0.90 |
| MMP8 + P. gingivalis + T. denticola + IL10 | 0.90 |
| Calprotectin + OPG + P. gingivalis + P. intermedia | 0.90 |
| Calprotectin + P. gingivalis + TNFa + P. intermedia | 0.90 |
| MMP9 + T. forsythia + T. denticola + IL6 | 0.90 |
| MMP9 + T. forsythia + IL10 + P. intermedia | 0.90 |
| T. denticola + ICTP + F. nucleatum | 0.90 |
| Calprotectin + T. denticola + IL4 + C. rectus | 0.90 |
| OPG + T. denticola + TNFa + P. intermedia | 0.90 |
| MMP8 + T. forsythia + T. denticola + IL6 | 0.90 |
| MMP8 + T. forsythia + T. denticola + IL10 | 0.90 |
| MMP8 + T. forsythia + ICTP + C. rectus | 0.90 |
| MMP8 + T. denticola + IL1beta + F. nucleatum | 0.90 |
| Calprotectin + P. gingivalis + IL4 + P. intermedia | 0.90 |

TABLE 3-continued

Biomarker combinations resulting in an AUC
(probability) value greater than 90%

| Signature | AUC |
|---|---|
| MMP9 + P. gingivalis + T. denticola + IL6 | 0.90 |
| Calprotectin + P. gingivalis + IL13 + P. intermedia | 0.90 |
| MMP9 + OPG + P. gingivalis + P. intermedia | 0.90 |
| MMP9 + P. gingivalis + IL2 + P. intermedia | 0.90 |
| T. denticola + IL6 + TNFa + P. intermedia | 0.90 |
| T. denticola + IL2 + TNFa + P. intermedia | 0.90 |
| T. denticola + P. intermedia + C. rectus | 0.90 |
| MMP9 + OPG + T. denticola + F. nucleatum | 0.90 |
| OPG + T. denticola + IL6 + P. intermedia | 0.90 |
| OPG + T. denticola + IL1beta + P. intermedia | 0.90 |
| MMP8 + P. gingivalis + T. denticola | 0.90 |
| MMP9 + P. gingivalis + T. denticola | 0.90 |
| Calprotectin + OPG + T. forsythia + P. intermedia | 0.90 |
| Calprotectin + T. denticola + IL1beta + C. rectus | 0.90 |
| MMP9 + OPG + T. forsythia + P. intermedia | 0.90 |
| MMP9 + P. gingivalis + T. forsythia + IL13 | 0.90 |
| T. denticola + IL10 + TNFa + P. intermedia | 0.90 |
| Calprotectin + OPG + T. forsythia + C. rectus | 0.90 |
| Calprotectin + P. gingivalis + IL10 + P. intermedia | 0.90 |
| Calprotectin + T. forsythia + TNFa + P. intermedia | 0.90 |
| T. denticola + IL6 + IL4 + P. intermedia | 0.90 |
| T. denticola + IL2 + IL4 + P. intermedia | 0.90 |
| MMP9 + P. gingivalis + T. denticola + IL2 | 0.90 |
| MMP9 + T. denticola + IL1beta + F. nucleatum | 0.90 |
| T. forsythia + T. denticola + IL6 + IL13 | 0.90 |
| Calprotectin + P. gingivalis + IL1beta + P. intermedia | 0.90 |
| MMP9 + P. gingivalis + T. forsythia + TNFa | 0.90 |
| T. denticola + IL6 + IL13 + C. rectus | 0.90 |
| Calprotectin + P. gingivalis + P. intermedia | 0.90 |
| MMP8 + P. gingivalis + T. forsythia + IL1beta | 0.90 |
| MMP8 + P. gingivalis + T. forsythia + TNFa | 0.90 |
| T. denticola + IL6 + IL2 + P. intermedia | 0.90 |
| T. denticola + IL10 + IL4 + P. intermedia | 0.90 |
| MMP9 + P. gingivalis + P. intermedia | 0.90 |
| T. denticola + ICTP + IL10 | 0.90 |
| MMP8 + MMP9 + T. forsythia + P. intermedia | 0.90 |
| MMP9 + P. gingivalis + T. forsythia + IL1beta | 0.90 |
| MMP9 + T. forsythia + T. denticola + IL2 | 0.90 |
| OPG + T. denticola + P. intermedia | 0.90 |
| MMP8 + P. gingivalis + T. forsythia + IL4 | 0.90 |
| MMP8 + P. gingivalis + T. denticola + IL6 | 0.90 |
| MMP8 + T. forsythia + IL1beta + C. rectus | 0.90 |
| Calprotectin + P. gingivalis + IL2 + P. intermedia | 0.90 |
| Calprotectin + T. forsythia + IL1beta + P. intermedia | 0.90 |
| MMP9 + P. gingivalis + T. forsythia + IL4 | 0.90 |
| MMP9 + P. gingivalis + IL6 + P. intermedia | 0.90 |
| T. denticola + P. intermedia + F. nucleatum | 0.90 |
| MMP8 + OPG + T. denticola | 0.90 |
| MMP8 + P. gingivalis + T. forsythia + IL13 | 0.90 |
| MMP8 + T. denticola + IL1beta | 0.90 |
| OPG + T. denticola + ICTP | 0.90 |
| Calprotectin + OPG + T. forsythia + T. denticola | 0.90 |

In various aspects of methods of the invention, an AUC probability value that is at least about 60% or higher is indicative of oral disease. Indeed, the present invention contemplates methods wherein an AUC value is calculable, and thereby prediction of a disease state at a probability that is greater than about 61%, 62%, 63%, 64%, 65%, 66%, 67%, 68%, 69%, 70%, 71%, 72%, 73%, 73%, 74%, 74%, 75%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more According to methods of the invention, biomarker levels that are determined and used for the generation of ROC and AUC curves are protein levels. Methods for detection of protein levels in a sample are well known and routinely practiced in the art. For example the worker of ordinary skill in the art will appreciate that ELISA and western blotting methodologies are amenable to methods of the invention, as well as techniques such as a proximity-ligation strategy (3PLA) (Schallmeiner et al., Nature Methods (2006) 4, 135-137), rolling circle amplification (RCA)-enhanced protein detection on antibody microarrays (Haab, et al., Meth. Mol. Biol (2006) 328:15-29), high throughput microarray analyses as described, for example in Lee, et al., Analyst, 2008, 133, 975-983 and other well known biomarker detection methods as described, for example, in Liszewski, Genetic Eng. Biotech. News., Mar. 15, 2006 (Vol. 26, No. 6), Pan, et al., Molecular & Cellular Proteomics (2005) 4:182-190, Yan, et al., J. Mass Spect. (2005) 40 (4): 444-451, and Archarya, et al., J. Am. Chem. Soc. (2007) 129 (51):15824-15829. Additional methods for protein detection well known in the art are described, for example, in Coligan, et al. (eds), *Current Protocol in Protein Science*, (John Wiley and Sons, last updated May 2008).

In other aspects, the levels are measured using DNA or RNA by methods well known and routinely practiced in the art. A comprehensive guide to methods for detection of polynucleotides is found, for example, in Ausubel, et al., (eds) *Current Protocols in Molecular Biology* (John Wiley and Sons, last updated July 2008), and Sambrook, et al., Molecular Cloning: A Laboratory Manual, (Cold Spring Harbor 2000.

Samples contemplated for use in carrying out the methods of the invention include a bodily fluid, tissue and organ. In various aspects, a sample can be saliva, a gingival tissue specimen, or gingival crevicular fluid (GCF). Methods for sample collection will be readily appreciated by those of ordinary skill in the art.

In still further aspects of the invention, a method for treating oral disease in an individual comprising the step of inhibiting activity of one or more biomarkers identified in methods of the invention to be indicative of oral disease in said individual is provided. In an embodiment of the methods, the biomarker activity is inhibited by an antibody, wherein said antibody specifically binds to a biomarker and inhibits biomarker binding and/or prevents biomarker signaling and/or otherwise inhibits its activity. Inhibition of a detected biomarker is therefore effected by use of antibodies, peptides or small molecules against biomarkers that are capable of inhibiting the activity of said biomarkers. In still other aspectd detected biomarkers are inhibited using known binding partners, or fragments of variants of known binding partners of the identified biomarkers, wherein the biding partner, or fragment or variant thereof specifically binds to and abrogate the function and/or activity of the biomarkers.

In other aspects of these methods, expression of the biomarker is inhibited and in a specific embodiment, expression of a biomarker or biomarkers is inhibited by inhibitory RNA. Because reduction in biomarker mRNA levels can lead to alteration in biomarker protein products of expression as well, such resultant alterations can also be measured. Production and use of inhibitory RNA, including, for example and without limitation, RNA interference, antisense RNA technology, shRNA, and/or ribozymes are described in Dykxhoom et al., (2003), Nature Review, 4: 457-467, 2003; and Mittal, (2004) Nature Reviews, 5: 355-365.

Methods of reducing biomarker activity are contemplated by the invention through administration of a composition to an individual in need thereof. The administration is contemplated to be useful as either a therapeutic or prophylactic composition. In general, the compositions are used in order to treat oral disease by reducing or eliminating the biomarker expression or activity in gingival cells. "Reducing or eliminating" refers to a reduction or elimination of detectable amounts of the biomarker gene product by an amount in the range of at least about 10% to about 100%, or at least about 25% to 100%, at least about 50% to about 100%, and from about 75% to about 100%. Methods of the invention are therefore for inhibiting biomarker expression with a reduction of said biomarker transcription and/or biomarker protein translation, and/or biomarker protein activity by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% in an individual. The result of the reduction in biomarker expression or activity will ultimately be a reduction in the AUC probability value as determined by the methods of the invention.

The present invention also provides a kit for carrying out the various methods of the invention, the kit comprising a sterile container for sample collection and one or more components selected from the group consisting of one or more reagents for performing the assay, a calibration standard and a quality control sample. In another embodiment of the present invention, kits are provided which contain the necessary reagents to carry out the assays of the present invention. In one aspect, the invention provides a compartment kit to receive, in close confinement, one or more containers which comprises: (a) a first container comprising a probe or antibody that recognize a biomarker of the invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

As an additional aspect, the various kits contemplated by the invention contain suitable reagents for carrying out assays including but not limited to immunological assays (including enzyme-linked immunosorbent assays (ELISAs) and radio-immunoassay), polymerase chain reaction (PCR) analyses, quantitative PCR (qPCR) analyses, and buffers and other standard reagents (e.g., primers) used in carrying out the assays, all of which are known to one of ordinary skill in the art. Preferably, the kit contains an insert that describes use of the kit.

While the present invention has been described in terms of various embodiments and examples, it is understood that variations and improvements will occur to those skilled in the art. Therefore, only such limitations as appear in the claims should be placed on the invention.

EXAMPLES

Example 1

Univariate Analyses: A total sample of 50 subjects, 9 who have moderate/severe periodontitis and 41 who do not were studied. Sixteen biomarkers were determined. There are missing values for some subjects in each of the biomarkers; 45 subjects have values for all of the biomarkers.

Table 4 (below) displays the following values for each biomarker: (A) the median and number of subjects evaluated for those without moderate/severe periodontitis; (B) the median and number of subjects evaluated for those with moderate/severe periodontitis; (C) the area-under-the ROC curve (AUC); and (D) the p-value corresponding to a test of a difference between the medians (Wilcoxon Rank Sum Test).

TABLE 4

Univariate summary statistics for each biomarker
Median (N measured)

| Biomaker | Healthy/Mild Periodontitis | Moderate/Severe Periodontitis | AUC | p-value |
|---|---|---|---|---|
| MMP-8 | 56.0 (41) | 349.5 (9) | 0.85 | <0.001 |
| MMP-9 | 231.8 (41) | 859.7 (9) | 0.76 | 0.015 |
| IL-2 | 7.2 (41) | 6.0* (8) | 0.66 | 0.134 |
| TNF-α | 8.2 (41) | 8.0* (8) | 0.66 | 0.149 |
| IL-5 | 20.0* (41) | 20.0* (8) | 0.65 | 0.089 |
| Calprotectin | 42.4 (41) | 66.4 (9) | 0.63 | 0.240 |
| ICTP | 0.7 (39) | 0.9 (9) | 0.63 | 0.236 |
| IL-1β | 206.7 (41) | 600.7 (8) | 0.60 | 0.365 |
| IL-10 | 123.5 (41) | 60.0* (8) | 0.60 | 0.353 |
| Osteopontin | 1.8 (41) | 1.7 (7) | 0.59 | 0.465 |
| IL-6 | 6.0* (41) | 78.7 (8) | 0.56 | 0.543 |
| IL-13 | 200* (41) | 200.0* (8) | 0.55 | 0.653 |
| IL-4 | 42.8 (41) | 19.5 (8) | 0.55 | 0.681 |
| Osteocalcin | 17.1 (41) | 18.4 (9) | 0.54 | 7.43 |
| Laminin | 16.8 (41) | 16.5 (9) | 0.52 | 0.836 |
| IFN-γ | 60.0* (41) | 60.0* (8) | 0.51 | 0.958 |

*Media equal to detection threshold

Table 5 (below) contains additional information on MMP-8 and MMP-9. The cut point determined for each biomarker was that value where the difference between sensitivity and specificity was as small as possible.

TABLE 5

Diagnostic Properties of MMP-8 and MMP-9

| Maker | Cut Pt. | Above Cut Pt. | Healthy/Mild Periodontitis | Moderate/Severe Periodontitis | p-value | Sens | Spec | PPV | NPV |
|---|---|---|---|---|---|---|---|---|---|
| MMP-9 | 124.1 | N | 31 | 1 | 0.001 | 0/89 | 0.76 | 0.44 | 0.97 |
|  |  | Y | 10 | 8 |  |  |  |  |  |
| MMP-9 | 370.1 | N | 26 | 3 | 0.200 | 0.67 | 0.63 | 0.29 | 0.90 |
|  |  | Y | 15 | 6 |  |  |  |  |  |

Multivariate Analyses—CART and Random Forest Methods: CART (Classification and Regression Trees) is a method that seeks to find the best biomarkers and the best cut-points of those biomarkers that discriminate between subjects with periodontitis and subjects without periodontitis. However, one limitation of CART is that no statistical significance (i.e., p-value) of the model can be derived. Random Forests is a method that repeatedly resamples from the data and fits a CART model to each resampled set of data. An overall "importance score" is then derived for each biomarker that essentially reflects how often each biomarker appears in each CART model created from each resampled set of data. Thus, rather than a final "model", a list of biomarkers is generated that may prove useful for predicting moderate/severe periodontitis.

Table 6 (below) contains the importance scores of each biomarker, listed in descending order of importance score, based only upon the 45 subjects who had measurements for all 16 biomarkers. There is an obvious separation of MMP-8 from the others, and MMP-9 has a rather weak importance score. There are also indications that ICTP, calprotectin, and IL-1β hold some promise, confirming the results in Table 4.

TABLE 6

Importance scores of 16 biomarkers in Random Forest models

| Biomaker | Importance Score |
|---|---|
| MMP-8 | 1.83 |
| ICTP | 1.06 |
| Calprotectin | 1.05 |
| IL-1β | 0.94 |
| MMP-9 | 0.86 |
| TNF-α | 0.73 |
| Osteopontin | 0.69 |
| Osteocalcin | 0.54 |
| IL-10 | 0.52 |
| Laminin | 0.50 |
| IL-6 | 0.41 |
| IL-4 | 0.41 |
| IL-2 | 0.29 |
| IL-13 | 0.25 |
| IL-5 | 0.09 |
| IFN-γ | 0.05 |

Multivariate Analyses—Regression Methods: As an alternative to CART and Random Forests, multivariate logistic regression was used, simultaneously modeling the presence or absence of periodontitis in each subject on all of the corresponding biomarker values. The final model with a reduced subset of the biomarkers was then identified using stepwise regression techniques. The next step was to resample (bootstrap) from the original data and apply stepwise logistic regression techniques to identify the best subset of biomarkers based upon this resampled data set. This resampling and model-fitting process was repeated 1000 times, giving 1000 possible combinations of the best set of biomarkers to predict presence or absence of moderate/severe periodontitis.

Table 7 (below) contains the percentages that each biomarker appeared in the 1000 combinations; the biomarkers are sorted in descending order of percentage, based only upon the 45 subjects who had measurements for all 16 biomarkers. As in Table 4, MMP-8 and MMP-9 are likely candidate markers for moderate/severe periodontitis. However, Table 7 gives less support to calprotectin, IL-1β, and ICTP.

TABLE 7

Percentage that each biomarker appeared in the 1000 combinations of 16 biomarkers in Random Forest models

| Biomaker | Percentage |
|---|---|
| MMP-8 | 0.89 |
| MMP-9 | 0.67 |
| Osteopontin | 0.41 |
| Osteocalcin | 0.37 |
| IL-5 | 0.34 |
| IL-2 | 0.32 |
| IL-1β | 0.32 |
| IL-6 | 0.30 |
| IL-4 | 0.29 |
| Calprotectin | 0.28 |
| TNF-α | 0.25 |
| ICTP | 0.21 |
| Laminin | 0.19 |
| IL-13 | 0.19 |
| IL-10 | 0.13 |
| IFN-γ | 0.10 |

Using three different statistical approaches (Wilcoxon Rank Sum Test/AUC, CART/Random Forests, and Bootstrapped Stepwise Logistic Regression), the data indicate that MMP-8 is far and away the best biomarker for detecting moderate/severe periodontitis. There are modest indications that MMP-9, ICTP, calprotectin, and IL-1β are also possible biomarkers for moderate/severe periodontitis.

Figure 7:
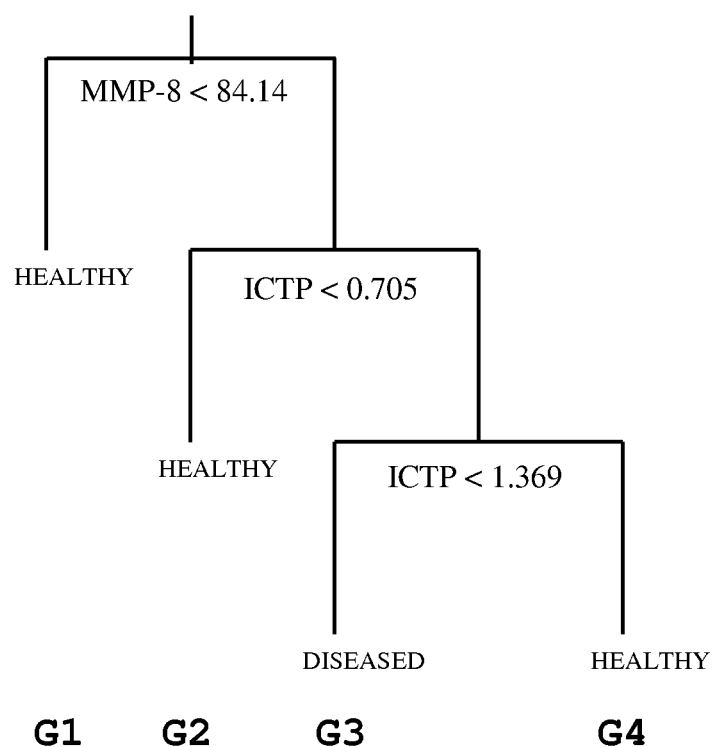
FIG. 7 depicts a classification and regression tree analysis (CART) showing multiple combinations of biomarkers that can discriminate among various disease states.

CART was used again to find the combination of MMP-8, MMP-9, calprotectin, IL-1β and ICTP that best discriminates between those with moderate/severe periodontitis (diseased) and those without moderate/severe periodontitis (healthy). The final model is shown in FIG. 7; this model divides subjects into four groups (labeled as G1-G4). G3 is defined to be subjects with moderate/severe periodontitis and are those subjects with MMP-8 greater than 84.145 and ICTP between 0.705 and 1.37. Using this classification scheme, 4 of 6 subjects with moderate/severe periodontitis were correctly classified (sensitivity=0.67) and 38 of 39 subjects without moderate/severe periodontitis (specificity=0.97). Put another way, those classified as diseased in FIG. 7 have 76 times the odds of moderate/severe periodontitis as those classified as healthy in FIG. 1 (odds ratio=76; 95% confidence interval=[6, 1036]).

Example 2

Another clinical study was approved by the University of Michigan Health Sciences Institutional Review Board (IRB) and registered with the NIH clinical trials database. Upon receiving written consent, a total of 100 human subjects aged 18 years and older were evaluated at the Michigan Center for Oral Health Research (MCOHR). All subjects possessed at least 20 teeth and had received no periodontal treatment or antibiotic therapy for medical or dental reasons three months prior to the investigation. In addition, the subjects did not previously undergo any long-term use of medications affecting periodontal status such as anti-inflammatory drugs before the study.

Figure 8:
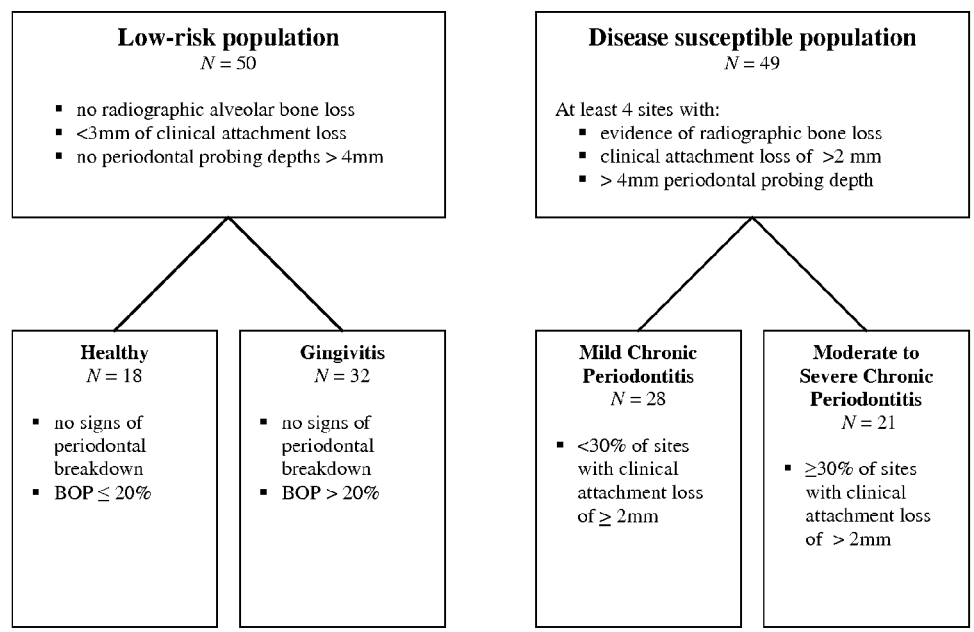
FIG. 8 depicts the stratification of the low-risk population and the disease-susceptible population into four groups following the criteria of clinical attachment loss, periodontal probing depth, radiographic bone loss, and bleeding on probing (BOP).

Subjects were enrolled into a low-risk disease population (N=50) and a disease susceptible population (N=49; one patient dropped out at experimental baseline). Subjects from the low-risk disease population exhibited <3 mm of attachment loss, no periodontal probing depths of >4 mm, and no radiographic alveolar bone loss. Disease susceptible subjects, exhibited at least 4 sites with evidence of radiographic bone loss, at least 4 sites with attachment loss of >3 mm, and at least 4 sites with >4 mm periodontal probing depth (FIG. 8).

Subjects were excluded if they possessed a history of metabolic bone diseases such as rheumatoid arthritis or postmenopausal osteoporosis. Women who were pregnant were also excluded from the study.

All teeth except third molars were assessed for periodontal clinical measures by two calibrated examiners. These parameters included probing pocket depth (PD), clinical attachment level (CAL), plaque index (PI, dichotomously), gingival redness index (GRI, dichotomously), and bleeding on probing (BOP, dichotomously).

Standardized periapical digital radiographs (Schick Technologies, Long Island City, N.Y., USA) were taken in the posterior dentition of all the subjects using a parallel technique for the determination of alveolar bone height. Using a computer software measurement tool (Emago® Advanced, Oral Diagnostic Systems, Amsterdam, The Netherlands), the interproximal alveolar bone levels of both premolars and first and second molars were measured on a digital computer screen by one calibrated examiner. The distance from the alveolar bone crest to the cemento-enamel junction (CEJ) or the restoration margin reference was recorded as the radiographic alveolar bone level (RBL).

Subgingival plaque biofilm was collected from the mesiobuccal surfaces of all teeth and immediately placed into labeled vials containing 500 μl of stabilizing buffer to prevent mRNA degradation (RNA Protect™, Ambion, Austin, Tex.) as previously described (Shelburne et al., 2008, PLoS ONE 3, e1984). After vortexing for 30 seconds, the samples were stored at 4° C. until they were sent to the laboratory for analysis.

The detection of *Aggregatibacter actinomycetemcomitans, Campylobacter rectus, Fusobacterium nucleatum, Prevotella intermedia, Porphyromonas gingivalis, Tannerella forsythia* and *Treponema denticola* in pooled plaque samples were evaluated by real-time quantitative PCR (qPCR) as described (Mullally et al., 2000, J Periodontal Res 35: 232-241; Shelburne et al., 2000, J Microbiol Methods 39: 97-107) using primers specific for the hypervariable segments of the 16S rRNA genes of each bacterium (Table 8). The percentage of the total flora for each species was calculated by dividing the number of target organisms by the total number of bacteria as determined by qPCR using 16S rRNA primers that reacted with all bacterial species. Data are represented on a patient-based assessment.

TABLE 8

Primers for qPCR analysis of plaque biofilm bacteria.

| Bacterial Species | Forward primer (5'-3') | SEQ ID NO | Reverse Primer (5'-3') | SEQ ID NO |
|---|---|---|---|---|
| A. actinomycetemcomitans | GGCACGTAGGCGGACCTT | 1 | ACCAGGGCTAAAGCCCAATC | 2 |
| C. rectus | TTTCGGAGCGTAAACTCCTTTTC | 3 | TTTCTGCAAGCAGACACTCTT | 4 |
| F. nucleatum | ACCAGCGTTTGACATCTTAGGAATG | 5 | AGCCATGCACCTGTCTTTAG | 6 |
| P. intermedia | AGATTGACGGCCCTATGGGT | 7 | CCGGTCCTTATTCGAAGGGTA | 8 |
| P. gingivalis | CATAGATATCACGAGGAACTCCGATT | 9 | AAACTGTTAGCAACTACCGATGTGG | 10 |
| T. forsythia | GGGTGAGTAACGCGTATGTAACCT | 11 | ACCCATCCGCAACCAATAAA | 12 |
| T. denticola | CGTTCCTGGGCCTTGTACA | 13 | TAGCGACTTCAGGTACCCTCG | 14 |
| Universal | CCATGAAGTCGGAATCGCTAG | 15 | GCTTGACGGGCGGTGT | 16 |

Unstimulated whole saliva was collected with passive drooling into sterile plastic tubes from all the subjects at the beginning of the screening appointment (Mandel et al., 1976, Oral Sci Rev: 25-47). The collection was completed as soon as 2 mL of whole saliva was collected or a maximum of 15 minutes of sampling time had been reached. Subsequently, the samples were placed on ice, aliquoted and supplemented with a proteinase inhibitor combination of 1% aprotinin and 0.5% phenylmethylsulphonyl fluoride (PMSF) prior to storage at −80° C.

Protein biomarker levels were determined using colorimetric-based enzyme-linked immunosorbant assays (ELISAs), fluorescence-based protein microarrays, and radioimmunoassay (RIA), run according to manufacturer protocols. ELISAs (R&D Systems Inc., Minneapolis, Minn., USA) were used for measurement of MMP-8, MMP-9, calprotectin, and osteoprotegerin (OPG). Detection of the cytokines IL-1β, IL-2, IL-4, IL-5, IL-6, IL-10, IL-13, tumor necrosis factor-α (TNF), and interferon (IFN)-γ was accomplished using a protein microarray (Whatman Inc., Florham Park, N.J., USA). Concentration of pyridinoline cross-links of type I collagen (ICTP) was determined using an RIA (Immunodiagnostic Systems Inc., Fountain Hills, Ariz., USA).

Prior to each assay, whole saliva samples were thawed at room temperature (RT) and microcentrifuged for 5 min to obtain cell-free supernatant for analysis. In the case of the ELISAs, absorbance measurements (Molecular Devices Corporation, Sunnyvale, Calif., USA) were collected using a primary signal at 450 nm with background subtraction of the 540 nm signal. A fluorescence scanner (Molecular Devices Corporation, Sunnyvale, Calif., USA) was operated to collect Cy5 fluorescence signal from the cytokine protein microarrays. Data collection of the protein microarray signals was performed using Genepix Pro (Molecular Devices Corporation, Sunnyvale, Calif., USA) software.

Basic demographics were summarized with means and proportions for each subject group; between-group comparisons were made with a one-way analysis of variance (ANOVA). Biomarker levels were summarized with medians for each group; between-group comparisons were made with a Kruskal-Wallis test. Areas Under the Curve (AUCs) for Receiver Operating Characteristic (ROC) curves were estimated non-parametrically (Bamber, 1975, Br J Math Stat Psychol 12: 387-415). Thresholds for biomarkers were preselected as those values for which sensitivity and specificity were as equal as possible. ROC curves and corresponding AUCs for multiple biomarker combinations were based upon predicted probabilities of diseased subjects from a logistic regression model in which a subject's biomarker levels were dichotomized as being either above or below their corresponding thresholds. Furthermore, the biomarkers and microbial gene biofilm levels were ranked in importance via Random Forest methods (Breiman, 2001, Machine Learning 45: 5-32). A statistical significance was defined as a p<0.05.

Fifty-seven female (74% Caucasian) and 42 male (81% Caucasian) subjects were enrolled in the study ranging in age from 20 to 77 years. Following the recording of both periodontal clinical and radiographic parameters, the 99 subjects were stratified into four groups (FIG. 8) (Borrell et al., 2005, J Clin Periodontol 32 Suppl 6: 132-158; Tonetti et al., 2005, Group C consensus report of the 5th European Workshop in Periodontology. J Clin Periodontol 32 Suppl 6: 210-213).

From the low-risk disease population, 18 subjects were stratified as healthy (Group 1) with no signs of periodontal breakdown and with BOP≤20%. Thirty-two subjects were categorized as possessing gingivitis (BOP>20%) and no alveolar bone loss (Group 2). From the disease susceptible population, 28 subjects exhibiting <30% of sites with CAL of >2 mm were classified as mild chronic periodontitis (Group 3), and 21 subjects were labeled as moderate-severe chronic periodontitis with >30% of sites with CAL of >2 mm (Group 4).

Dental and periodontal data (Table 9) were significantly different among the four groups for the mean number of teeth (25-28, $p<0.001$), BOP (12%-64%, $p<0.001$), GRI (13%-56%, $p<0.001$), presence of plaque biofilm (13%-56%, $p<0.001$), mean probing depths (1.49 mm-3.03 mm, $p<0.001$), sites with PD greater than 4 mm (0%-20%, $p<0.001$), mean AL (0.59 mm-2.93 mm, $p<0.001$), and mean RBL (1.89 mm-4.33 mm, $p<0.001$). Additionally, the prevalence of smoking was significantly higher in groups 3 and 4 (36% and 81% respectively, $p<0.001$). The demographics for age, gender, and ethnicity, however, were not statistically different and were balanced among the four groups.

TABLE 9

Patient demographics and clinical parameters stratified by level of disease.

| | A | B | C<br>Mild Chronic | D<br>Moderate to<br>Severe Chronic | P-values<br>comparing<br>A, B, C & D | | P-value<br>comparing |
|---|---|---|---|---|---|---|---|
| | Healthy | Gingivitis | Periodontitis | Periodontitis | Overall | Trend | A & B vs C & D |
| Number of Subjects | 18 | 32 | 28 | 21 | n/a | n/a | n/a |
| % Male | 56 | 41 | 39 | 38 | 0.67 | 0.32 | 0.47 |
| % White | 78 | 78 | 68 | 86 | 0.54 | 0.80 | 0.78 |
| % Smoker | 0 | 19 | 36 | 81 | <0.001 | <0.001 | <0.001 |
| Mean Number of Teeth | 28 | 27 | 26 | 25 | <0.001 | <0.001 | <0.001 |
| Mean Age | 45 | 42 | 53 | 50 | 0.02 | 0.03 | 0.002 |
| % BOP[a] | 12 | 31 | 52 | 64 | <0.001 | <0.001 | <0.001 |
| % GI[b] | 13 | 22 | 49 | 56 | <0.001 | <0.001 | <0.001 |
| % PI[c] | 24 | 26 | 57 | 61 | <0.001 | <0.001 | <0.001 |
| Mean PD[d] | 1.49 | 1.65 | 2.29 | 3.03 | <0.001 | <0.001 | <0.001 |
| % Sites PD ≥5 mm | 0 | 0 | 7 | 20 | <0.001 | <0.001 | <0.001 |
| Mean CAL[e] | 0.59 | 0.72 | 1.69 | 2.93 | <0.001 | <0.001 | <0.001 |
| Mean BL[f] | 1.89 | 2.00 | 3.13 | 4.33 | <0.001 | <0.001 | <0.001 |

[a]Bleeding on probing (%)
[b]Gingival index (%)
[c]Plaque index (%)
[d]Periodontal probing depth
[e]Clinical attachment loss
[f]Radiographic alveolar bone level Example 3

Data from the analysis of putative biomarkers of periodontal disease are shown in Table 10. Given that the majority (>70%) of the subjects failed to reveal protein levels of IL-5 and IFN-γ in their whole saliva, these proteins were not included.

Median levels of protein concentrations were increased in subjects with advancing stages of periodontal disease as compared to the healthier individuals for MMP-8 ($p<0.001$), MMP-9 ($p=0.001$), calprotectin ($p=0.023$). Increased levels of osteoprotegerin (OPG) demonstrated a significant ability to predict health ($p=0.007$; Table 10). Various trends were noted for other biomarkers including ICTP, IL-1, and IL6, but these were not significant. Random Forest methods were ranking the importance of MMP-8 with a score of 7.1 and OPG with a score of 6.3 reflecting the highest importance level amongst the biomarkers in this dataset.

TABLE 10

Median levels (ranges) and diagnostic ability of salivary biomarkers and plaque biofilm pathogens.

| | Conc. | A Healthy Median (range) | B Gingivitis Median (range) | C Mild Chronic Periodontitis Median (range) | D Moderate & Severe Chronic Periodontitis Median (range) | P-values comparing A, B, C & D | P-values comparing A & B vs. C & D | AUC | Importance Score via Random Forest |
|---|---|---|---|---|---|---|---|---|---|
| Biomarker | | | | | | | | | |
| MMP8 | ng/mL | 23.6 (2.5, 322.5) | 54.1 (1, 473.9) | 129.9 (8.5, 978.9) | 203.8 (10.1, 2681.1) | <0.001 | <0.001 | 0.75 | 7.1 |
| OPG | pg/mL | 2.3 (1.4, 6.6) | 2.7 (1.2, 6.2) | 1.9 (0.2, 10.1) | 1.6 (0.5, 11.8) | 0.056 | 0.007 | 0.62 | 6.3 |
| MMP9 | ng/mL | 106.4 (10, 1185.7) | 225.8 (4.9, 1732.2) | 301.6 (4.6, 3348.1) | 780.8 (10.4, 9778.2) | 0.002 | 0.001 | 0.72 | 5.1 |
| Calprotectin | ng/mL | 3.0 (1.3, 10) | 3.5 (0, 24.6) | 4.3 (0, 17.8) | 5.4 (1.7, 97.6) | 0.082 | 0.023 | 0.68 | 4.7 |
| IL1β | pg/mL | 158.6 (0, 6000) | 206.7 (0, 3856.9) | 247.5 (24.1, 3120) | 462.2 (15.7, 6000) | 0.157 | 0.059 | 0.72 | 3.7 |
| ICTP | ng/mL | 0.9 (0, 4) | 0.8 (0, 4) | 0.6 (0, 5.4) | 0.9 (0, 13.9) | 0.195 | 0.185 | 0.58 | 3.2 |
| IL6 | pg/mL | 0.0 (0, 1915) | 22.1 (0, 8784.9) | 14.6 (0, 5259.7) | 88.7 (0, 10816.9) | 0.127 | 0.092 | 0.71 | 2.2 |
| IL10 | pg/mL | 881.4 (0, 11088.8) | 120.6 (0, 45488.9) | 1153.1 (0, 24581.4) | 1445.1 (0, 30633.1) | 0.618 | 0.329 | 0.68 | 1.9 |
| TNFα | pg/mL | 9.8 (0, 1788.3) | 0.0 (0, 3720.5) | 8.1 (0, 4370.2) | 0.0 (0, 8212.7) | 0.483 | 0.954 | 0.64 | 1.8 |
| IL13 | pg/mL | 14.3 (0, 83151.1) | 0.0 (0, 92423.8) | 0.0 (0, 76046) | 169.9 (0, 75445.2) | 0.780 | 0.783 | 0.64 | 1.5 |
| IL4 | pg/mL | 0.0 (0, 5315.1) | 0.0 (0, 6579.3) | 54.4 (0, 14588) | 69.5 (0, 11714.3) | 0.377 | 0.086 | 0.71 | 1.3 |
| IL2 | pg/mL | 0.0 (0, 3718.1) | 0.0 (0, 6000) | 8.0 (0, 6205.5) | 0.0 (0, 14400.1) | 0.421 | 0.178 | 0.69 | 1.2 |
| Pathogen | | | | | | | | | |
| T. denticola | % | 0.11 (0, 0.54) | 0.10 (0, 2.95) | 1.53 (0, 5.25) | 2.34 (0.79, 6.63) | <0.001 | <0.001 | 0.86 | 13.7 |
| P. gingivalis | % | 0.05 (0, 0.9) | 0.04 (0, 0.66) | 0.53 (0, 2.36) | 1.00 (0.43, 3.24) | <0.001 | <0.001 | 0.84 | 9.6 |
| T. forsythia | % | 0.09 (0, 0.88) | 0.07 (0, 0.8) | 0.71 (0, 3.16) | 1.26 (0.11, 3.55) | <0.001 | <0.001 | 0.85 | 8.4 |
| P. intermedia | % | 0.11 (0, 1.17) | 0.20 (0, 1.99) | 0.82 (0, 3.77) | 1.85 (0, 3.5) | <0.001 | <0.001 | 0.79 | 6.7 |
| C. rectus | % | 0.00 (0, 1.22) | 0.00 (0, 1.18) | 0.66 (0, 2.82) | 1.32 (0, 3.34) | 0.001 | <0.001 | 0.74 | 4.7 |
| F. nucleatum | % | 2.96 (0, 8.27) | 2.33 (0, 7.32) | 3.29 (0, 10.74) | 3.30 (0, 9.56) | 0.251 | 0.196 | 0.59 | 3.9 |
| E. corrodens | % | 0.00 (0, 0.96) | 0.00 (0, 1.04) | 0.00 (0, 1.32) | 0.00 (0, 0.1) | 0.697 | 0.259 | 0.56 | 0.3 |

AUC—Area Under the Curve

Further analysis was computed with a subset of biomarkers demonstrating 1) high Random Forest importance scores; 2) relative low p values; and 3) high AUCs. The diagnostic properties of specific thresholds that gave nearly equal levels of sensitivity and specificity for the selection of biomarkers. MMP-8, MMP-9 and calprotectin demonstrated significant abilities to predict disease category (ORs ranged from 5.3-2.7) for these markers as shown in Table 11.

TABLE 11

Diagnostic properties of specific thresholds of selected salivary biomarkers and plaque biofilm pathogens.

| | | Threshold | Above Threshold | Periodontitis No (n) | Periodontitis Yes (n) | Sens | Spec | Odds Ratio | 95% CI |
|---|---|---|---|---|---|---|---|---|---|
| Biomarker | | | | | | | | | |
| MMP8 | ng/mL | 87.0 | − | 28 | 12 | 0.69 | 0.70 | 5.3 | (2.0, 13.7) |
| | | | + | 12 | 27 | | | | |
| MMP9 | ng/mL | 240.0 | − | 28 | 12 | 0.69 | 0.70 | 5.3 | (2.0, 13.7) |
| | | | + | 12 | 27 | | | | |
| Calprotectin | ng/mL | 3.6 | − | 25 | 15 | 0.62 | 0.63 | 2.7 | (1.1, 6.6) |
| | | | + | 15 | 24 | | | | |

TABLE 11-continued

Diagnostic properties of specific thresholds of selected salivary biomarkers and plaque biofilm pathogens.

| | | Threshold | Above Threshold | Periodontitis No (n) | Periodontitis Yes (n) | Sens | Spec | Odds Ratio | 95% CI |
|---|---|---|---|---|---|---|---|---|---|
| IL6 | pg/mL | 22.4 | − | 24 | 16 | 0.59 | 0.60 | 2.2 | (0.9, 5.3) |
| | | | + | 16 | 23 | | | | |
| IL1β | pg/mL | 235.8 | − | 22 | 18 | 0.54 | 0.55 | 1.4 | (0.6, 3.5) |
| | | | + | 18 | 21 | | | | |
| IL10 | pg/mL | 520.9 | − | 22 | 18 | 0.54 | 0.55 | 1.4 | (0.6, 3.5) |
| | | | + | 18 | 21 | | | | |
| OPG | pg/mL | 2.0 | − | 17 | 22 | 0.44 | 0.43 | 0.6 | (0.2, 1.4) |
| | | | + | 23 | 17 | | | | |
| ICTP | ng/mL | 0.7 | − | 16 | 23 | 0.41 | 0.40 | 0.5 | (0.2, 1.1) |
| | | | + | 24 | 16 | | | | |
| Pathogen | | | | | | | | | |
| T. denticola | % | 0.2 | − | 33 | 7 | 0.82 | 0.83 | 21.6 | (6.8, 68.4) |
| | | | + | 7 | 32 | | | | |
| T. forsythia | % | 0.1 | − | 32 | 8 | 0.80 | 0.80 | 15.5 | (5.2, 46.4) |
| | | | + | 8 | 31 | | | | |
| P. gingivalis | % | 0.1 | − | 31 | 8 | 0.80 | 0.78 | 13.3 | (4.6, 39.1) |
| | | | + | 9 | 31 | | | | |
| P. intermedia | % | 0.4 | − | 29 | 11 | 0.72 | 0.73 | 6.7 | (2.5, 18) |
| | | | + | 11 | 28 | | | | |
| C. rectus | % | 0.1 | − | 25 | 15 | 0.62 | 0.63 | 2.7 | (1.1, 6.6) |
| | | | + | 15 | 24 | | | | |
| F. nucleatum | % | 2.8 | − | 24 | 16 | 0.59 | 0.60 | 2.2 | (0.9, 5.3) |
| | | | + | 16 | 23 | | | | |
| E. corrodens | % | 0.0 | − | 35 | 31 | 0.21 | 0.88 | 1.8 | (0.5, 6.1) |
| | | | + | 5 | 8 | | | | |

Sens Sensitivity
Spec Specificity
CI Confidence Interval

Table 11 demonstrates the median levels as a percentage of the flora of selected red and orange complex organisms for their ability to identify periodontal disease category. An even greater diagnostic ability of these organisms was demonstrated as compared to those revealed by the salivary biomarkers. When comparing low risk and high risk groups, *T. denticola, P. gingivalis, T. forsythus, P. intermedia*, and *C. rectus* all demonstrated significant differences between groups (p<0.001). *F. nucleatum* and *E. corrodens* did not demonstrate a significant relationship. When the diagnostic properties were evaluated for the pathogens demonstrating significant differences between groups, good sensitivity and specificity for disease category were shown as well as ORs (21.6-2.7) for *T. denticola, P. gingivalis, T. forsythus, P. intermedia*, and *C. rectus* (Table 11).

Example 4

Figure 9:
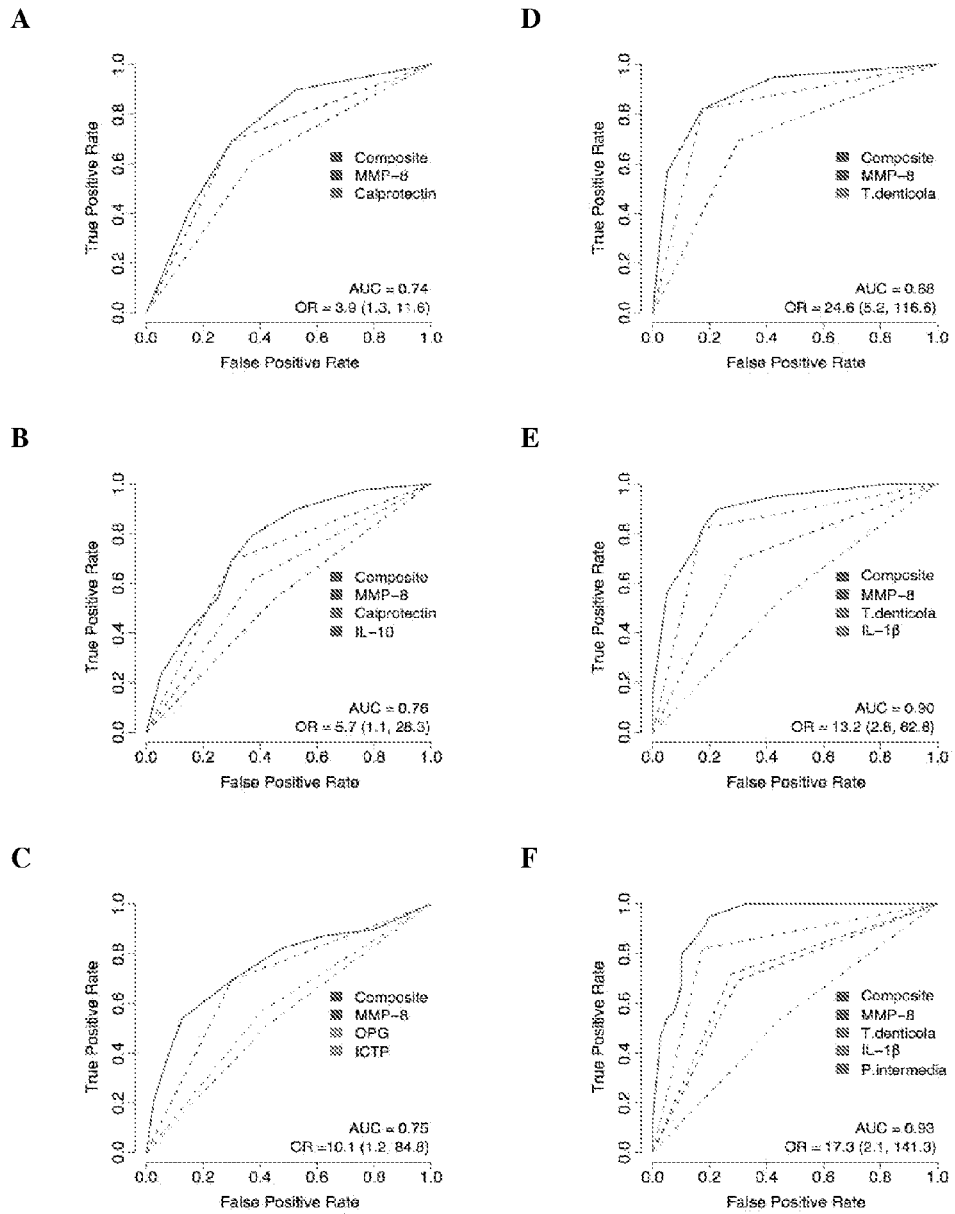
FIG. 9 depicts ROCs of combinatorial permutations of salivary biomarkers coupled with biofilm subgingival pathogens measured by quantitative PCT (qPCR). AUC=area under the curve; OR=odds ratio, numbers in brackets are 95% confidence intervals.

Multi-analyte assessments were performed using various combinations of salivary biomarkers and plaque biofilm levels (FIG. 9). For example, when MMP-8 and calprotectin were combined to predict "high-risk" periodontal status, an AUC of 0.74 was found with a corresponding OR=3.9 (95% CI 1.3, 11.6) (FIG. 9A). When multiple biomarkers were combined such as MMP-8, OPG and ICTP, the AUC was increased to 0.75 with OR=10.1 (95% CI=1.2, 84.8) (FIG. 9C). When the microbial biofilm was combined with the biomarkers, the predictive values increased markedly. FIG. 9D demonstrates the combination of MMP-8 and *T. denticola* with a resultant AUC=0.88 (OR=24.6, 95%=CI 5.2, 116.6). Further improvements in the OR were noted when several pathogens were combined. Given the relatively small sample of 99 subjects, OR could not be determined for many combinations given that all cases of periodontal disease category were correctly identified when comprehensive combinations were chosen and were considered infinite for these permutations (Table 12, below). These results suggest that although the study of 99 subjects was able to determine differences in biomarker/biofilm levels to identify disease category, a much larger sample is needed to generate ORs that can be usable given the high level of accuracy demonstrated in this patient cohort.

TABLE 12

Positive and Negative Predictive Values of specific thresholds of selected salivary biomarkers and plaque biofilm pathogens.

| | | Threshold | Above Threshold | Periodontitis No (n) | Periodontitis Yes (n) | PPV | NPV |
|---|---|---|---|---|---|---|---|
| Biomarker | | | | | | | |
| MMP-8 | ng/mL | 87.0 | − | 28 | 12 | 0.69 | 0.70 |
| | | | + | 12 | 27 | | |

TABLE 12-continued

Positive and Negative Predictive Values of specific thresholds of selected salivary biomarkers and plaque bioflim pathogens.

|  |  | Threshold | Above Threshold | Periodontitis No (n) | Periodontitis Yes (n) | PPV | NPV |
|---|---|---|---|---|---|---|---|
| MMP-9 | ng/mL | 240.0 | − | 28 | 12 | 0.69 | 0.70 |
|  |  |  | + | 12 | 27 |  |  |
| Calprotectin | ng/mL | 3.6 | − | 25 | 15 | 0.62 | 0.63 |
|  |  |  | + | 15 | 24 |  |  |
| IL-6 | pg/mL | 22.4 | − | 24 | 16 | 0.59 | 0.60 |
|  |  |  | + | 16 | 23 |  |  |
| IL-1β | pg/mL | 235.8 | − | 22 | 18 | 0.54 | 0.55 |
|  |  |  | + | 18 | 21 |  |  |
| IL-10 | pg/mL | 520.9 | − | 22 | 18 | 0.54 | 0.55 |
|  |  |  | + | 18 | 21 |  |  |
| OPG | pg/mL | 2.0 | − | 17 | 22 | 0.43 | 0.44 |
|  |  |  | + | 23 | 17 |  |  |
| ICTP | ng/mL | 0.7 | − | 16 | 23 | 0.40 | 0.41 |
|  |  |  | + | 24 | 16 |  |  |
| Pathogen |  |  |  |  |  |  |  |
| T. denticola | % | 0.2 | − | 33 | 7 | 0.82 | 0.83 |
|  |  |  | + | 7 | 32 |  |  |
| T. forsythia | % | 0.1 | − | 32 | 8 | 0.80 | 0.80 |
|  |  |  | + | 8 | 31 |  |  |
| P. gingivalis | % | 0.1 | − | 31 | 8 | 0.78 | 0.80 |
|  |  |  | + | 9 | 31 |  |  |
| P. intermedia | % | 0.4 | − | 29 | 11 | 0.72 | 0.73 |
|  |  |  | + | 11 | 28 |  |  |
| C. rectus | % | 0.1 | − | 25 | 15 | 0.62 | 0.63 |
|  |  |  | + | 15 | 24 |  |  |
| F. nucleatum | % | 2.8 | − | 24 | 16 | 0.59 | 0.60 |
|  |  |  | + | 16 | 23 |  |  |
| E. corrodens | % | 0.0 | − | 35 | 31 | 0.62 | 0.53 |
|  |  |  | + | 5 | 8 |  |  |

PPV—Positive Predictive Value
NPV—Negative Predictive Value

---

What is claimed:

1. A diagnostic method to determine probability of an oral disease state comprising
   (a) determining the levels of two or more biomarkers in a sample collected from a first individual, wherein a first biomarker is a bone-specific marker and a second biomarker is a plaque biofilm pathogen marker, said levels of said two or more biomarkers indicating the probability of said oral disease state, wherein the first biomarker is not type I collagen pyridinoline cross-linked telopeptide (ICTP);
   wherein elevated levels of said two or more biomarkers from said first individual compared to levels of identical biomarkers from a second, healthy individual, or compared to biomarker levels of said first individual measured at an earlier time point are indicative of occurrence of oral disease in said first individual with a probability of diagnosing the disease state equal to or greater than 70%; and
   (b) treating said oral disease by administering an amount of a therapeutic or prophylactic composition sufficient to reduce activity of said two or more biomarkers.

2. The method of claim 1 which determines susceptibility to oral disease and said levels of said two or more biomarkers are indicative of susceptibility to oral disease if said levels of said two or more biomarkers from said first individual are elevated compared to levels of identical biomarkers from the second individual.

3. The method of claim 1 wherein said levels of said two or more biomarkers are indicative of susceptibility to oral disease if said levels of said two or more biomarkers from said first individual are elevated compared to biomarker levels of the first individual measured at an earlier time point.

4. The method of claim 1 wherein said levels of said two or more biomarkers are indicative of progression of oral disease if said levels of said two or more biomarkers from said first individual are elevated compared to biomarker levels of the first individual measured at an earlier time point.

5. The method of claim 1 wherein the probability of diagnosing said disease is equal to or greater than 80%.

6. The method of claim 5 wherein the two or more biomarkers include the combinations of biomarkers as set out in Table 2.

7. The method of claim 1 wherein the levels of two biomarkers are determined.

8. The method of claim 1 wherein the levels of three, four, or five biomarkers are determined.

9. The method of claim 1 wherein the two or more biomarkers are selected from the group consisting of *Aggregatibacter actinomycetemcomitans*, *Campylobacter rectus*, *Fusobacterium nucleatum*, *Prevotella intermedia*, *Porphyromonas gingivalis*, *Tannerella forsythia*, *Treponema denticola*, matrix metalloproteinase-8 (MMP-8), matrix metalloproteinase-9 (MMP-9), osteoprotegerin (OPG), interleukin-1 beta (IL-1β), interleukin-6 (IL-6), interleukin-4 (IL-4), interleukin-10 (IL-10), interleukin-2 (IL-2), interleukin-13 (IL-13), calprotectin, tumor necrosis factor α (TNFα) and combinations thereof.

10. The method of claim 1 wherein the two or more biomarkers include the combinations of biomarkers as set out in Table 1.

11. The method of claim 1 wherein the probability is calculated in a method comprising the steps of:
    determining the levels of two or more biomarkers in said first individual and a second individual,
    generating a receiver operating characteristic (ROC) curve, and calculating area under said ROC curve (AUC), said area providing the probability of said oral disease.

12. The method of claim 1 wherein the sample is selected from the group consisting of a bodily fluid, tissue and organ.

13. The method of claim 12 wherein the fluid is saliva.

14. The method of claim 1 wherein the biomarker levels are biomarker protein levels in the sample.

15. The method of claim 1 wherein said oral disease is periodontal disease.

16. The method of claim 1 wherein said oral disease is peri-implant disease.

17. A kit for carrying out the method of claim 1, the kit comprising: a) a sterile plastic tube for sample collection, and b) one or more components selected from the group consisting of one or more reagents for performing the assay, a calibration standard and a quality control sample.

18. The method of claim 1, said two or more biomarkers further comprising determining the level of a third pro-inflammatory marker and/or the level of type I collagen pyridinoline cross-linked telopeptide (ICTP).

19. The method of claim 1, wherein said oral disease is treated by administering an amount of a therapeutic composition to reduce activity of the two or more biomarkers.

20. The method of claim 1 wherein the composition comprises an inhibitory RNA, an antibody and/or an antibiotic.

21. The method of claim 1 wherein the probability of diagnosing said disease is equal to or greater than 90%.

22. The method of claim 21 wherein the two or more biomarkers include the combinations of biomarkers as set out in Table 3.

23. A diagnostic method to determine probability of an oral disease state comprising the step of determining the levels of two or more biomarkers in a sample collected from an individual, wherein a first biomarker is a bone-specific marker and a second biomarker is a plaque biofilm pathogen marker, said levels of said two or more biomarkers indicating the probability of said oral disease state, wherein the first biomarker is not type I collagen pyridinoline cross-linked telopeptide (ICTP);
   wherein said method determines effectiveness of oral disease treatment, wherein said levels of said two or more biomarkers are indicative of effective oral disease treatment if said levels of said two or more biomarkers from said individual are decreased compared to levels of identical biomarkers from the individual measured at an earlier time point; and
   wherein decreased levels of said two or more biomarkers are indicative of effective oral disease treatment in said individual with a probability equal to or greater than 70%, and
   wherein increased levels of said two or more biomarkers in said individual compared to levels of identical biomarkers from the individual measured at an earlier time point are indicative of ineffective oral disease treatment, and the method then further comprises the step of treating said oral disease by administering an amount of a therapeutic composition to reduce activity of said two or more biomarkers.

24. The method of claim 23 wherein the composition comprises an inhibitory RNA, an antibody and/or an antibiotic.

* * * * *